US009193799B2

(12) United States Patent
Tesar et al.

(10) Patent No.: US 9,193,799 B2
(45) Date of Patent: Nov. 24, 2015

(54) FULLY HUMAN THERAPEUTIC ANTIBODIES SPECIFIC FOR HUMAN CD38

(71) Applicant: MORPHOSYS AG, Martinsried (DE)

(72) Inventors: Michael Tesar, Weilheim (DE); Ute Jäger, München (DE)

(73) Assignee: MorphoSys AG, Planegg (DE)

( * ) Notice: Subject to any disclaimer, the term of this patent is extended or adjusted under 35 U.S.C. 154(b) by 59 days.

(21) Appl. No.: 13/918,199

(22) Filed: Jun. 14, 2013

(65) Prior Publication Data
US 2013/0273072 A1 Oct. 17, 2013

Related U.S. Application Data

(60) Division of application No. 13/291,473, filed on Nov. 8, 2011, now Pat. No. 8,486,394, which is a continuation of application No. 12/089,806, filed as application No. PCT/EP2006/009889 on Oct. 12, 2006, now Pat. No. 8,088,896.

(60) Provisional application No. 60/725,297, filed on Oct. 12, 2005.

(51) Int. Cl.
C07K 16/40 (2006.01)
C07K 16/28 (2006.01)
C07K 16/46 (2006.01)
C07H 21/00 (2006.01)

(52) U.S. Cl.
CPC ............. *C07K 16/40* (2013.01); *C07K 16/2896* (2013.01); *C07K 2317/565* (2013.01)

(58) Field of Classification Search
None
See application file for complete search history.

(56) References Cited

U.S. PATENT DOCUMENTS

| 5,545,405 | A | 8/1996 | Page |
| 7,084,257 | B2 | 8/2006 | Deshpande et al. |
| 7,091,323 | B2 | 8/2006 | Pan et al. |
| 7,223,397 | B1 | 5/2007 | Rosenblum et al. |
| 7,262,278 | B2 | 8/2007 | Tawara et al. |
| 2002/0164788 | A1 | 11/2002 | Ellis et al. |
| 2003/0211553 | A1 | 11/2003 | Logtenberg et al. |
| 2004/0141982 | A1 | 7/2004 | Lust et al. |
| 2004/0180002 | A1 | 9/2004 | Young et al. |
| 2004/0197328 | A1 | 10/2004 | Young et al. |

FOREIGN PATENT DOCUMENTS

| EP | 1 174 440 A1 | 1/2002 |
| EP | 1720907 A2 | 11/2006 |
| WO | WO 94/017184 | 8/1994 |
| WO | WO 96/16990 A1 | 6/1996 |
| WO | WO 99/62526 A2 | 12/1999 |
| WO | WO 00/40265 A1 | 7/2000 |
| WO | WO 00/48631 A1 | 8/2000 |
| WO | WO 01/05950 A2 | 1/2001 |
| WO | WO 02/06347 A1 | 1/2002 |
| WO | WO 02/32288 A2 | 4/2002 |
| WO | WO 2004/003019 A2 | 1/2004 |
| WO | WO 2005/042019 A1 | 5/2004 |
| WO | WO 2005/087806 A2 | 9/2005 |
| WO | WO 2005/103083 A2 | 11/2005 |
| WO | WO 2006/088951 A2 | 8/2006 |
| WO | WO 2006/099875 A1 | 9/2006 |
| WO | WO 2006/110581 A2 | 10/2006 |
| WO | WO 2006/125640 A2 | 11/2006 |

OTHER PUBLICATIONS

U.S. Appl. No. 10/588,568, filed Aug. 4, 2006, Tesar et al.
U.S. Appl. No. 11/920,830, filed May 24, 2006, Tesar et al.
U.S. Appl. No. 12/089,806, filed Oct. 12, 2006, Tesar et al.
U.S. Appl. No. 13/291,437, filed Nov. 8, 2011, Tesar et al.
Abaza et al., "Effects of Amino Acid Substitutions Outside an Antigenic Site on Protein Binding to Monoclonal Antibodies of Pre-determined Specificity Obtained by Peptide Immunization: Demonstration with Region 94-100 (Antigenic Site 3) of Myoglobin," Journal of Protein Chemistry, 1992, 11(5):433-444.
Antonelli et al., "Human anti-CD38 autoantibodies raise intracellular calcium and stimulate insulin release in human pancreatic islets," Diabetes, May 2001, 50:985-991.
Ausiello et al., "Functional topography of discrete domains of human CD38," Tissue Antigens, Dec. 2000, 56(6):539-547.
Bollen et al., "The Goettingen Minipig in pharmacology and toxicology" Pharmacology and Toxicology, vol. 80, No. Suppl. 2, 1997, pp. 3-4, XP009075772 & Workshop and Symposium on Anaesthesia and Experimental Surgery and Research Application of Minipigs; Odense, Denmark; Jun. 11-12, 1996 ISSN: 0901-9928.
Bowie et al., "Deciphering the Message in Protein Sequences: Tolerance to Amino Acid Substitutions," Science, 1990, 247:1306-1310.
Brorson et al., "Mutational Analysis of Avidity and Fine Specificity of Anti-Levan Antibodies," J. lmmun., 1999, 163:6694-6701.
Brummell et al., "Probing the combining site of anti-carbohydrate antibody by saturation-mutagenesis: role of the heavy-chain CDR3 residues," Biochemistry, 1993, 32:1180-1187.
Burks et al., "In vitro scanning saturation mutagenesis of an antibody binding pocket," Proc. Natl. Acad. Sci. USA, Jan. 1997, 94:412-417.
Cassel et al., "A peptide mimetic of an anti-CD4 monoclonal antibody by rational design," Biochemical and Biophysical Communications, 2003, 307:198-205.
Chamow et al., "A Humanized, bispecific immunoadhesin-antibody that retargets CD3+ effectors to kill Hiv-1-infected cells," J. Immunol., Nov. 1, 1994, 153(9):4268-4280.
Chen et al., "Selection and Analysis of an Optimized Anti-Vegf Antibody: Crystal Structure of an Affinity-matured Fab in Complex with Antigen," J. Mol. Biol., 1999, 283:865-881.
Colman, P.M., "Effects of amino acid sequence changes on antibody-antigen interactions," Research in Immunology, 1994, 145(1):33-36.
Colman, P.M., "Effects of amino acid sequence changes on antibody-antigen interactions," Research in Immunology, 1994, 145:33-36.
DePascalis et al., "Grafting of 'Abbreviated' Complementarity-Determining Regions Containing Specificity-Determining Residues Essential for Ligand Contact to Engineer a Less Immunogenic Humanized Monoclonal Antibody," J. Immunol., 2002, 169:3076-3084.

(Continued)

*Primary Examiner* — Peter J Reddig
(74) *Attorney, Agent, or Firm* — Paul F. Wiegel

(57) ABSTRACT

The present invention nucleic acids encoding novel antibodies and functional fragments thereof specific for CD38. Such antibodies are useful for the treatment of diseases associated with CD38 expression, including hematological malignancies such as multiple myeloma.

40 Claims, 36 Drawing Sheets

(56) References Cited

OTHER PUBLICATIONS

Deshpande et al., "Cloning and functional characterization of cDNA encoding porcine CD38" FASEB Journal, vol. 18, No. 4-5, 2004, pp. Abst. 842.4, URL-http://ww, XP009075817 & FASEB Meeting on Experimental Biology: Translating the Genome; Washington, District of Columbia, USA; April 17-21, 2004 ISSN: 0892-6638.

Dufner et al., "Harnessing phage and ribosome display for antibody optimization," Trends in Biotechnology, 2006, 24(11):523-529.

Ellis et al., "Engineered anti-CD38 monoclonal antibodies for immunotherapy of multiple myeloma," Journal of Immunology, The Williams and Wilkins Co. Baltimore, US, vol. 155, No. 2, 1995, pp. 925-937, XP002146232 ISSN: 0022-1767.

Ferrero et al., "Characterization and phylogenetic epitope mapping of CD38 ADPR cyclase in the cynomolgus macaque," BMC Immunology, vol. 5, Sep. 2004 (2004-09), 13 pages, XP002410155 ISSN: 1471-2172.

Flavell et al., "Therapy of human T-cell acute lymphoblastic leukaemia with a combination of anti-CD7 and anti-CD38-saporin immunotoxins is significantly better than therapy with each individual immunotoxin," Br. J. Cancer., 2001, 84(4):571-578.

Funaro et al., "Involvement of the multilineage CD38 molecule in a unique pathway of cell activation and proliferation," J. Immunol., Oct. 15, 1990, 145(8):2390-2396.

Gura, Trisha, "Systems for Identifying New Drugs Are Often Faulty," Science, Nov. 7, 1997, 278:1041-1042.

Gussow et al., "Humanization of Monoclonal Antibodies," Methods in Enzymology, 1991, 203:99-121.

Holm et al., "Functional mapping and single chain construction of the anti-cytokeratin 8 monoclonal antibody TS1," Molecular Immunology, 2007, 44:1075-1084.

Hoshino et al., "Mapping of the catalytic and epitopic sites of human CD38/Nad+ glycohydrolase to a functional domain in the carboxyl terminus," J Immunol., 1997, 158(2):741-747.

Jackson et al., "Isolation of a cDNA encoding the human CD38 (T10) molecule, a cell surface glycoprotein with an unusual discontinuous pattern of expression during lymphocyte differentiation," J Immunol., Apr. 1, 1990, 144(7):2811-2815.

Jang et al., "The structural basis for DNA binding by an anti-DNA autoantibody," Molecular Immunology, 1998, 35:1207-1217. 2006.

Kaiser, Jocelyn, "First Pass at Cancer Genome Reveals Complex Landscape," Science, 313:1370.

Knappik et al., "Fully synthetic human combinatorial antibody libraries (HuCAL) based on modular consensus frameworks and CDRs randomized with trinucleotides," J. Mol. Biol., 2000, 296:57-86.

Kobayashi et al., "Tryptophan H33 plays an important role in pyrimidine (6-4) pyrimidone photoproduct binding by a high-affinity antibody," Protein Engineering, 1999, 12(10):879-884.

Konopleva et al., "Ligation of cell surface CD38 protein with agonistic monoclonal antibody cell growth signal in myeloid leukemia cells," J. Immunol., 1998, 161(9):4702-4708.

Krebs et al., "High-throughput generation and engineering of recombinant human antibodies," Immunol. Methods, 2001, 254:67-84.

Kumar et al., "Molecular Cloning and Expression of the Fabs of Human Autoantibodies in *Eschericia coli*," J. Biol. Chem., 2000, 275:35129-35136.

MacCallum et al., "Antibody-antigen Interactions: Contact Analysis and Binding Site Topography," J. Mol. Biol., 1996, 262:732-745.

Malavasi et al., "Characterization of a murine monoclonal antibody specific for human early lymphohemopoietic cells," Hum. Immunol., Jan. 1984, 9(1):9-20.

Maloney et al., "Antibody Therapy for Treatment of Multiple Myeloma," Seminars in Hematology, Jan. 1999, 36(1):Suppl 3:30-33, XP000857401 ISSN: 0037-1963.

Marchetti et al., "Prolonged in vitro exposure to autoantibodies against CD38 impairs the function and survival of human pancreatic islets," Diabetes, Dec. 2002, 51(Suppl. 3):474-477.

Mehta et al., "Retinoic acid-induced CD38 antigen as a target for immunotoxin-mediated killing of leukemia cells," Mol. Cancer Ther., 2004, 3:345-352.

Namba et al., "Establishment of five human myeloma cell lines," In Vitro Cell. & Dev. 1989, 25(8):723-729.

Nata et al. "Human gene encoding CD38 (ADP-ribosyl cyclase/cyclic ADP-ribose hydrolase): organization, nucleotide sequence and alternative splicing," Gene, 1997, 186(2):285-292.

Reinherz et al., "Discrete stages of human intrathymic differentiation: Analysis of normal thymocytes and leukemic lymphoblasts of T-cell lineage," PNAS USA, Mar. 1980, 77(3):1588-1592.

Rudikoff et al., "Single amino acid substitutions altering antigen-binding specificity," Proc. Natl. Acad. Sci. USA, 1982, 79:1979-1983.

Smith-Gill et al., "Contributions of Immunoglobulin Heavy and Light Chains to Antibody Specificity for Lysozyme and Two Haptens," J. Immunol., 1987, 139:4153-4144.

Song et al., "Light Chain of Natural Antibody Plays a Dominant Role in Protein Antigen Binding," Biochemical and Biophysical Research Communications, 2000, 268:390-394.

Stevenson et al., "Preliminary Studies for an Immunotherapy Approach to the Treatment of Human Myeloma Using Chimeric Anti-CD38 Antibody," Blood, Mar. 1, 1991, 77(5):1071-1079, XP000930093 ISSN: 006-4971.

Vajdos et al., "Comprehensive Functional Maps of the Antigen-binding Site of an Anti-ErbB2 Antibody Obtained with Shotgun Scanning Mutagenesis," J. Mol. Biol., 2002, 320:415-428.

Ward et al., "Binding activities of a repertoire of single immunoglobulin variable domains secreted from *Escherichia coli*," Nature, Oct. 12, 1989, 341:544-546.

Wu et al., "Humanization of a Murine Monoclonal Antibody by Simultaneous Optimization of Framework and CDR Residues," J. Mol. Biol., 1999, 294:151-162.

Zhou et al., "Optimization of primer sequences for mouse scFv repertoire display library construction," Nucleic Acids Res., 1994, 22(5):888-889.

Zocchi et al., "A single protein immunologically identified as CD38 displays NAD+ glycohydrolase, ADP-ribosyl cyclase and cyclic ADP-ribose hydrolase activities at the outer surface of human erythrocytes," Biochemical and Biophysical Research Communications, Nov. 15, 1993, 196(3):1459-1465, XP002410154 ISSN: 0006-291X.

Human leukocyte differentiation antigens: review of the Third International Workshop, Molecular and Cellular Probes (1987) 1, 55-60.

Figure 1a

Variable Heavy Chain DNA

3076_VH1A (SEQ ID NO: 1):
CAGGTGCAATTGGTTCAGTCTGGCGCGGAAGTGAAAAAACCGGGCAGCAGCGTGAAAGTGAGC
TGCAAAGCCTCCGGAGGCACTTTTTCTTCTAATGCTATTTCTTGGGTGCGCCAAGCCCCTGGGCA
GGGTCTCGAGTGGATGGGCAATATCTGGCCGATTTTTGGCACTGCGAATTACGCGCAGAAGTTT
CAGGGCCGGGTGACCATTACCGCGGATGAAAGCACCAGCACCGCGTATATGGAACTGAGCAGC
CTGCGTAGCGAAGATACGGCCGTGTATTATTGCGCGCGTAATGGTTATCTTGATACTAATACTTA
TATTGATTATTGGGGCCAAGGCACCCTGGTGACGGTTAGCTCA

3078_VH3 (SEQ ID NO: 2):
CAGGTGCAATTGGTGGAAAGCGGCGGCGGCCTGGTGCAACCGGGCGGCAGCCTGCGTCTGAG
CTGCGCGGCCTCCGGATTTACCTTTTCTGATTATGCTATGTCTTGGGTGCGCCAAGCCCCTGGG
AAGGGTCTCGAGTGGGTGAGCGCTATCCGTTATGATGGTAGCAATACCTATTATGCGGATAGCG
TGAAAGGCCGTTTTACCATTTCACGTGATAATTCGAAAAACACCCTGTATCTGCAAATGAACAGC
CTGCGTGCGGAAGATACGGCCGTGTATTATTGCGCGCGTTATTATTCTGGTATTTATCAGCATAT
TGATTATTGGGGCCAAGGCACCCTGGTGACGGTTAGCTCA

3081_ VH3 (SEQ ID NO: 3):
CAGGTGCAATTGGTGGAAAGCGGCGGCGGCCTGGTGCAACCGGGCGGCAGCCTGCGTCTGAG
CTGCGCGGCCTCCGGATTTACCTTTTCTTCTTATGCTCTTCATTGGGTGCGCCAAGCCCCTGGGA
AGGGTCTCGAGTGGGTGAGCTCTATCTCTGGTCTTGGTAGCACTACCTATTATGCGGATAGCGT
GAAAGGCCGTTTTACCATTTCACGTGATAATTCGAAAAACACCCTGTATCTGCAAATGAACAGCC
TGCGTGCGGAAGATACGGCCGTGTATTATTGCGCGCGTTATCATTATGAGTATCATTATTTTTCTT
CTGGTTTTGATAATTGGGGCCAAGGCACCCTGGTGACGGTTAGCTCA

3085_ VH1A (SEQ ID NO: 4):
CAGGTGCAATTGGTTCAGAGCGGCGCGCGGAAGTGAAAAAACCGGGCGCGAGCGTGAAAGTGAGC
TGCAAAGCCTCCGGATATACCTTTACTGGTTATTATATTAATTGGGTCCGCCAAGCCCCTGGGCA
GGGTCTCGAGTGGATGGGCTGGATCTTTCCGAATGGTGGCTCTACGGGTTACGCGCAGAAGTTT
CAGGGCCGGGTGACCATGACCCGTGATACCAGCATTAGCACCGCGTATATGGAACTGAGCAGC
CTGCGTAGCGAAGATACGGCCGTGTATTATTGCGCGCGTGGTAATATTTTTATTTTTGATTATTGG
GGCCAAGGCACCCTGGTGACGGTTAGCTCA

3086_VH3 (SEQ ID NO: 5):
CAGGTGCAATTGGTGGAAAGCGGCGGCGGCCTGGTGCAACCGGGCGGCAGCCTGCGTCTGAG
CTGCGCGGCCTCCGGATTTACCTTTACTTCTTATTATATGCATTGGGTGCGCCAAGCCCCTGGGA
AGGGTCTCGAGTGGGTGAGCTATATCGATTCTTCTGGTAGCTCTACCTATTATGCGGATAGCGTG
AAAGGCCGTTTTACCATTTCACGTGATAATTCGAAAAACACCCTGTATCTGCAAATGAACAGCCT
GCGTGCGGAAGATACGGCCGTGTATTATTGCGCGCGTCAGCTTATGCCTTTTGGTGGTTATTTTG
ATGTTTGGGGCCAAGGCACCCTGGTGACGGTTAGCTCA

3087_ VH3 (SEQ ID NO: 6):
CAGGTGCAATTGGTGGAAAGCGGCGGCGGCCTGGTGCAACCGGGCGGCAGCCTGCGTCTGAG
CTGCGCGGCCTCCGGATTTACCTTTTCTTCTTATTATATGAATTGGGTGCGCCAAGCCCCTGGGA
AGGGTCTCGAGTGGGTGAGCGGTATCTCTGGTGATCCTAGCAATACCTATTATGCGGATAGCGT
GAAAGGCCGTTTTACCATTTCACGTGATAATTCGAAAAACACCCTGTATCTGCAAATGAACAGCC
TGCGTGCGGAAGATACGGCCGTGTATTATTGCGCGCGTGATCTTCCTCTTGTTTATACTGGTTTT
GCTTATTGGGGCCAAGGCACCCTGGTGACGGTTAGCTCA

Figure 1a (Continued)

3088_VH3 (SEQ ID NO: 7):
CAGGTGCAATTGGTGGAAAGCGGCGGCGGCCTGGTGCAACCGGGCGGCAGCCTGCGTCTGAG
CTGCGCGGCCTCCGGATTTACCTTTTCTTCTTATGCTATGAATTGGGTGCGCCAAGCCCCTGGG
AAGGGTCTCGAGTGGGTGAGCGGTATCTCTTCTTGGGGTAGCTCTACCTATTATGCGGATAGCG
TGAAAGGCCGTTTTACCATTTCACGTGATAATTCGAAAAACACCCTGTATCTGCAAATGAACAGC
CTGCGTGCGGAAGATACGGCCGTGTATTATTGCGCGCGTGAGGATGGTTCTTATATGACTGATT
ATTTTGCTTATTGGGGCCAAGGCACCCTGGTGACGGTTAGCTCA

3089_VH2 (SEQ ID NO: 8):
CAGGTGCAATTGAAAGAAAGCGGCCCGGCCCTGGTGAAACCGACCCAAACCCTGACCCTGACC
TGTACCTTTTCCGGATTTAGCCTGTCTTCTGATGGTATGGGTGTGGGTTGGATTCGCCAGCCGCC
TGGGAAAGCCCTCGAGTGGCTGGCTCTTATCGATTGGGATGATGATAAGCGTTATAGCACCAGC
CTGAAAACGCGTCTGACCATTAGCAAAGATACTTCGAAAAATCAGGTGGTGCTGACTATGACCAA
CATGGACCCGGTGGATACGGCCACCTATTATTGCGCGCGTTTTAATTGGTTTTATCGTCTTGCTT
TTGTTAATCCTGATGTTTGGGGCCAAGGCACCCTGGTGACGGTTAGCTCA

3101_VH2 (SEQ ID NO: 9):
CAGGTGCAATTGAAAGAAAGCGGCCCGGCCCTGGTGAAACCGACCCAAACCCTGACCCTGACC
TGTACCTTTTCCGGATTTAGCCTGTCTACTTCTCGTGTTGGTGTGTCTTGGATTCGCCAGCCGCC
TGGGAAAGCCCTCGAGTGGCTGGCTCATATCGATTGGAATGATGATAAGTATTATAGCACCAGC
CTGAAAACGCGTCTGACCATTAGCAAAGATACTTCGAAAAATCAGGTGGTGCTGACTATGACCAA
CATGGACCCGGTGGATACGGCCACCTATTATTGCGCGCGTGAGGATCGTCTTCTTGGTGGTTAT
GGTTATGATGTTTGGGGCCAAGGCACCCTGGTGACGGTTAGCTCA

3102_VH4 (SEQ ID NO: 10):
CAGGTGCAATTGCAAGAAAGTGGTCCGGGCCTGGTGAAACCGGGCGAAACCCTGAGCCTGACC
TGCACCGTTTCCGGAGGCAGCATTTCTGGTAATTATTGGTCTTGGATTCGCCAGGCCCCTGGGA
AGGGTCTCGAGTGGATTGGCGATTATCATGGCTCTACCTATTATAATCCGAGCCTGAAAGGCCG
GGTGACCATTAGCGTTGATACTTCGAAAAACCAGTTTAGCCTGAAACTGAGCAGCGTGACGGCG
GAAGATACGGCCGTGTATTATTGCGCGCGTGAGCAGTATCATTGGGGTCTTGCTTGGACTGGTT
TTGATAATTGGGGCCAAGGCACCCTGGTGACGGTTAGCTCA

3127_VH5 (SEQ ID NO: 11):
CAGGTGCAATTGGTTCAGAGCGGCGCGGAAGTGAAAAAACCGGGCGAAAGCCTGAAAATTAGCT
GCAAAGGTTCCGGATATTCCTTTTCTACTTCTTGGGTTGGTTGGGTGCGCCAGATGCCTGGGAA
GGGTCTCGAGTGGATGGGCATTATCGATCCGGATATTAGCTATACCTCTTATTCTCCGAGCTTTC
AGGGCCAGGTGACCATTAGCGCGGATAAAAGCATTAGCACCGCGTATCTTCAATGGAGCAGCCT
GAAAGCGAGCGATACGGCCATGTATTATTGCGCGCGTTATCTTATGGGTCTTGGTTATGATGTTT
GGGGCCAAGGCACCCTGGTGACGGTTAGCTCA

3128_VH2 (SEQ ID NO: 12):
CAGGTGCAATTGAAAGAAAGCGGCCCGGCCCTGGTGAAACCGACCCAAACCCTGACCCTGACC
TGTACCTTTTCCGGATTTAGCCTGTCTCTTCTGGTATGTCTGTGTCTTGGATTCGCCAGCCGCC
TGGGAAAGCCCTCGAGTGGCTGGCTCGTATCTATTCTGATGATTCTAAGTCTTATAGCACCAGCC
TGAAAACGCGTCTGACCATTAGCAAAGATACTTCGAAAAATCAGGTGGTGCTGACTATGACCAAC
ATGGACCCGGTGGATACGGCCACCTATTATTGCGCGCGTGCTGCTCATTGGAATGGTCCTCTTT
TTGATGTTTGGGGCCAAGGCACCCTGGTGACGGTTAGCTCA

Figure 1a (Continued)

3129_VH3 (SEQ ID NO: 13):
CAGGTGCAATTGGTGGAAAGCGGCGGCGGCCTGGTGCAACCGGGCGGCAGCCTGCGTCTGAG
CTGCGCGGCCTCCGGATTTACCTTTTCTAATTATTCTATGAATTGGGTGCGCCAAGCCCCTGGGA
AGGGTCTCGAGTGGGTGAGCTATATCTATGGTGGTGGTAGCTATACCTATTATGCGGATAGCGT
GAAAGGCCGTTTTACCATTTCACGTGATAATTCGAAAAACACCCTGTATCTGCAAATGAACAGCC
TGCGTGCGGAAGATACGGCCGTGTATTATTGCGCGCGTCAGGCTGGTATGTATTTTGATGTTTG
GGGCCAAGGCACCCTGGTGACGGTTAGCTCA

3130_VH4 (SEQ ID NO: 14):
CAGGTGCAATTGCAAGAAAGTGGTCCGGGCCTGGTGAAACCGGGCGAAACCCTGAGCCTGACC
TGCACCGTTTCCGGAGGCAGCATTGGTTATTATTGGAATTGGATTCGCCAGGCCCCTGGGAAGG
GTCTCGAGTGGATTGGCCATATCTCTCGTTTTGGCTCTACCAATTATAATCCGAGCCTGAAAGGC
CGGGTGACCATTAGCGTTGATACTTCGAAAAACCAGTTTAGCCTGAAACTGAGCAGCGTGACGG
CGGAAGATACGGCCGTGTATTATTGCGCGCGGGAGTATACTGGTAATGATTGGTATCGTCAGCA
GGGTCAGCATGCTGATTATTGGGGCCAAGGCACCCTGGTGACGGTTAGCTCA

3131_VH2 (SEQ ID NO: 15):
CAGGTGCAATTGAAAGAAAGCGGCCCGGCCCTGGTGAAACCGACCCAAACCCTGACCCTGACC
TGTACCTTTTCCGGATTTAGCCTGTCTAATTCTGGTGTTGGTGTGGGTTGGATTCGCCAGCCGCC
TGGGAAAGCCCTCGAGTGGCTGGCTGATATCTATTCTGATACTACTAAGCGTTATAGCACCAGCC
TGAAAACGCGTCTGACCATTAGCAAAGATACTTCGAAAAATCAGGTGGTGCTGACTATGACCAAC
ATGGACCCGGTGGATACGGCCACCTATTATTGCGCGCGTTATGGTGAGGCTTATTTTGATTATTG
GGGCCAAGGCACCCTGGTGACGGTTAGCTCA

6183_VH3 (SEQ ID NO: 77)
CAGGTGCAATTGGTGGAAAGCGGCGGCGGCCTGGTGCAACCGGGCGGCAGCCTGCGTCTGAG
CTGCGCGGCCTCCGGATTTACCTTTTCTTCTTATTATATGAATTGGGTGCGCCAAGCCCCTGGGA
AGGGTCTCGAGTGGGTGAGCGGTATTAATATGGAGTCTACTCGTATTTATTATGCTGATTCTGTT
AAGGGTCGTTTTACCATTTCACGTGATAATTCGAAAAACACCCTGTATCTGCAAATGAACAGCCT
GCGTGCGGAAGATACGGCCGTGTATTATTGCGCGCGTGATCTTCCTCTTGTTTATACTGGTTTTG
CTTATTGGGGCCAAGGCACCCTGGTGACGGTTAGCTCA

6184_VH3 (SEQ ID NO: 78)
CAGGTGCAATTGGTGGAAAGCGGCGGCGGCCTGGTGCAACCGGGCGGCAGCCTGCGTCTGAG
CTGCGCGGCCTCCGGATTTACCTTTTCTTCTTATTATATGAATTGGGTGCGCCAAGCCCCTGGGA
AGGGTCTCGAGTGGGTGAGCGCTATTTCTCATGATGGTAATGTTAAGTATTATGCTGATTCTGTT
AAGGGTCGTTTTACCATTTCACGTGATAATTCGAAAAACACCCTGTATCTGCAAATGAACAGCCT
GCGTGCGGAAGATACGGCCGTGTATTATTGCGCGCGTGATCTTCCTCTTGTTTATACTGGTTTTG
CTTATTGGGGCCAAGGCACCCTGGTGACGGTTAGCTCA

6185_VH3 (SEQ ID NO: 79)
CAGGTGCAATTGGTGGAAAGCGGCGGCGGCCTGGTGCAACCGGGCGGCAGCCTGCGTCTGAG
CTGCGCGGCCTCCGGATTTACCTTTTCTTCTTATTATATGAATTGGGTGCGCCAAGCCCCTGGGA
AGGGTCTCGAGTGGGTGAGCGCTATTTCTATGAATGGTGATTATATTTCTTATGCTGATTCTGTTA
AGGGTCGTTTTACCATTTCACGTGATAATTCGAAAAACACCCTGTATCTGCAAATGAACAGCCTG
CGTGCGGAAGATACGGCCGTGTATTATTGCGCGCGTGATCTTCCTCTTGTTTATACTGGTTTTGC
TTATTGGGGCCAAGGCACCCTGGTGACGGTTAGCTCA

Figure 1a (Continued)

6186_VH3 (SEQ ID NO: 80)
CAGGTGCAATTGGTGGAAAGCGGCGGCGGCCTGGTGCAACCGGGCGGCAGCCTGCGTCTGAG
CTGCGCGGCCTCCGGATTTACCTTTTCTTCTTATTATATGAATTGGGTGCGCCAAGCCCCTGGGA
AGGGTCTCGAGTGGGTGAGCGCTATTAATCTTTCTGGTTCTGCTAAGTATTATGCTGATTCTGTTA
AGGGTCGTTTTACCATTTCACGTGATAATTCGAAAAACACCCTGTATCTGCAAATGAACAGCCTG
CGTGCGGAAGATACGGCCGTGTATTATTGCGCGCGTGATCTTCCTCTTGTTTATACTGGTTTTGC
TTATTGGGGCCAAGGCACCCTGGTGACGGTTAGCTCA

6187_VH3 (SEQ ID NO: 81)
CAGGTGCAATTGGTGGAAAGCGGCGGCGGCCTGGTGCAACCGGGCGGCAGCCTGCGTCTGAG
CTGCGCGGCCTCCGGATTTACCTTTTCTTCTTATTATATGAATTGGGTGCGCCAAGCCCCTGGGA
AGGGTCTCGAGTGGGTGAGCGCTATTTCTTCTAATGGTGATATTACTTATTATGCTGATTCTGTTA
AGGGTCGTTTTACCATTTCACGTGATAATTCGAAAAACACCCTGTATCTGCAAATGAACAGCCTG
CGTGCGGAAGATACGGCCGTGTATTATTGCGCGCGTGATCTTCCTCTTGTTTATACTGGTTTTGC
TTATTGGGGCCAAGGCACCCTGGTGACGGTTAGCTCA

6188_VH3 (SEQ ID NO: 82)
CAGGTGCAATTGGTGGAAAGCGGCGGCGGCCTGGTGCAACCGGGCGGCAGCCTGCGTCTGAG
CTGCGCGGCCTCCGGATTTACCTTTTCTTCTTATTATATGAATTGGGTGCGCCAAGCCCCTGGGA
AGGGTCTCGAGTGGGTGAGCGCTATTTCTACTAATGGTTGGCAGACTTATTATGCTGATTCTGTT
AAGGGTCGTTTTACCATTTCACGTGATAATTCGAAAAACACCCTGTATCTGCAAATGAACAGCCT
GCGTGCGGAAGATACGGCCGTGTATTATTGCGCGCGTGATCTTCCTCTTGTTTATACTGGTTTTG
CTTATTGGGGCCAAGGCACCCTGGTGACGGTTAGCTCA

6189_VH3 (SEQ ID NO: 83)
CAGGTGCAATTGGTGGAAAGCGGCGGCGGCCTGGTGCAACCGGGCGGCAGCCTGCGTCTGAG
CTGCGCGGCCTCCGGATTTACCTTTTCTTCTTATTATATGAATTGGGTGCGCCAAGCCCCTGGGA
AGGGTCTCGAGTGGGTGAGCGCTATTAATATGATTGGTAATGTTACTAATTATGCTGATTCTGTTA
AGGGTCGTTTTACCATTTCACGTGATAATTCGAAAAACACCCTGTATCTGCAAATGAACAGCCTG
CGTGCGGAAGATACGGCCGTGTATTATTGCGCGCGTGATCTTCCTCTTGTTTATACTGGTTTTGC
TTATTGGGGCCAAGGCACCCTGGTGACGGTTAGCTCA

6190_VH3 (SEQ ID NO: 84)
CAGGTGCAATTGGTGGAAAGCGGCGGCGGCCTGGTGCAACCGGGCGGCAGCCTGCGTCTGAG
CTGCGCGGCCTCCGGATTTACCTTTTCTTCTTATTATATGAATTGGGTGCGCCAAGCCCCTGGGA
AGGGTCTCGAGTGGGTGAGCGCTATATTAATCCTAATGGTATGATGACTAATTATGCTGATTCTGTTA
AGGGTCGTTTTACCATTTCACGTGATAATTCGAAAAACACCCTGTATCTGCAAATGAACAGCCTG
CGTGCGGAAGATACGGCCGTGTATTATTGCGCGCGTGATCTTCCTCTTGTTTATACTGGTTTTGC
TTATTGGGGCCAAGGCACCCTGGTGACGGTTAGCTCA

6192_VH3 (SEQ ID NO: 85)
CAGGTGCAATTGGTGGAAAGCGGCGGCGGCCTGGTGCAACCGGGCGGCAGCCTGCGTCTGAG
CTGCGCGGCCTCCGGATTTACCTTTTCTTCTTATTATATGAATTGGGTGCGCCAAGCCCCTGGGA
AGGGTCTCGAGTGGGTGAGCGTTATTTCTCCTGGTGGTGAGGCTAAGTCTTATGCTGATTCTGTT
AAGGGTCGTTTTACCATTTCACGTGATAATTCGAAAAACACCCTGTATCTGCAAATGAACAGCCT
GCGTGCGGAAGATACGGCCGTGTATTATTGCGCGCGTGATCTTCCTCTTGTTTATACTGGTTTTG
CTTATTGGGGCCAAGGCACCCTGGTGACGGTTAGCTCA

Figure 1a (Continued)

6195_VH3 (SEQ ID NO: 86)
CAGGTGCAATTGGTGGAAAGCGGCGGCGGCCTGGTGCAACCGGGCGGCAGCCTGCGTCTGAG
CTGCGCGGCCTCCGGATTTACCTTTTCTTCTTATTATATGAATTGGGTGCGCCAAGCCCCTGGGA
AGGGTCTCGAGTGGGTGAGCGCTATTTCTGGTAATGGTGGTCATACTTATTATGCTGATTCTGTT
AAGGGTCGTTTTACCATTTCACGTGATAATTCGAAAAACACCCTGTATCTGCAAATGAACAGCCT
GCGTGCGGAAGATACGGCCGTGTATTATTGCGCGCGTGATCTTCCTCTTGTTTATACTGGTTTTG
CTTATTGGGGCCAAGGCACCCTGGTGACGGTTAGCTCA

6197_VH3 (SEQ ID NO: 87)
CAGGTGCAATTGGTGGAAAGCGGCGGCGGCCTGGTGCAACCGGGCGGCAGCCTGCGTCTGAG
CTGCGCGGCCTCCGGATTTACCTTTTCTTCTTATTATATGAATTGGGTGCGCCAAGCCCCTGGGA
AGGGTCTCGAGTGGGTGAGCGCTATTTCTATGGATGGTGTTTATAAGTATTATGCTGATTCTGTT
AAGGGTCGTTTTACCATTTCACGTGATAATTCGAAAAACACCCTGTATCTGCAAATGAACAGCCT
GCGTGCGGAAGATACGGCCGTGTATTATTGCGCGCGTGATCTTCCTCTTGTTTATACTGGTTTTG
CTTATTGGGGCCAAGGCACCCTGGTGACGGTTAGCTCA

6200_VH3 (SEQ ID NO: 88)
CAGGTGCAATTGGTGGAAAGCGGCGGCGGCCTGGTGCAACCGGGCGGCAGCCTGCGTCTGAG
CTGCGCGGCCTCCGGATTTACCTTTTCTTCTTATTATATGAATTGGGTGCGCCAAGCCCCTGGGA
AGGGTCTCGAGTGGGTGAGCGCTATTTCTAATAATGGTAATGTTACTTATTATGCTGATTCTGTTA
AGGGTCGTTTTACCATTTCACGTGATAATTCGAAAAACACCCTGTATCTGCAAATGAACAGCCTG
CGTGCGGAAGATACGGCCGTGTATTATTGCGCGCGTGATCTTCCTCTTGTTTATACTGGTTTTGC
TTATTGGGGCCAAGGCACCCTGGTGACGGTTAGCTCA

6201_VH3 (SEQ ID NO: 89)
CAGGTGCAATTGGTGGAAAGCGGCGGCGGCCTGGTGCAACCGGGCGGCAGCCTGCGTCTGAG
CTGCGCGGCCTCCGGATTTACCTTTTCTTCTTATTATATGAATTGGGTGCGCCAAGCCCCTGGGA
AGGGTCTCGAGTGGGTGAGCGCTATTTCTATGCATGGTGATACTACTTATTATGCTGATTCTGTT
AAGGGTCGTTTTACCATTTCACGTGATAATTCGAAAAACACCCTGTATCTGCAAATGAACAGCCT
GCGTGCGGAAGATACGGCCGTGTATTATTGCGCGCGTGATCTTCCTCTTGTTTATACTGGTTTTG
CTTATTGGGGCCAAGGCACCCTGGTGACGGTTAGCTCA

6204_VH3 (SEQ ID NO: 90)
CAGGTGCAATTGGTGGAAAGCGGCGGCGGCCTGGTGCAACCGGGCGGCAGCCTGCGTCTGAG
CTGCGCGGCCTCCGGATTTACCTTTTCTTCTTATGCTATGAATTGGGTGCGCCAAGCCCCTGGG
AAGGGTCTCGAGTGGGTGAGCCATATTCGTAAGAAGAATACTTCTTATACTACTGAGTATGCTGC
TTCTGTTAAGGGTCGTTTTACCATTTCACGTGATAATTCGAAAAACACCCTGTATCTGCAAATGAA
CAGCCTGCGTGCGGAAGATACGGCCGTGTATTATTGCGCGCGTGAGGATGGTTCTTATATGACT
GATTATTTTGCTTATTGGGGCCAAGGCACCCTGGTGACGGTTAGCTCA

6214_VH3 (SEQ ID NO: 91)
CAGGTGCAATTGGTGGAAAGCGGCGGCGGCCTGGTGCAACCGGGCGGCAGCCTGCGTCTGAG
CTGCGCGGCCTCCGGATTTACCTTTTCTTCTTATGCTATGAATTGGGTGCGCCAAGCCCCTGGG
AAGGGTCTCGAGTGGGTGAGCAATATTCAGCGTGTTGGTTCTACTTATTATGCTGATTCTGTTAA
GGGTCGTTTTACCATTTCACGTGATAATTCGAAAAACACCCTGTATCTGCAAATGAACAGCCTGC
GTGCGGAAGATACGGCCGTGTATTATTGCGCGCGTGAGGATGGTTCTTATATGACTGATTATTTT
GCTTATTGGGGCCAAGGCACCCTGGTGACGGTTAGCTCA

Figure 1a (Continued)

3077_VH1B (SEQ ID NO: 111)
CAGGTGCAATTGGTTCAGAGCGGCGCGGAAGTGAAAAAACCGGGCGCGAGCGTGAAAGTGAGC
TGCAAAGCCTCCGGATATACCTTTACTTCTTATTCTATTAATTGGGTCCGCCAAGCCCCTGGGCA
GGGTCTCGAGTGGATGGGCTATATCGATCCGAATCGTGGCAATACGAATTACGCGCAGAAGTTT
CAGGGCCGGGTGACCATGACCCGTGATACCAGCATTAGCACCGCGTATATGGAACTGAGCAGC
CTGCGTAGCGAAGATACGGCCGTGTATTATTGCGCGCGTGAGTATATTTATTTTATTCATGGTAT
GCTTGATTTTTGGGGCCAAGGCACCCTGGTGACGGTTAGCTCA

3079_VH3 (SEQ ID NO: 112)
CAGGTGCAATTGGTGGAAAGCGGCGGCGGCCTGGTGCAACCGGGCGGCAGCCTGCGTCTGAG
CTGCGCGGCCTCCGGATTTACCTTTTCTAATTATGGTATGCATTGGGTGCGCCAAGCCCCTGGG
AAGGGTCTCGAGTGGGTGAGCAATATCCGTTCTGATGGTAGCTGGACCTATTATGCGGATAGCG
TGAAAGGCCGTTTTACCATTTCACGTGATAATTCGAAAAACACCCTGTATCTGCAAATGAACAGC
CTGCGTGCGGAAGATACGGCCGTGTATTATTGCGCGCGTCGTTATTGGTCTAAGTCTCATGCTTC
TGTTACTGATTATTGGGGCCAAGGCACCCTGGTGACGGTTAGCTCA

3080_VH3 (SEQ ID NO: 113)
CAGGTGCAATTGGTGGAAAGCGGCGGCGGCCTGGTGCAACCGGGCGGCAGCCTGCGTCTGAG
CTGCGCGGCCTCCGGATTTACCTTTTCTTCTTATGGTATGCATTGGGTGCGCCAAGCCCCTGGG
AAGGGTCTCGAGTGGGTGAGCAATATCTATTCTGATGGTAGCAATACCTTTTATGCGGATAGCGT
GAAAGGCCGTTTTACCATTTCACGTGATAATTCGAAAAACACCCTGTATCTGCAAATGAACAGCC
TGCGTGCGGAAGATACGGCCGTGTATTATTGCGCGCGTAATATGTATCGTTGGCCTTTTCATTAT
TTTTTTGATTATTGGGGCCAAGGCACCCTGGTGACGGTTAGCTCA

Figure 1b

Variable Heavy Chain Peptide (CDR Regions in Bold or underlined)

3076_VH1A (SEQ ID NO: 16):
QVQLVQSGAEVKKPGSSVKVSCKASGGTFSSNAISWVRQAPGQGLEWMGNIWPIFGTANYAQKFQ
GRVTITADESTSTAYMELSSLRSEDTAVYYCARNGYLDTNTYIDYWGQGTLVTVSS

3078_VH3 (SEQ ID NO: 17):
QVQLVESGGGLVQPGGSLRLSCAASGFTFSDYAMSWVRQAPGKGLEWVSAIRYDGSNTYYADSVK
GRFTISRDNSKNTLYLQMNSLRAEDTAVYYCARYYSGIYQHIDYWGQGTLVTVSS

3081_VH3 (SEQ ID NO: 18):
QVQLVESGGGLVQPGGSLRLSCAASGFTFSSYALHWVRQAPGKGLEWVSSISGLGSTTYYADSVK
GRFTISRDNSKNTLYLQMNSLRAEDTAVYYCARYHYEYHYFSSGFDNWGQGTLVTVSS

3085_VH1A (SEQ ID NO: 19):
QVQLVQSGAEVKKPGASVKVSCKASGYTFTGYYINWVRQAPGQGLEWMGWIFPNGGSTGYAQKF
QGRVTMTRDTSISTAYMELSSLRSEDTAVYYCARGNIFIFDYWGQGTLVTVSS

3086_VH3 (SEQ ID NO: 20):
QVQLVESGGGLVQPGGSLRLSCAASGFTFTSYYMHWVRQAPGKGLEWVSYIDSSGSSTYYADSVK
GRFTISRDNSKNTLYLQMNSLRAEDTAVYYCARQLMPFGGYFDVWGQGTLVTVSS

3087_VH3 (SEQ ID NO: 21):
QVQLVESGGGLVQPGGSLRLSCAASGFTFSSYYMNWVRQAPGKGLEWVSGISGDPSNTYYADSVK
GRFTISRDNSKNTLYLQMNSLRAEDTAVYYCARDLPLVYTGFAYWGQGTLVTVSS

3088_VH3 (SEQ ID NO: 22):
QVQLVESGGGLVQPGGSLRLSCAASGFTFSSYAMNWVRQAPGKGLEWVSGISSWGSSTYYADSV
KGRFTISRDNSKNTLYLQMNSLRAEDTAVYYCAREDGSYMTDYFAYWGQGTLVTVSS

3089_VH2 (SEQ ID NO: 23):
QVQLKESGPALVKPTQTLTLTCTFSGFSLSSDGMGVGWIRQPPGKALEWLALIDWDDDKRYSTSLK
TRLTISKDTSKNQVVLTMTNMDPVDTATYYCARFNWFYRLAFVNPDVWGQGTLVTVSS

3101_VH2 (SEQ ID NO: 24):
QVQLKESGPALVKPTQTLTLTCTFSGFSLSTSRVGVSWIRQPPGKALEWLAHIDWNDDKYYSTSLKT
RLTISKDTSKNQVVLTMTNMDPVDTATYYCAREDRLLGGYGYDVWGQGTLVTVSS

Figure 1b (Continued)

3102_VH4 (SEQ ID NO: 25):
QVQLQESGPGLVKPGETLSLTCTVSGGSISGNYWSWIRQAPGKGLEWIGDYHGSTYYNPSLKGRVT
ISVDTSKNQFSLKLSSVTAEDTAVYYCAREQYHWGLAWTGFDNWGQGTLVTVSS

3127_VH5 (SEQ ID NO: 26):
QVQLVQSGAEVKKPGESLKISCKGSGYSFSTSWVGWVRQMPGKGLEWMGIIDPDISYTSYSPSFQG
QVTISADKSISTAYLQWSSLKASDTAMYYCARYLMGLGYDVWGQGTLVTVSS

3128_VH2 (SEQ ID NO: 27):
QVQLKESGPALVKPTQTLTLTCTFSGFSLSSSGMSVSWIRQPPGKALEWLARIYSDDSKSYSTSLKT
RLTISKDTSKNQVVLTMTNMDPVDTATYYCARAAHWNGPLFDVWGQGTLVTVSS

3129_VH3 (SEQ ID NO: 28):
QVQLVESGGGLVQPGGSLRLSCAASGFTFSNYSMNWVRQAPGKGLEWVSYIYGGGSYTYYADSVK
GRFTISRDNSKNTLYLQMNSLRAEDTAVYYCARQAGMYFDVWGQGTLVTVSS

3130_VH4 (SEQ ID NO: 29):
QVQLQESGPGLVKPGETLSLTCTVSGGSIGYYWNWIRQAPGKGLEWIGHISRFGSTNYNPSLKGRV
TISVDTSKNQFSLKLSSVTAEDTAVYYCAREYTGNDWYRQQGQHADYWGQGTLVTVSS

3131_VH2 (SEQ ID NO: 30):
QVQLKESGPALVKPTQTLTLTCTFSGFSLSNSGVGVGWIRQPPGKALEWLADIYSDTTKRYSTSLKT
RLTISKDTSKNQVVLTMTNMDPVDTATYYCARYGEAYFDYWGQGTLVTVSS

6183_VH3 (SEQ ID NO: 92)
QVQLVESGGGLVQPGGSLRLSCAAS<u>GFTFSSYYMN</u>WVRQAPGKGLEWVS<u>GINMESTRIYYADSVK</u>
GRFTISRDNSKNTLYLQMNSLRAEDTAVYYCAR<u>DLPLVYTGFAY</u>WGQGTLVTVSS

6184_VH3 (SEQ ID NO: 93)
QVQLVESGGGLVQPGGSLRLSCAAS<u>GFTFSSYYMN</u>WVRQAPGKGLEWVS<u>AISHDGNVKYYADSVK</u>
GRFTISRDNSKNTLYLQMNSLRAEDTAVYYCAR<u>DLPLVYTGFAY</u>WGQGTLVTVSS

6185_VH3 (SEQ ID NO: 94)
QVQLVESGGGLVQPGGSLRLSCAAS<u>GFTFSSYYMN</u>WVRQAPGKGLEWVS<u>AISMNGDYISYADSVK</u>
GRFTISRDNSKNTLYLQMNSLRAEDTAVYYCAR<u>DLPLVYTGFAY</u>WGQGTLVTVSS

6186_VH3 (SEQ ID NO: 95)
QVQLVESGGGLVQPGGSLRLSCAAS<u>GFTFSSYYMN</u>WVRQAPGKGLEWVS<u>AINLSGSAKYYADSVK</u>
GRFTISRDNSKNTLYLQMNSLRAEDTAVYYCAR<u>DLPLVYTGFAY</u>WGQGTLVTVSS

Figure 1b (Continued)

6187_VH3 (SEQ ID NO: 96)
QVQLVESGGGLVQPGGSLRLSCAAS<u>GFTFSSYYMN</u>WVRQAPGKGLE<u>WVSAISSNGDITYYADSVKG</u>
<u>R</u>FTISRDNSKNTLYLQMNSLRAEDTAVYYCAR<u>DLPLVYTGFAY</u>WGQGTLVTVSS

6188_VH3 (SEQ ID NO: 97)
QVQLVESGGGLVQPGGSLRLSCAAS<u>GFTFSSYYMN</u>WVRQAPGKGLE<u>WVSAISTNGWQTYYADSVK</u>
<u>GR</u>FTISRDNSKNTLYLQMNSLRAEDTAVYYCAR<u>DLPLVYTGFAY</u>WGQGTLVTVSS

6189_VH3 (SEQ ID NO: 98)
QVQLVESGGGLVQPGGSLRLSCAAS<u>GFTFSSYYMN</u>WVRQAPGKGLE<u>WVSAINMIGNVTNYADSVK</u>
<u>GR</u>FTISRDNSKNTLYLQMNSLRAEDTAVYYCAR<u>DLPLVYTGFAY</u>WGQGTLVTVSS

6190_VH3 (SEQ ID NO: 99)
QVQLVESGGGLVQPGGSLRLSCAAS<u>GFTFSSYYMN</u>WVRQAPGKGLE<u>WVSYINPNGMMTNYADSVK</u>
<u>GR</u>FTISRDNSKNTLYLQMNSLRAEDTAVYYCAR<u>DLPLVYTGFAY</u>WGQGTLVTVSS

6192_VH3 (SEQ ID NO: 100)
QVQLVESGGGLVQPGGSLRLSCAAS<u>GFTFSSYYMN</u>WVRQAPGKGLE<u>WVSVISPGGEAKSYADSVK</u>
<u>GR</u>FTISRDNSKNTLYLQMNSLRAEDTAVYYCAR<u>DLPLVYTGFAY</u>WGQGTLVTVSS

6195_VH3 (SEQ ID NO: 101)
QVQLVESGGGLVQPGGSLRLSCAAS<u>GFTFSSYYMN</u>WVRQAPGKGLE<u>WVSAISGNGGHTYYADSVK</u>
<u>GR</u>FTISRDNSKNTLYLQMNSLRAEDTAVYYCAR<u>DLPLVYTGFAY</u>WGQGTLVTVSS

6197_VH3 (SEQ ID NO: 102)
QVQLVESGGGLVQPGGSLRLSCAAS<u>GFTFSSYYMN</u>WVRQAPGKGLE<u>WVSAISMDGVYKYYADSVK</u>
<u>GR</u>FTISRDNSKNTLYLQMNSLRAEDTAVYYCAR<u>DLPLVYTGFAY</u>WGQGTLVTVSS

6200_VH3 (SEQ ID NO: 103)
QVQLVESGGGLVQPGGSLRLSCAAS<u>GFTFSSYYMN</u>WVRQAPGKGLE<u>WVSAISNNGNVTYYADSVK</u>
<u>GR</u>FTISRDNSKNTLYLQMNSLRAEDTAVYYCAR<u>DLPLVYTGFAY</u>WGQGTLVTVSS

6201_VH3 (SEQ ID NO: 104)
QVQLVESGGGLVQPGGSLRLSCAAS<u>GFTFSSYYMN</u>WVRQAPGKGLE<u>WVSAISMHGDTTYYADSVK</u>
<u>GR</u>FTISRDNSKNTLYLQMNSLRAEDTAVYYCAR<u>DLPLVYTGFAY</u>WGQGTLVTVSS

6204_VH3 (SEQ ID NO: 105)
QVQLVESGGGLVQPGGSLRLSCAAS<u>GFTFSSYAMN</u>WVRQAPGKGLE<u>WVSHIRKKNTSYTTEYAAS</u>
<u>VKGR</u>FTISRDNSKNTLYLQMNSLRAEDTAVYYCAR<u>EDGSYMTDYFAY</u>WGQGTLVTVSS

Figure 1b (Continued)

6214_VH3 (SEQ ID NO: 106)
QVQLVESGGGLVQPGGSLRLSCAAS<u>GFTFSSYAMN</u>WVRQAPGKGLEWVS<u>NIQRVGSTYYADSVKG</u>
<u>R</u>FTISRDNSKNTLYLQMNSLRAEDTAVYYCAR<u>EDGSYMTDYFAY</u>WGQGTLVTVSS

3077_VH1B (SEQ ID NO: 114)
QVQLVQSGAEVKKPGASVKVSCKASGYTFTSYSINWVRQAPGQGLEWMGYIDPNRGNTNYAQKFQ
GRVTMTRDTSISTAYMELSSLRSEDTAVYYCAREYIYFIHGMLDFWGQGTLVTVSS

3079_VH3 (SEQ ID NO: 115)
QVQLVESGGGLVQPGGSLRLSCAASGFTFSNYGMHWVRQAPGKGLEWVSNIRSDGSWTYYADSV
KGRFTISRDNSKNTLYLQMNSLRAEDTAVYYCARRYWSKSHASVTDYWGQGTLVTVSS

3080_VH3 (SEQ ID NO: 116)
QVQLVESGGGLVQPGGSLRLSCAASGFTFSSYGMHWVRQAPGKGLEWVSNIYSDGSNTFYADSVK
GRFTISRDNSKNTLYLQMNSLRAEDTAVYYCARNMYRWPFHYFFDYWGQGTLVTVSS

Figure 2a

Variable Light Chain DNA

3076_Vl lambda 2 (SEQ ID NO: 31):
GATATCGCACTGACCCAGCCAGCTTCAGTGAGCGGCTCACCAGGTCAGAGCATTACCATCTCGT
GTACGGGTACTAGCAGCGATATTGGTGCTTATGTGTCTTGGTACCAGCAGCATCCCGGGAAGGC
GCCGAAACTTATGATTTATGAGGTTTCTTCTCGTCCCTCAGGCGTGAGCAACCGTTTTAGCGGAT
CCAAAAGCGGCAACACCGCGAGCCTGACCATTAGCGGCCTGCAAGCGGAAGACGAAGCGGATT
ATTATTGCTCTTCTTATGATCTTACTCCTCCTGGTAAGGTGTTTGGCGGCGGCACGAAGTTAACC
GTTCTTGGCCAG

3078_Vl lambda 3 (SEQ ID NO: 32):
GATATCGAACTGACCCAGCCGCCTTCAGTGAGCGTTGCACCAGGTCAGACCGCGCGTATCTCGT
GTAGCGGCGATAATATTGGTCATTATTATGTTTCTTGGTACCAGCAGAAACCCGGGCAGGCGCC
AGTTCTTGTGATTTATGGTGATAATAATCGTCCCTCAGGCATCCCGGAACGCTTTAGCGGATCCA
ACAGCGGCAACACCGCGACCCTGACCATTAGCGGCACTCAGGCGGAAGACGAAGCGGATTATT
ATTGCGCTTCTGATGTTGGTTCTCTTGATGTGTTTGGCGGCGGCACGAAGTTAACCGTTCTTGGC
CAG

3081_ Vk kappa 3 (SEQ ID NO: 33):
GATATCGTGCTGACCCAGAGCCCGGCGACCCTGAGCCTGTCTCCGGGCGAACGTGCGACCCTG
AGCTGCAGAGCGAGCCAGACTGGTTCTACTTCTTATCTGGCTTGGTACCAGCAGAAACCAGGTC
AAGCACCGCGTCTATTAATTTATGATGCTTCTAAGCGTGCAACTGGGGTCCCGGCGCGTTTTAGC
GGCTCTGGATCCGGCACGGATTTTACCCTGACCATTAGCAGCCTGGAACCTGAAGACTTTGCGA
CTTATTATTGCCATCAGTATTATAACGTTCCTCATACCTTTGGCCAGGGTACGAAAGTTGAAATTA
AACGTACG

3085_ Vl lambda 1 (SEQ ID NO: 34):
GATATCGTGCTGACCCAGCCGCCTTCAGTGAGTGGCGCACCAGGTCAGCGTGTGACCATCTCGT
GTAGCGGCAGCAGCAGCAACATTGGTAATAATTATGTGTCTTGGTACCAGCAGTTGCCCGGGAC
GGCGCCGAAACTTCTGATTTATGGTGATGATCAGCGTCCCTCAGGCGTGCCGGATCGTTTTAGC
GGATCCAAAAGCGGCACCAGCGCGAGCCTTGCGATTACGGGCCTGCAAAGCGAAGACGAAGCG
GATTATTATTGCCAGTCTTATGGTACTTTTTCTTCTTTTGTGTTTGGCGGCGGCACGAAGTTAACC
GTTCTTGGCCAG

3086_Vk kappa 1 (SEQ ID NO: 35):
GATATCCAGATGACCCAGAGCCCGTCTAGCCTGAGCGCGAGCGTGGGTGATCGTGTGACCATTA
CCTGCAGAGCGAGCCAGAATATTTCTCAGTGGCTGAATTGGTACCAGCAGAAACCAGGTAAAGC
ACCGAAACTATTAATTTATGGTGCTTCTAATTTGCAAAGCGGGGTCCCGTCCCGTTTTAGCGGCT
CTGGATCCGGCACTGATTTTACCCTGACCATTAGCAGCCTGCAACCTGAAGACTTTGCGACTTAT
TATTGCCAGCAGTATTATGATCTTCCTAATACCTTTGGCCAGGGTACGAAAGTTGAAATTAAACGT
ACG

3087_ Vl lambda 3 (SEQ ID NO: 36):
GATATCGAACTGACCCAGCCGCCTTCAGTGAGCGTTGCACCAGGTCAGACCGCGCGTATCTCGT
GTAGCGGCGATAATCTTCGTCATTATTATGTTTATTGGTACCAGCAGAAACCCGGGCAGGCGCCA
GTTCTTGTGATTTATGGTGATTCTAAGCGTCCCTCAGGCATCCCGGAACGCTTTAGCGGATCCAA
CAGCGGCAACACCGCGACCCTGACCATTAGCGGCACTCAGGCGGAAGACGAAGCGGATTATTA
TTGCCAGACTTATACTGGTGGTGCTTCTCTTGTGTTTGGCGGCGGCACGAAGTTAACCGTTCTTG
GCCAG Figure 2a (Continued)

3088_ Vl lambda 3 (SEQ ID NO: 37):
GATATCGAACTGACCCAGCCGCCTTCAGTGAGCGTTGCACCAGGTCAGACCGCGCGTATCTCGT
GTAGCGGCGATAATATTGGTCATTATTATGTTTCTTGGTACCAGCAGAAACCCGGGCAGGCGCC
AGTTCTTGTGATTTATTCTGATTCTAATCGTCCCTCAGGCATCCCGGAACGCTTTAGCGGATCCA
ACAGCGGCAACACCGCGACCCTGACCATTAGCGGCACTCAGGCGGAAGACGAAGCGGATTATT
ATTGCCAGTCTTATAATGGTACTTATGTGTTTGGCGGCGGCACGAAGTTAACCGTTCTTGGCCAG

3089_ Vk kappa 3 (SEQ ID NO: 38):
GATATCGTGCTGACCCAGAGCCCGGCGACCCTGAGCCTGTCTCCGGGCGAACGTGCGACCCTG
AGCTGCAGAGCGAGCCAGTCTGTTTCTTCTTATCTGGCTTGGTACCAGCAGAAACCAGGTCA
AGCACCGCGTCTATTAATTTATGGTGCTTCTTCTCGTGCAACTGGGGTCCCGGCGCGTTTTAGCG
GCTCTGGATCCGGCACGGATTTTACCCTGACCATTAGCAGCCTGGAACCTGAAGACTTTGCGGT
TTATTATTGCCAGCAGGGTTATAATTCTCCTTTTACCTTTGGCCAGGGTACGAAAGTTGAAATTAA
ACGTACG

3101_ Vl lambda 3 (SEQ ID NO: 39):
GATATCGAACTGACCCAGCCGCCTTCAGTGAGCGTTGCACCAGGTCAGACCGCGCGTATCTCGT
GTAGCGGCGATTCTCTTGGTTCTTATTATGTTCATTGGTACCAGCAGAAACCCGGGCAGGCGCC
AGTTCTTGTGATTGGTGATGATACTAAGCGTCCCTCAGGCATCCCGGAACGCTTTAGCGGATCCA
ACAGCGGCAACACCGCGACCCTGACCATTAGCGGCACTCAGGCGGAAGACGAAGCGGATTATT
ATTGCGGTTCTCGTACTGGTTATAATAATTCTTTTGTGTTTGGCGGCGGCACGAAGTTAACCGTT
CTTGGCCAG

3102_ V'l lambda 3 (SEQ ID NO: 40):
GATATCGAACTGACCCAGCCGCCTTCAGTGAGCGTTGCACCAGGTCAGACCGCGCGTATCTCGT
GTAGCGGCGATAATCTTGGTCATTATTATGTTTCTTGGTACCAGCAGAAACCCGGGCAGGCGCC
AGTTCTTGTGATTTATGATGATTCTGATCGTCCCTCAGGCATCCCGGAACGCTTTAGCGGATCCA
ACAGCGGCAACACCGCGACCCTGACCATTAGCGGCACTCAGGCGGAAGACGAAGCGGATTATT
ATTGCGGTGCTTATGCTATGCATATGACTGTGTTTGGCGGCGGCACGAAGTTAACCGTTCTTGGC
CAG

3127_ Vl lambda 2 (SEQ ID NO: 41):
GATATCGCACTGACCCAGCCAGCTTCAGTGAGCGGCTCACCAGGTCAGAGCATTACCATCTCGT
GTACGGGTACTAGCAGCGATGTTGGTGCTATTAATTATGTGTCTTGGTACCAGCAGCATCCCGG
GAAGGCGCCGAAACTTATGATTTATGATGTTAATAAGCGTCCCTCAGGCGTGCCGGATCGTTTTA
GCGGATCCAAAAGCGGCAACACCGCGAGCCTGACCATTAGCGGCCTGCAAGCGGAAGACGAAG
CGGATTATTATTGCGGTTCTTATACTATGCAGGTTGGTTCTTATGTGTTTGGCGGCGGCACGAAG
TTAACCGTTCTTGGCCAG

3128_ Vl lambda 3 (SEQ ID NO: 42):
GATATCGAACTGACCCAGCCGCCTTCAGTGAGCGTTGCACCAGGTCAGACCGCGCGTATCTCGT
GTAGCGGCGATAATATTGGTCATTATTATGCTCATTGGTACCAGCAGAAACCCGGGCAGGCGCC
AGTTGTTGTGATTTATGATGATAATGATCGTCCCTCAGGCATCCCGGAACGCTTTAGCGGATCCA
ACAGCGGCAACACCGCGACCCTGACCATTAGCGGCACTCAGGCGGAAGACGAAGCGGATTATT
ATTGCCAGGCTTATACTGGTGATGGTGGTCGTGTGTTTGGCGGCGGCACGAAGTTAACCGTTCT
TGGCCAG

Figure 2a (Continued)

3129_ Vl lambda 3 (SEQ ID NO: 43):
GATATCGAACTGACCCAGCCGCCTTCAGTGAGCGTTGCACCAGGTCAGACCGCGCGTATCTCGT
GTAGCGGCGATAATCTTGGTTCTAAGGTTGTTTCTTGGTACCAGCAGAAACCCGGGCAGGCGCC
AGTTCTTGTGATTTATTATGATAATAAGCGTCCCTCAGGCATCCCGGAACGCTTTAGCGGATCCA
ACAGCGGCAACACCGCGACCCTGACCATTAGCGGCACTCAGGCGGAAGACGAAGCGGATTATT
ATTGCCAGTCTTATACTTTTGAGTCTGGTTCTGTTGTGTTTGGCGGCGGCACGAAGTTAACCGTT
CTTGGCCAG

3130_ Vl lambda 3 (SEQ ID NO: 44):
GATATCGAACTGACCCAGCCGCCTTCAGTGAGCGTTGCACCAGGTCAGACCGCGCGTATCTCGT
GTAGCGGCGATAATCTTGGTCATTATTATGTTGATTGGTACCAGCAGAAACCCGGGCAGGCGCC
AGTTCTTGTGATTTATGCTGATAATAATCGTCCCTCAGGCATCCCGGAACGCTTTAGCGGATCCA
ACAGCGGCAACACCGCGACCCTGACCATTAGCGGCACTCAGGCGGAAGACGAAGCGGATTATT
ATTGCTCTTCTTATTCTCAGCAGTCTATGGTGTTTGGCGGCGGCACGAAGTTAACCGTTCTTGGC
CAG

3131_ Vl lambda 3 (SEQ ID NO: 45):
GATATCGAACTGACCCAGCCGCCTTCAGTGAGCGTTGCACCAGGTCAGACCGCGCGTATCTCGT
GTAGCGGCGATAATCTTGGTAATTTTTATGTTCATTGGTACCAGCAGAAACCCGGGCAGGCGCC
AGTTCTTGTGATTTATGAGGATTCTAATCGTCCCTCAGGCATCCCGGAACGCTTTAGCGGATCCA
ACAGCGGCAACACCGCGACCCTGACCATTAGCGGCACTCAGGCGGAAGACGAAGCGGATTATT
ATTGCTCTTCTTGGGATATGTATCGTACTATTTTTGTGTTTGGCGGCGGCACGAAGTTAACCGTTC
TTGGCCAG

6278_Vl lambda 3 (SEQ ID NO: 107)
GATATCGAACTGACCCAGCCGCCTTCAGTGAGCGTTGCACCAGGTCAGACCGCGCGTATCTCGT
GTAGCGGCGATAATATTGGTCATTATTATGTTTGGTACCAGCAGAAACCCGGGCAGGCGCC
AGTTCTTGTGATTTATTCTGATTCTAATCGTCCCTCAGGCATCCCGGAACGCTTTAGCGGATCCA
ACAGCGGCAACACCGCGACCCTGACCATTAGCGGCACTCAGGCGGAAGACGAAGCGGATTATT
ATTGCCAGTCTGCTGATAATTTTCCTTTTGTGTTTGGCGGCGGCACGAAGTTAACCGTCCTAGGT
CAG

6279_ Vl lambda 3 (SEQ ID NO: 108)
GATATCGAACTGACCCAGCCGCCTTCAGTGAGCGTTGCACCAGGTCAGACCGCGCGTATCTCGT
GTAGCGGCGATAATATTGGTCATTATTATGTTTCTTGGTACCAGCAGAAACCCGGGCAGGCGCC
AGTTCTTGTGATTTATTCTGATTCTAATCGTCCCTCAGGCATCCCGGAACGCTTTAGCGGATCCA
ACAGCGGCAACACCGCGACCCTGACCATTAGCGGCACTCAGGCGGAAGACGAAGCGGATTATT
ATTGCCAGTCTTATACTATGTCTGATGTTCTTGTTGTGTTTGGCGGCGGCACGAAGTTAACCGTC
CTAGGTCAG

3077_Vk kappa 2 (SEQ ID NO: 117)
GATATCGTGATGACCCAGAGCCCACTGAGCCTGCCAGTGACTCCGGGCGAGCCTGCGAGCATT
AGCTGCAGAAGCAGCCAAAGCCTGCTTTTTATTGATGGCAATAATTATCTGAATTGGTACCTTCAA
AAACCAGGTCAAAGCCCGCAGCTATTAATTTATCTTGGTTCTAATCGTGCCAGTGGGGTCCCGGA
TCGTTTTAGCGGCTCTGGATCCGGCACCGATTTTACCCTGAAAATTAGCCGTGTGGAAGCTGAA
GACGTGGGCGTGTATTATTGCCAGCAGTATTCTTCTAAGTCTGCTACCTTTGGCCAGGGTACGAA
AGTTGAAATTAAACGTACG Figure 2a (Continued)

3079_Vk kappa 1 (SEQ ID NO: 118)
GATATCCAGATGACCCAGAGCCCGTCTAGCCTGAGCGCGAGCGTGGGTGATCGTGTGACCATTA
CCTGCAGAGCGAGCCAGGATATTTCTGCTTTTCTGAATTGGTACCAGCAGAAACCAGGTAAAGCA
CCGAAACTATTAATTTATAAGGTTTCTAATTTGCAAAGCGGGGTCCCGTCCCGTTTTAGCGGCTC
TGGATCCGGCACTGATTTTACCCTGACCATTAGCAGCCTGCAACCTGAAGACTTTGCGACTTATT
ATTGCCAGCAGGCTTATTCTGGTTCTATTACCTTTGGCCAGGGTACGAAAGTTGAAATTAAACGT
ACG

3080_Vl lambda 3 (SEQ ID NO: 119)
GATATCGAACTGACCCAGCCGCCTTCAGTGAGCGTTGCACCAGGTCAGACCGCGCGTATCTCGT
GTAGCGGCGATAATATTGGTAATAAGTATGTTTCTTGGTACCAGCAGAAACCCGGGCAGGCGCC
AGTTGTTGTGATTTATGGTGATAATAATCGTCCCTCAGGCATCCCGGAACGCTTTAGCGGATCCA
ACAGCGGCAACACCGCGACCCTGACCATTAGCGGCACTCAGGCGGAAGACGAAGCGGATTATT
ATTGCTCTTCTTATGATTCTTCTTATTTTGTGTTTGGCGGCGGCACGAAGTTAACCGTTCTTGGCC
AG

Figure 2b

Variable Light Chain Peptide (CDR Regions in Bold or <u>underlined</u>)

3076_Vl lambda 2 (SEQ ID NO: 46):
DIALTQPASVSGSPGQSITISCTGTSSDIGAYVSWYQQHPGKAPKLMIYEVSSRPSGVSNRFSGSKSG
NTASLTISGLQAEDEADYYCSSYDLTPPGKVFGGGTKLTVLGQ

3078_Vl lambda 3 (SEQ ID NO: 47):
DIELTQPPSVSVAPGQTARISCSGDNIGHYYVSWYQQKPGQAPVLVIYGDNNRPSGIPERFSGSNSG
NTATLTISGTQAEDEADYYCASDVGSLDVFGGGTKLTVLGQ

3081_ Vk kappa 3 (SEQ ID NO: 48):
DIVLTQSPATLSLSPGERATLSCRASQTGSTSYLAWYQQKPGQAPRLLIYDASKRATGVPARFSGSG
SGTDFTLTISSLEPEDFATYYCHQYYNVPHTFGQGTKVEIKRT

3085_ Vl lambda 1 (SEQ ID NO: 49):
DIVLTQPPSVSGAPGQRVTISCSGSSSNIGNNYVSWYQQLPGTAPKLLIYGDDQRPSGVPDRFSGSK
SGTSASLAITGLQSEDEADYYCQSYGTFSSFVFGGGTKLTVLGQ

3086_Vk kappa 1 (SEQ ID NO: 50):
DIQMTQSPSSLSASVGDRVTITCRASQNISQWLNWYQQKPGKAPKLLIYGASNLQSGVPSRFSGSG
SGTDFTLTISSLQPEDFATYYCQQYYDLPNTFGQGTKVEIKRT

3087_ Vl lambda 3 (SEQ ID NO: 51):
DIELTQPPSVSVAPGQTARISCSGDNLRHYYVYWYQQKPGQAPVLVIYGDSKRPSGIPERFSGSNSG
NTATLTISGTQAEDEADYYCQTYTGGASLVFGGGTKLTVLGQ

3088_ Vl lambda 3 (SEQ ID NO: 52):
DIELTQPPSVSVAPGQTARISCSGDNIGHYYVSWYQQKPGQAPVLVIYSDSNRPSGIPERFSGSNSG
NTATLTISGTQAEDEADYYCQSYNGTYVFGGGTKLTVLGQ

3089_ Vk kappa 3 (SEQ ID NO: 53):
DIVLTQSPATLSLSPGERATLSCRASQSVSSSYLAWYQQKPGQAPRLLIYGASSRATGVPARFSGSG
SGTDFTLTISSLEPEDFAVYYCQQGYNSPFTFGQGTKVEIKRT

3101_ Vl lambda 3 (SEQ ID NO: 54):
DIELTQPPSVSVAPGQTARISCSGDSLGSYYVHWYQQKPGQAPVLVIGDDTKRPSGIPERFSGSNSG
NTATLTISGTQAEDEADYYCGSRTGYNNSFVFGGGTKLTVLGQ

3102_ Vl lambda 3 (SEQ ID NO: 55):
DIELTQPPSVSVAPGQTARISCSGDNLGHYYVSWYQQKPGQAPVLVIYDDSDRPSGIPERFSGSNSG
NTATLTISGTQAEDEADYYCGAYAMHMTVFGGGTKLTVLGQ

3127_ Vl lambda 2 (SEQ ID NO: 56):
DIALTQPASVSGSPGQSITISCTGTSSDVGAINYVSWYQQHPGKAPKLMIYDVNKRPSGVPDRFSGS
KSGNTASLTISGLQAEDEADYYCGSYTMQVGSYVFGGGTKLTVLGQ Figure 2b (Continued)

3128_ Vl lambda 3 (SEQ ID NO: 57):
DIELTQPPSVSVAPGQTARISCSGDNIGHYYAHWYQQKPGQAPVVVIYDDNDRPSGIPERFSGSNSG
NTATLTISGTQAEDEADYYCQAYTGDGGRVFGGGTKLTVLGQ

3129_ Vl lambda 3 (SEQ ID NO: 58):
DIELTQPPSVSVAPGQTARISCSGDNLGSKVVSWYQQKPGQAPVLVIYYDNKRPSGIPERFSGSNSG
NTATLTISGTQAEDEADYYCQSYTFESGSVVFGGGTKLTVLGQ

3130_ Vl lambda 3 (SEQ ID NO: 59):
DIELTQPPSVSVAPGQTARISCSGDNLGHYYVDWYQQKPGQAPVLVIYADNNRPSGIPERFSGSNSG
NTATLTISGTQAEDEADYYCSSYSQQSMVFGGGTKLTVLGQ

3131_ Vl lambda 3 (SEQ ID NO: 60):
DIELTQPPSVSVAPGQTARISCSGDNLGNFYVHWYQQKPGQAPVLVIYEDSNRPSGIPERFSGSNSG
NTATLTISGTQAEDEADYYCSSWDMYRTIFVFGGGTKLTVLGQ

6278_ Vl lambda 3 (SEQ ID NO: 109)
DIELTQPPSVSVAPGQTARISCSGDNIGHYYVSWYQQKPGQAPVLVIYSDSNRPSGIPERFSGSNSG
NTATLTISGTQAEDEADYYCQSADNFPFVFGGGTKLTVLGQ

6279_ Vl lambda 3 (SEQ ID NO: 110)
DIELTQPPSVSVAPGQTARISCSGDNIGHYYVSWYQQKPGQAPVLVIYSDSNRPSGIPERFSGSNSG
NTATLTISGTQAEDEADYYCQSYTMSDVLVVFGGGTKLTVLGQ

3077_Vk kappa 2 (SEQ ID NO: 120)
DIVMTQSPLSLPVTPGEPASISCRSSQSLLFIDGNNYLNWYLQKPGQSPQLLIYLGSNRASGVPDRFS
GSGSGTDFTLKISRVEAEDVGVYYCQQYSSKSATFGQGTKVEIKRT

3079_Vk kappa 1 (SEQ ID NO: 121)
DIQMTQSPSSLSASVGDRVTITCRASQDISAFLNWYQQKPGKAPKLLIYKVSNLQSGVPSRFSGSGS
GTDFTLTISSLQPEDFATYYCQQAYSGSITFGQGTKVEIKRT

3080_Vl lambda3 (SEQ ID NO: 122)
DIELTQPPSVSVAPGQTARISCSGDNIGNKYVSWYQQKPGQAPVVVIYGDNNRPSGIPERFSGSNSG
NTATLTISGTQAEDEADYYCSSYDSSYFVFGGGTKLTVLGQ

Figure 3

Variable Heavy Chain Consensus Sequences (CDR Regions in Bold)

VH1A Consensus (SEQ ID NO: 61):
QVQLVQSGAEVKKPGSSVKVSCKASGGTFSSYAISWVRQAPGQGLEWMGGIIPIFGTANYAQKFQGRV
TITADESTSTAYMELSSLRSEDTAVYYCARWGGDGFYAMDYWGQGTLVTVSS

VH2 Consensus (SEQ ID NO: 62)
QVQLKESGPALVKPTQTLTLTCTFSGFSLSTSGVGVGWIRQPPGKALEWLALIDWDDDKYYSTSLKTR
LTISKDTSKNQVVLTMTNMDPVDTATYYCARWGGDGFYAMDYWGQGTLVTVSS

VH3 Consensus (SEQ ID NO: 63):

(1)   QVQLVESGGG LVQPGGSLRL SCAASGFTFS SYAMSWVRQA PGKGLEWVSA
(51)  ISGSGGSTYY ADSVKGRFTI SRDNSKNTLY LQMNSLRAED TAVYYCARWG
(101) GDGFYAMDYW GQGTLVTVS S

VH4 Consensus (SEQ ID NO: 64):
QVQLQESGPGLVKPSETLSLTCTVSGGSISSYYWSWIRQPPGKGLEWIGYIYYSGSTNYNPSLKSRVT
ISVDTSKNQFSLKLSSVTAADTAVYYCARWGGDGFYAMDYWGQGTLVTVSS

VH5 Consensus (SEQ ID NO: 65):
QVQLVQSGAEVKKPGESLKISCKGSGYSFTSYWIGWVRQMPGKGLEWMGIIYPGDSDTRYSPSFQGQV
TISADKSISTAYLQWSSLKASDTAMYYCARWGGDGFYAMDYWGQGTLVTVSS

Figure 4

Variable Light Chain Consensus Sequences (CDR Regions in Bold)

Vl_λ1 Consensus (SEQ ID NO: 66):
DIVLTQPPSVSGAPGQRVTISCSGSSSNIGSNYVSWYQQLPGTAPKLLIYDNNQRPSGVPDRFSGSKS
GTSASLAITGLQSEDEADYYCQQHYTTPPVFGGGTKLTVLGQ

Vl_λ2 Consensus (SEQ ID NO: 67):
DIALTQPASVSGSPGQSITISCTGTSSDVGGYNYVSWYQQHPGKAPKLMIYDVSNRPSGVSNRFSGSK
SGNTASLTISGLQAEDEADYYCQQHYTTPPVFGGGTKLTVLGQ

Vl_λ3 Consensus (SEQ ID NO: 68):

(1)   DIELTQPPSV SVAPGQTARI SCSGDALGDK YASWYQQKPG QAPVLVIYDD
(51)  SDRPSGIPER FSGSNSGNTA TLTISGTQAE DEADYYCQQ YTTPPVFGGG
(101) TKLTVLG

Vl_k1 Consensus (SEQ ID NO: 69):

(1)   DIQMTQSPSS LSASVGDRVT ITCRASQGIS SYLAWYQQKP GKAPKLLIYA
(51)  ASSLQSGVPS RFSGSGSGTD FTLTISSLQP EDFATYYCQQ HYTTPPTFGQ
(101) GTKVEIKR

Vl_k3 Consensus (SEQ ID NO: 70):
DIVLTQSPATLSLSPGERATLSCRASQSVSSSYLAWYQQKPGQAPRLLIYGASSRATGVPARFSGSGS
GTDFTLTISSLEPEDFAVYYCQQHYTTPPTFGQGTKVEIKRT

Figure 5

Peptide Sequence of CD38

(SEQ ID NO: 71):

```
1    mancefspvs gdkpccrlsr raqlclgvsi lvlilvvvla vvvprwrqqw sgpgttkrfp 61   etvlarcvky teihpemrhv dcqsvwdafk gafiskhpcn iteedyqplm klgtqtvpcn 121  killwsrikd lahqftqvqr dmftledtll gyladdltwc gefntskiny qscpdwrkdc 181  snnpvsvfwk tvsrrfaeaa cdvvhvmlng srskifdkns tfgsvevhnl qpekvqtlea 241  wvihggreds rdlcqdptik elesiiskrn iqfsckniyr pdkflqcvkn pedssctsei
```

Figure 6

Nucleotide Sequence of Chimeric OKT10

Heavy Chain (SEQ ID NO: 72):

```
caggtggaat tggtggaatc tggaggatcc ctgaaactct cctgtgcagc ctcaggattc
gattttagta gatcctggat gaattgggtc cggcaggctc caggaaaagg gctagaatgg
attggagaaa ttaatccaga tagcagtacg ataaactata cgacatctct aaaggataaa
ttcatcatct ccagagacaa cgccaaaaat acgctgtacc tgcaaatgac caaagtgaga
tctgaggaca cagccctttta ttactgtgca agatatggta actggtttcc ttattgggc
caagggactc tggtcactgt cagctcagcc tccaccaagg gtccatcggt cttccccctg
gcaccctcct ccaagagcac ctctgggggc acagcggccc tgggctgcct ggtcaaggac
tacttccccg aaccggtgac ggtgtcgtgg aactcaggcg ccctgaccag cggcgtgcac
accttcccgg ctgtcctaca gtcctcagga ctctactccc tcagcagcgt ggtgaccgtg
ccctccagca gcttgggcac ccagacctac atctgcaacg tgaatcacaa gcccagcaac
accaaggtgg acaagaaagt tgagcccaaa tcttgtgaca aaactcacac atgcccaccg
tgcccagcac ctgaactcct ggggggaccg tcagtcttcc tcttcccccc aaaacccaag
gacaccctca tgatctcccg gacccctgag gtcacatgcg tggtggtgga cgtgagccac
gaagaccctg aggtcaagtt caactggtac gtggacggcg tggaggtgca taatgccaag
acaaagccgc gggaggagca gtacaacagc acgtaccggg tggtcagcgt cctcaccgtc
ctgcaccagg actggctgaa tggcaaggag tacaagtgca aggtctccaa caaagccctc
ccagccccca tcgagaaaac catctccaaa gccaagggc agccccgaga accacaggtg
tacaccctgc cccatcccg ggatgagctg accaagaacc aggtcagcct gacctgcctg
gtcaaaggct tctatcccag cgacatcgcc gtggagtggg agagcaatgg gcagccggag
aacaactaca agaccacgcc tcccgtgctg gactccgacg gctccttctt cctctacagc
aagctcaccg tggacaagag caggtggcag caggggaacg tcttctcatg ctccgtgatg
catgaggctc tgcacaacca ctacacgcag aagagcctct ccctgtctcc gggtaaa
```

Figure 6 (Continued)

Light Chain (SEQ ID NO: 73):

```
gatatcctga tgacccagtc tcaaaaaatc atgcccacat cagtgggaga cagggtcagc
gtcacctgca aggccagtca aaatgtggat actaatgtag cctggtatca acagaaacca
ggacagtctc ctaaagcact gatttactcg gcatcctacc gatacagtgg agtccctgat
cgcttcacag gcagtggatc tgggacagat ttcactctca ccatcaccaa tgtgcagtct
gaggacttgg cagagtattt ctgtcagcaa tatgacagct atcctctcac gttcggtgct
gggaccaagc tggacctgaa acgtacggtg gctgcaccat ctgtcttcat cttcccgcca
tctgatgagc agttgaaatc tggaactgcc tctgttgtgt gcctgctgaa taacttctat
cccagagagg ccaaagtaca gtggaaggtg gataacgccc tccaatcggg taactcccag
gagagtgtca cagagcagga cagcaaggac agcacctaca gcctcagcag caccctgacg
ctgagcaaag cagactacga gaaacacaaa gtctacgcct gcgaagtcac ccatcagggc
ctgagctcgc ccgtcacaaa gagcttcaac aggggagagt gt
```

Figure 7: DNA sequence of pMOPRH®_h_IgG1_1

```
              StyI
              ~~~~~~~
   601  TCGCTATTAC CATGGTGATG CGGTTTTGGC AGTACATCAA TGGGCGTGGA
        AGCGATAATG GTACCACTAC GCCAAAACCG TCATGTAGTT ACCCGCACCT

AatII
                                                      ~~~~~~
   651  TAGCGGTTTG ACTCACGGGG ATTTCCAAGT CTCCACCCCA TTGACGTCAA
        ATCGCCAAAC TGAGTGCCCC TAAAGGTTCA GAGGTGGGGT AACTGCAGTT

701  TGGGAGTTTG TTTTGGCACC AAAATCAACG GGACTTTCCA AAATGTCGTA
        ACCCTCAAAC AAAACCGTGG TTTTAGTTGC CCTGAAAGGT TTTACAGCAT

751  ACAACTCCGC CCCATTGACG CAAATGGGCG GTAGGCGTGT ACGGTGGGAG
        TGTTGAGGCG GGGTAACTGC GTTTACCCGC CATCCGCACA TGCCACCCTC

801  GTCTATATAA GCAGAGCTCT CTGGCTAACT AGAGAACCCA CTGCTTACTG
        CAGATATATT CGTCTCGAGA GACCGATTGA TCTCTTGGGT GACGAATGAC pMORPH®_Ig_FOR 100.0%                NheI
                   ~~~~~~~~~~~~~~~~~~~~                 ~~~~~~
   851  GCTTATCGAA ATTAATACGA CTCACTATAG GGAGACCCAA GCTGGCTAGC
        CGAATAGCTT TAATTATGCT GAGTGATATC CCTCTGGGTT CGACCGATCG

M   K   H   L   W   F   F   L   L   V   A   P   R  ·
   901  GCCACCATGA AACACCTGTG GTTCTTCCTC CTGCTGGTGG CAGCTCCCAG
        CGGTGGTACT TTGTGGACAC CAAGAAGGAG GACGACCACC GTCGAGGGTC

EcoRI               BlpI            StyI
                               ~~~~~~              ~~~~~~~~        ~
                                                               A   S   T  ·
        ·  W   V   L   S   Q   V   E   F   C   R   R   L   A   Q
   951  ATGGGTCCTG TCCCAGGTGG AATTCTGCAG GCGGTTAGCT CAGCCTCCAC
        TACCCAGGAC AGGGTCCACC TTAAGACGTC CGCCAATCGA GTCGGAGGTG

StyI         BbsI
        ~~~~~        ~~~~~~
        ·  K   G   P   S   V   F   P   L   A   P   S   S   K   S   T   S   G   ·
  1001  CAAGGGTCCA TCGGTCTTCC CCCTGGCACC CTCCTCCAAG AGCACCTCTG
        GTTCCCAGGT AGCCAGAAGG GGGACCGTGG GAGGAGGTTC TCGTGGAGAC

·  G   T   A   A   L   G   C   L   V   K   D   Y   F   P   E   P
  1051  GGGCACAGC GGCCCTGGGC TGCCTGGTCA AGGACTACTT CCCCGAACCG
        CCCCGTGTCG CCGGGACCCG ACGGACCAGT TCCTGATGAA GGGGCTTGGC
```

Figure 7 (Continued)

```
         V  T  V  S    W  N  S    G  A  L    T  S  G    V  H  T  F·
1101   GTGACGGTGT CGTGGAACTC AGGCGCCCTG ACCAGCGGCG TGCACACCTT
       CACTGCCACA GCACCTTGAG TCCGCGGGAC TGGTCGCCGC ACGTGTGGAA

·P  A  V    L  Q  S  S    G  L  Y    S  L  S    S  V  V  T·
1151   CCCGGCTGTC CTACAGTCCT CAGGACTCTA CTCCCTCAGC AGCGTGGTGA
       GGGCCGACAG GATGTCAGGA GTCCTGAGAT GAGGGAGTCG TCGCACCACT

·V  P  S    S  S  L    G  T  Q  T    Y  I  C    N  V  N
1201   CCGTGCCCTC AGCAGCTTG  GGCACCCAGA CCTACATCTG CAACGTGAAT
       GGCACGGGAG TCGTCGAAC  CCGTGGGTCT GGATGTAGAC GTTGCACTTA

StyI
                            ~~~~~~~
        H  K  P  S    N  T  K    V  D  K    K  V  E    P  K  S  C·
1251   CACAAGCCCA GCAACACCAA GGTGGACAAG AAAGTTGAGC CCAAATCTTG
       GTGTTCGGGT CGTTGTGGTT CCACCTGTTC TTTCAACTCG GGTTTAGAAC

·D  K  T    H  T  C  P    P  C  P    A  P  E    L  L  G  G·
1301   TGACAAAACT CACACATGCC CACCGTGCCC AGCACCTGAA CTCCTGGGGG
       ACTGTTTTGA GTGTGTACGG GTGGCACGGG TCGTGGACTT GAGGACCCCC

BbsI                            StyI
            ~~~~~~~                         ~~~~~~
       ·  P  S  V    F  L  F    P  P  K  P    K  D  T    L  M  I
1351   GACCGTCAGT CTTCCTCTTC CCCCCAAAAC CCAAGGACAC CCTCATGATC
       CTGGCAGTCA GAAGGAGAAG GGGGGTTTTG GGTTCCTGTG GGAGTACTAG

BbsI
                                                             ~~~~~
        S  R  T  P    E  V  T    C  V  V    V  D  V  S    H  E  D·
1401   TCCCGGACCC CTGAGGTCAC ATGCGTGGTG GTGGACGTGA GCCACGAAGA
       AGGGCCTGGG GACTCCAGTG TACGCACCAC CACCTGCACT CGGTGCTTCT

BbsI
       ~
       ·P  E  V    K  F  N  W    Y  V  D    G  V  E    V  H  N  A·
1451   CCCTGAGGTC AAGTTCAACT GGTACGTGGA CGGCGTGGAG GTGCATAATG
       GGGACTCCAG TTCAAGTTGA CCATGCACCT GCCGCACCTC CACGTATTAC

·  K  T  K    P  R  E    E  Q  Y  N    S  T  Y    R  V  V
1501   CCAAGACAAA GCCGCGGGAG GAGCAGTACA ACAGCACGTA CCGGGTGGTC
       GGTTCTGTTT CGGCGCCCTC CTCGTCATGT TGTCGTGCAT GGCCCACCAG

S  V  L  T    V  L  H    Q  D  W    L  N  G  K    E  Y  K·
1551   AGCGTCCTCA CCGTCCTGCA CCAGGACTGG CTGAATGGCA AGGAGTACAA
       TCGCAGGAGT GGCAGGACGT GGTCCTGACC GACTTACCGT TCCTCATGTT

·C  K  V    S  N  K  A    L  P  A    P  I  E    K  T  I  S·
1601   GTGCAAGGTC TCCAACAAAG CCCTCCCAGC CCCCATCGAG AAAACCATCT
       CACGTTCCAG AGGTTGTTTC GGGAGGGTCG GGGGTAGCTC TTTTGGTAGA

BsrGI
                                                  ~~~~~~
```

Figure 7 (Continued)

```
            · K   A   K       G   Q   P       R   E   P       Q   V   Y   T       L   P   P
1651       CCAAAGCCAA AGGGCAGCCC CGAGAACCAC AGGTGTACAC CCTGCCCCCA
           GGTTTCGGTT TCCCGTCGGG GCTCTTGGTG TCCACATGTG GGACGGGGGT
              S   R   D   E       L   T   K       N   Q   V       S   L   T   C       L   V   K ·
1701       TCCCGGGATG AGCTGACCAA GAACCAGGTC AGCCTGACCT GCCTGGTCAA
           AGGGCCCTAC TCGACTGGTT CTTGGTCCAG TCGGACTGGA CGGACCAGTT

· G   F   Y       P   S   D   I       A   V   E       W   E   S       N   G   Q   P ·
1751       AGGCTTCTAT CCAGCGACA TCGCCGTGGA GTGGGAGAGC AATGGGCAGC
           TCCGAAGATA GGGTCGCTGT AGCGGCACCT CACCCTCTCG TTACCCGTCG

· E   N   N       Y   K   T       T   P   P       V   L   D   S       D   G   S
1801       CGGAGAACAA CTACAAGACC ACGCCTCCCG TGCTGGACTC CGACGGCTCC
           GCCTCTTGTT GATGTTCTGG TGCGGAGGGC ACGACCTGAG GCTGCCGAGG

F   F   L   Y       S   K   L       T   V   D       K   S   R   W       Q   Q   G ·
1851       TTCTTCCTCT ACAGCAAGCT CACCGTGGAC AAGAGCAGGT GGCAGCAGGG
           AAGAAGGAGA TGTCGTTCGA GTGGCACCTG TTCTCGTCCA CCGTCGTCCC

BbsI                      NsiI
              ~~~~~~~                   ~~~~~~
            · N   V   F       S   C   S   V       M   H   E       A   L   H       N   H   Y   T ·
1901       GAACGTCTTC TCATGCTCCG TGATGCATGA GGCTCTGCAC AACCACTACA
           CTTGCAGAAG AGTACGAGGC ACTACGTACT CCGAGACGTG TTGGTGATGT

SapI                                            PmeI
              ~~~~~~~~                                        ~~~~~~~~
            · Q   K   S       L   S   L       S   P   G   K       *
1951       CGCAGAAGAG CCTCTCCCTG TCTCCGGGTA ATGAGGGCC CGTTTAAACC
           GCGTCTTCTC GGAGAGGGAC AGAGGCCCAT TTACTCCCGG GCAAATTTGG

2001       CGCTGATCAG CCTCGACTGT GCCTTCTAGT TGCCAGCCAT CTGTTGTTTG
           GCGACTAGTC GGAGCTGACA CGGAAGATCA ACGGTCGGTA GACAACAAAC

~~~~~~~~~~~~~~~~~~~~
                      pMORPH®_Ig_REV 100.0%
2051       CCCCTCCCCC GTGCCTTCCT TGACCCTGGA AGGTGCCACT CCCACTGTCC
           GGGGAGGGGG CACGGAAGGA ACTGGGACCT TCCACGGTGA GGGTGACAGG
```

Figure 8: DNA Sequence of Ig kappa light chain expression vector pMORPH®_h_Igκ_1

```
              StyI
              ~~~~~~~
 601   TCGCTATTAC CATGGTGATG CGGTTTTGGC AGTACATCAA TGGGCGTGGA
       AGCGATAATG GTACCACTAC GCCAAAACCG TCATGTAGTT ACCCGCACCT

651   TAGCGGTTTG ACTCACGGGG ATTTCCAAGT CTCCACCCCA TTGACGTCAA
       ATCGCCAAAC TGAGTGCCCC TAAAGGTTCA GAGGTGGGGT AACTGCAGTT

701   TGGGAGTTTG TTTTGGCACC AAAATCAACG GGACTTTCCA AAATGTCGTA
       ACCCTCAAAC AAAACCGTGG TTTTAGTTGC CCTGAAAGGT TTTACAGCAT

751   ACAACTCCGC CCCATTGACG CAAATGGGCG GTAGGCGTGT ACGGTGGGAG
       TGTTGAGGCG GGGTAACTGC GTTTACCCGC CATCCGCACA TGCCACCCTC

801   GTCTATATAA GCAGAGCTCT CTGGCTAACT AGAGAACCCA CTGCTTACTG
       CAGATATATT CGTCTCGAGA GACCGATTGA TCTCTTGGGT GACGAATGAC pMORPH®_Ig_FOR 100%                   NheI
              ========================              ~~~~~~
 851   GCTTATCGAA ATTAATACGA CTCACTATAG GGAGACCCAA GCTGGCTAGC
       CGAATAGCTT TAATTATGCT GAGTGATATC CCTCTGGGTT CGACCGATCG

+1        M   V   L   Q   T   Q   V   F   I   S   L   L   L   W   I
          StyI
          ~~~~~~
 901   GCCACCATGG TGTTGCAGAC CCAGGTCTTC ATTTCTCTGT TGCTCTGGAT
       CGGTGGTACC ACAACGTCTG GGTCCAGAAG TAAAGAGACA ACGAGACCTA
                                                BbsI
                                                ~~~~~~

+1   S   G   A   Y   G   D   I   V   M   I   K   R   T   V   A   A
                          EcoRV             BsiWI
                          ~~~~~~            ~~~~~~
 951   CTCTGGTGCC TACGGGGATA TCGTGATGAT TAAACGTACG GTGGCTGCAC
       GAGACCACGG ATGCCCCTAT AGCACTACTA ATTTGCATGC CACCGACGTG

+1 P   S   V   F   I   F   P   P   S   D   E   Q   L   K   S   G   T
1001   CATCTGTCTT CATCTTCCCG CCATCTGATG AGCAGTTGAA ATCTGGAACT
       GTAGACAGAA GTAGAAGGGC GGTAGACTAC TCGTCAACTT TAGACCTTGA
          BbsI
          ~~~~~~
```

Figure 8 (Continued)

```
     +1    A   S   V   V   C   L   L   N   N   F   Y   P   R   E   A   K   V
    1051  GCCTCTGTTG TGTGCCTGCT GAATAACTTC TATCCCAGAG AGGCCAAAGT
          CGGAGACAAC ACACGGACGA CTTATTGAAG ATAGGGTCTC TCCGGTTTCA

+1    Q   W   K   V   D   N   A   L   Q   S   G   N   S   Q   E   S
    1101  ACAGTGGAAG GTGGATAACG CCCTCCAATC GGGTAACTCC CAGGAGAGTG
          TGTCACCTTC CACCTATTGC GGGAGGTTAG CCCATTGAGG GTCCTCTCAC

+1  V   T   E   Q   D   S   K   D   S   T   Y   S   L   S   S   T   L
    1151  TCACAGAGCA GGACAGCAAG GACAGCACCT ACAGCCTCAG CAGCACCCTG
          AGTGTCTCGT CCTGTCGTTC CTGTCGTGGA TGTCGGAGTC GTCGTGGGAC

+1    T   L   S   K   A   D   Y   E   K   H   K   V   Y   A   C   E   V
                                  BlpI
                                  ~~~~~~~
    1201  ACGCTGAGCA AAGCAGACTA CGAGAAACAC AAAGTCTACG CCTGCGAAGT
          TGCGACTCGT TTCGTCTGAT GCTCTTTGTG TTTCAGATGC GGACGCTTCA

+1    T   H   Q   G   L   S   S   P   V   T   K   S   F   N   R   G
    1251  CACCCATCAG GGCCTGAGCT CGCCCGTCAC AAAGAGCTTC AACAGGGGAG
          GTGGGTAGTC CCGGACTCGA GCGGGCAGTG TTTCTCGAAG TTGTCCCCTC

+1  E   C   *
                                  PmeI                    pMORPH®_Ig_REV 100%
                                  ~~~~~~~~~               ====================
    1301  AGTGTTAGGG GCCCGTTTAA ACCCGCTGAT CAGCCTCGAC TGTGCCTTCT
          TCACAATCCC CGGGCAAATT TGGGCGACTA GTCGGAGCTG ACACGGAAGA

=
    1351  AGTTGCCAGC CATCTGTTGT TTGCCCCTCC CCCGTGCCTT CCTTGACCCT
          TCAACGGTCG GTAGACAACA AACGGGGAGG GGGCACGGAA GGAACTGGGA
```

Figure 9: DNA Sequence of HuCAL® Ig lambda light chain vector pMORPH®_h_Igλ_1

```
               StyI
              ~~~~~~~
  601 TCGCTATTAC CATGGTGATG CGGTTTTGGC AGTACATCAA TGGGCGTGGA
      AGCGATAATG GTACCACTAC GCCAAAACCG TCATGTAGTT ACCCGCACCT

651 TAGCGGTTTG ACTCACGGGG ATTTCCAAGT CTCCACCCCA TTGACGTCAA
      ATCGCCAAAC TGAGTGCCCC TAAAGGTTCA GAGGTGGGGT AACTGCAGTT

701 TGGGAGTTTG TTTTGGCACC AAAATCAACG GGACTTTCCA AAATGTCGTA
      ACCCTCAAAC AAAACCGTGG TTTTAGTTGC CCTGAAAGGT TTTACAGCAT

751 ACAACTCCGC CCCATTGACG CAAATGGGCG GTAGGCGTGT ACGGTGGGAG
      TGTTGAGGCG GGGTAACTGC GTTTACCCGC CATCCGCACA TGCCACCCTC

801 GTCTATATAA GCAGAGCTCT CTGGCTAACT AGAGAACCCA CTGCTTACTG
      CAGATATATT CGTCTCGAGA GACCGATTGA TCTCTTGGGT GACGAATGAC pM_Ig_FOR 100.0%                 NheI
              =========================              ~~~~~~
  851 GCTTATCGAA ATTAATACGA CTCACTATAG GGAGACCCAA GCTGGCTAGC
      CGAATAGCTT TAATTATGCT GAGTGATATC CCTCTGGGTT CGACCGATCG

+1       M  A  W  A  L    L  L  L    T  L  L  T    Q  G  T
         StyI
        ~~~~~~
  901 GCCACCATGG CCTGGGCTCT GCTGCTCCTC ACCCTCCTCA CTCAGGGCAC
      CGGTGGTACC GGACCCGAGA CGACGAGGAG TGGGAGGAGT GAGTCCCGTG

+2                                         T  V    L  G  Q
   +1    G  S  W  A  D  I  V  M  H  E  V
         BamHI      EcoRV           HpaI     StyI
        ~~~~~~     ~~~~~~          ~~~~~~   ~~~~~~
  951 AGGATCCTGG GCTGATATCG TGATGCACGA AGTTAACCGT CCTAGGTCAG
      TCCTAGGACC CGACTATAGC ACTACGTGCT TCAATTGGCA GGATCCAGTC

+2  P  K  A  A  P  S  V  T  L  F  P  P  S  S  E  E  L
         StyI
        ~~~~~~
 1001 CCCAAGGCTG CCCCCTCGGT CACTCTGTTC CCGCCCTCCT CTGAGGAGCT
      GGGTTCCGAC GGGGGAGCCA GTGAGACAAG GGCGGGAGGA GACTCCTCGA

+2  Q  A  N  K  A  T  L  V  C  L  I  S  D  F  Y  P
 1051 TCAAGCCAAC AAGGCCACAC TGGTGTGTCT CATAAGTGAC TTCTACCCGG
      AGTTCGGTTG TTCCGGTGTG ACCACACAGA GTATTCACTG AAGATGGGCC
```

Figure 9 (Continued)

```
     +2 G   A   V   T    V   A   W    K   G   D   S    S   P   V    K   A   G
   1101 GAGCCGTGAC AGTGGCCTGG AAGGGAGATA GCAGCCCCGT CAAGGCGGGA
        CTCGGCACTG TCACCGGACC TTCCCTCTAT CGTCGGGGCA GTTCCGCCCT

+2 V   E   T   T    T   P   S    K   Q   S    N   N   K   Y    A   A   S
   1151 GTGGAGACCA CCACACCCTC CAAACAAAGC AACAACAAGT ACGCGGCCAG
        CACCTCTGGT GGTGTGGGAG GTTTGTTTCG TTGTTGTTCA TGCGCCGGTC

+2  S   Y   L    S   L   T   P    E   Q   W    K   S   H    R   S   Y
   1201 CAGCTATCTG AGCCTGACGC CTGAGCAGTG GAAGTCCCAC AGAAGCTACA
        GTCGATAGAC TCGGACTGCG GACTCGTCAC CTTCAGGGTG TCTTCGATGT

+2 S   C   Q   V    T   H   E    G   S   T   V    E   K   T    V   A   P
                                                           BbsI
                                                          ~~~~~~
   1251 GCTGCCAGGT CACGCATGAA GGGAGCACCG TGGAGAAGAC AGTGGCCCCT
        CGACGGTCCA GTGCGTACTT CCCTCGTGGC ACCTCTTCTG TCACCGGGGA

+2  T   E   C   S   *
                               PmeI
                             ~~~~~~~~
   1301 ACAGAATGTT CATAGGGGCC CGTTTAAACC CGCTGATCAG CCTCGACTGT
        TGTCTTACAA GTATCCCCGG GCAAATTTGG GCGACTAGTC GGAGCTGACA
                                                        pM_Ig_REV 100%
                                                        ==========

1351 GCCTTCTAGT TGCCAGCCAT CTGTTGTTTG CCCCTCCCCC GTGCCTTCCT
        CGGAAGATCA ACGGTCGGTA GACAACAAAC GGGGAGGGGG CACGGAAGGA
        pM_Ig_REV    100.0%
        =========
```

Figure 10

| Designation: | Format | Affinity Maturation | Heavy chain from: | Light chain from: |
|---|---|---|---|---|
| MOR06183 | Fab/IgG1 | new H-CDR2 | MOR06183 | MOR03087 (parental) |
| MOR06184 | Fab/IgG1 | new H-CDR2 | MOR06184 | MOR03087 (parental) |
| MOR06185 | Fab/IgG1 | new H-CDR2 | MOR06185 | MOR03087 (parental) |
| MOR06186 | Fab/IgG1 | new H-CDR2 | MOR06186 | MOR03087 (parental) |
| MOR06187 | Fab/IgG1 | new H-CDR2 | MOR06187 | MOR03087 (parental) |
| MOR06188 | Fab/IgG1 | new H-CDR2 | MOR06188 | MOR03087 (parental) |
| MOR06189 | Fab/IgG1 | new H-CDR2 | MOR06189 | MOR03087 (parental) |
| MOR06190 | Fab/IgG1 | new H-CDR2 | MOR06190 | MOR03087 (parental) |
| MOR06192 | Fab/IgG1 | new H-CDR2 | MOR06192 | MOR03087 (parental) |
| MOR06195 | Fab/IgG1 | new H-CDR2 | MOR06195 | MOR03087 (parental) |
| MOR06197 | Fab/IgG1 | new H-CDR2 | MOR06197 | MOR03087 (parental) |
| MOR06200 | Fab/IgG1 | new H-CDR2 | MOR06200 | MOR03087 (parental) |
| MOR06201 | Fab/IgG1 | new H-CDR2 | MOR06201 | MOR03087 (parental) |
| MOR06204 | Fab/IgG1 | new H-CDR2 | MOR06204 | MOR03088 (parental) |
| MOR06214 | Fab/IgG1 | new H-CDR2 | MOR06214 | MOR03088 (parental) |
| MOR06278 | Fab | new L-CDR3 | MOR03088 (parental) | MOR06278 |
| MOR06279 | Fab | new L-CDR3 | MOR03088 (parental) | MOR06279 |
| MOR06347 | IgG1 | new L-CDR3 | MOR03088 (parental) | MOR06278 |
| MOR06348 | IgG1 | new L-CDR3 & H-CDR2 | MOR06214 | MOR06278 |

FIGURE 11: CD38-expression analysis of Lymphocytes and Erythrocytes
A: MOR 3087
B: MOR 3088
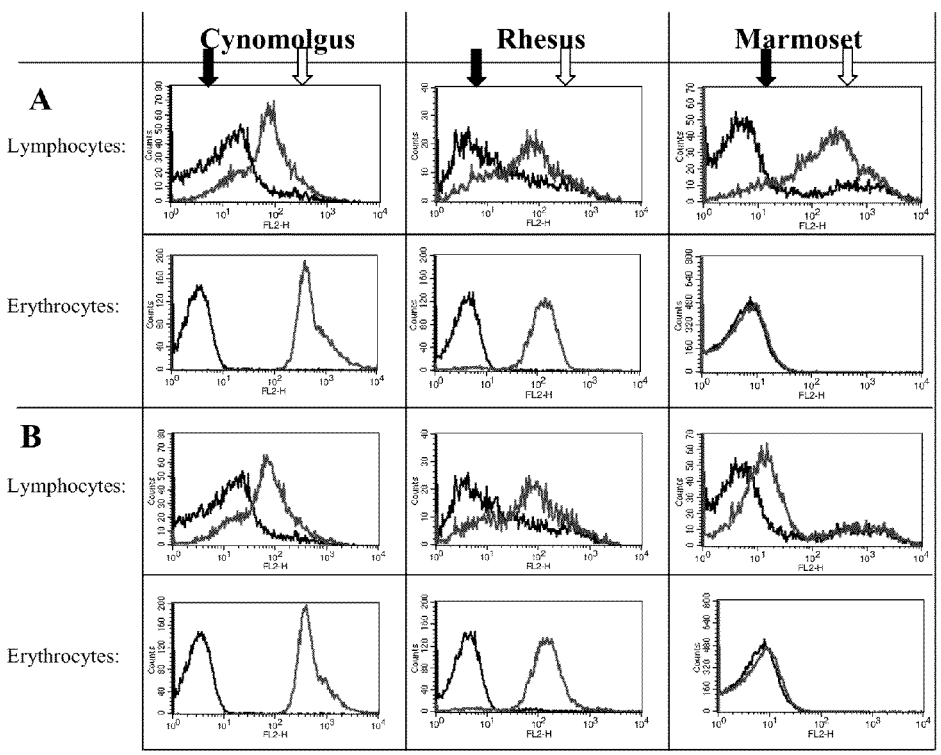

Figure 12: CD38 expression analysis of Lymphocytes and Erythrocytes
MOR 03087:
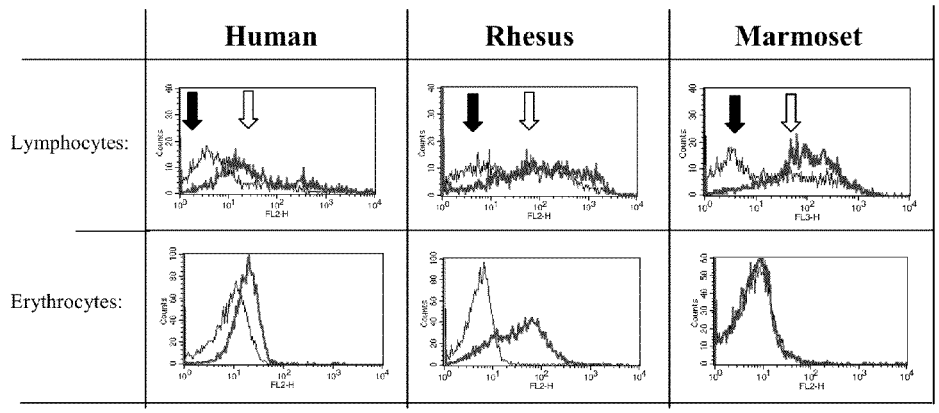

Figure 13: Overview Cross-Reactivity Anti-CD38 Antibodies

| Species/Tissue:<br><br>Anti-CD38 MAbs: | Human | | Rhesus | | Cynomolgus | | Marmoset | |
|---|---|---|---|---|---|---|---|---|
| | PBMCs | Erythr. | PBMCs | Erythr. | PBMCs | Erythr. | PBMCs | Erythr. |
| 3076 | + | n.d. | - | - | - | - | - | - |
| 3077 | + | - | - | - | - | - | - | - |
| 3078 | + | n.d. | - | - | - | - | - | - |
| 3079 | + | + | - | - | - | - | - | - |
| 3080 | + | +/- | + | - | + | - | - | - |
| 3081 | + | n.d. | - | - | - | - | - | - |
| 3085 | + | n.d. | - | - | - | - | - | - |
| 3086 | + | n.d. | - | - | - | - | - | - |
| 3087 | + | +/- | + | + | + | + | + | - |
| 3088 | + | - | + | + | + | + | + | - |
| 3089 | + | n.d. | - | - | - | - | - | - |
| 3101 | + | n.d. | - | - | - | - | - | - |
| 3102 | + | n.d. | - | - | - | - | - | - |
| 3127 | + | n.d. | - | - | - | - | - | - |
| 3128 | + | n.d. | - | - | - | - | - | - |
| 3129 | + | n.d. | - | - | - | - | - | - |
| 3130 | + | n.d. | - | - | - | - | - | - |
| 3131 | + | n.d. | - | - | - | - | - | - |

+ : positive staining
+/-: weak positive staining
- : negative staining
n.d.: not determined

FULLY HUMAN THERAPEUTIC ANTIBODIES SPECIFIC FOR HUMAN CD38

CROSS-REFERENCE TO RELATED APPLICATIONS

This application is a Divisional of U.S. application Ser. No. 13/291,473, filed Nov. 8, 2011, which issued as U.S. Pat. No. 8,486,394 on Jul. 16, 2013; which is a Divisional of U.S. application Ser. No. 12/089,806, which issued as U.S. Pat. No. 8,088,896 on Jan. 3, 2012; U.S. application Ser. No. 12/089,806 entered the U.S. National Stage on Apr. 10, 2008 as a National Stage application of PCT/EP2006/009889, filed Oct. 12, 2006, which was published in English on Apr. 19, 2007 as WO 2007/042309, and which claims the benefit of U.S. provisional application Ser. No. 60/725,297, filed Oct. 12, 2005.

The instant application contains a Sequence Listing which has been submitted in ASCII format via EFS-WEB and is hereby incorporated by reference in its entirety. Said ASCII copy, created on May 22, 2013, is named sequence.txt and is 119 KB.

SUMMARY OF THE INVENTION

The present invention relates to an isolated antigen-binding region that is specific for CD38, which comprises (i) an H-CDR3 region depicted in SEQ ID NO: 16, 17, 18, 19, 20, 21, 22, 23, 24, 25, 26, 27, 28, 29, 30, 92, 93, 94, 95, 96, 97, 98, 99, 100, 101, 102, 103, 104, 105 or 106 or (ii) an H-CDR3 region that has at least a sixty percent identity to an H-CDR3 region depicted in SEQ ID NO: 16, 17, 18, 19, 20, 21, 22, 23, 24, 25, 26, 27, 28, 29, 30, 92, 93, 94, 95, 96, 97, 98, 99, 100, 101, 102, 103, 104, 105 or 106

The present invention furthermore relates to an isolated antibody or functional fragment thereof that is specific for CD38, which comprises (i) a variable heavy chain depicted in SEQ ID NO: 16, 17, 18, 19, 20, 21, 22, 23, 24, 25, 26, 27, 28, 29, 30, 92, 93, 94, 95, 96, 97, 98, 99, 100, 101, 102, 103, 104, 105 or 106 or (ii) a variable heavy chain that has at least a sixty percent identity to a variable heavy chain depicted in SEQ ID NO: 16, 17, 18, 19, 20, 21, 22, 23, 24, 25, 26, 27, 28, 29, 30, 92, 93, 94, 95, 96, 97, 98, 99, 100, 101, 102, 103, 104, 105 or 106.

Additionally, the present invention relates to an isolated antigen-binding region that is specific for CD38, which comprises (i) an L-CDR3 region depicted in SEQ ID NO: 46, 47, 48, 49, 50, 51, 52, 53, 54, 55, 56, 57, 58, 59, 60, 109 or 110 or (ii) an L-CDR3 region that has at least a sixty percent identity to an L-CDR3 region depicted in SEQ ID NO: 46, 47, 48, 49, 50, 51, 52, 53, 54, 55, 56, 57, 58, 59, 60, 109 or 110.

Also, the present invention relates to an isolated antibody or functional fragment thereof, which comprises (i) a variable light chain depicted in SEQ ID NO: 46, 47, 48, 49, 50, 51, 52, 53, 54, 55, 56, 57, 58, 59, 60, 109 or 110 or (ii) a variable light chain that has at least a sixty percent identity to a variable light chain depicted in SEQ ID NO: 46, 47, 48, 49, 50, 51, 52, 53, 54, 55, 56, 57, 58, 59, 60, 109 or 110.

The present invention further relates to a variable heavy chain of an isolated antigen-binding region that is encoded by (i) a nucleic acid sequence comprising SEQ ID NO: 1, 2, 3, 4, 5, 6, 7, 8, 9, 10, 11, 12, 13, 14, 15, 77, 78, 79, 80, 81, 82, 83, 84, 85, 86, 87, 88, 89, 90 or 91 or (ii) a nucleic acid sequences that hybridizes under high stringency conditions to the complementary strand of SEQ ID NO: 1, 2, 3, 4, 5, 6, 7, 8, 9, 10, 11, 12, 13, 14, 15, 77, 78, 79, 80, 81, 82, 83, 84, 85, 86, 87, 88, 89, 90 or 91, wherein said antigen-binding region is specific for CD38.

The present invention also relates to a variable light chain of an isolated antigen-binding region that is encoded by (i) a nucleic acid sequence comprising SEQ ID NO: 31, 32, 33, 34, 35, 36, 37, 38, 39, 40, 41, 42, 43, 44, 45, 107 or 108 or (ii) a nucleic acid sequences that hybridizes under high stringency conditions to the complementary strand of SEQ ID NO: 31, 32, 33, 34, 35, 36, 37, 38, 39, 40, 41, 42, 43, 44, 45, 107 or 108, wherein said antibody or functional fragment thereof is specific for CD38.

Further, the present invention relates to an isolated nucleic acid sequence that encodes an antigen-binding region of a human antibody or functional fragment thereof that is specific for CD38.

Additionally, the invention relates to a nucleic acid sequence encoding a variable heavy chain of an isolated antigen-binding region, which comprises (i) a sequence selected from the group consisting of SEQ ID NOS: 1, 2, 3, 4, 5, 6, 7, 8, 9, 10, 11, 12, 13, 14, 15, 77, 78, 79, 80, 81, 82, 83, 84, 85, 86, 87, 88, 89, 90 and 91 or (ii) a nucleic acid sequence that hybridizes under high stringency conditions to the complementary strand of SEQ ID NO: 1, 2, 3, 4, 5, 6, 7, 8, 9, 10, 11, 12, 13, 14, 15, 77, 78, 79, 80, 81, 82, 83, 84, 85, 86, 87, 88, 89, 90 or 91, wherein said antigen-binding region is specific for CD38.

The present invention also relates to a nucleic acid sequence encoding a variable light chain of an isolated antigen-binding region, which comprises (i) a sequence selected from the group consisting of SEQ ID NOS: 31, 32, 33, 34, 35, 36, 37, 38, 39, 40, 41, 42, 43, 44, 45, 107 and 108 or (ii) a nucleic acid sequence that hybridizes under high stringency conditions to the complementary strand of SEQ ID NO: 31, 32, 33, 34, 35, 36, 37, 38, 39, 40, 41, 42, 43, 44, 45, 107 or 108 wherein said antigen-binding region is specific for CD38.

The present invention further relates to a method of inducing specific killing of tumor cells that express CD38, wherein said specific killing occurs by CD38 cross-linking, comprising the step of incubating said cells in the presence of a sufficient amount of an isolated human or humanized anti-CD38 antibody or a functional fragment thereof, wherein said human or humanized anti-CD38 antibody comprises (i) a nucleic acid sequence encoding a heavy chain depicted in SEQ ID NO: 1, 2, 3, 4, 5, 6, 7, 8, 9, 10, 11, 12, 13, 14, 15, 77, 78, 79, 80, 81, 82, 83, 84, 85, 86, 87, 88, 89, 90 or 91 or (ii) a nucleic acid sequences that hybridizes under high stringency conditions to the complementary strand of SEQ ID NO: 1, 2, 3, 4, 5, 6, 7, 8, 9, 10, 11, 12, 13, 14, 15, 77, 78, 79, 80, 81, 82, 83, 84, 85, 86, 87, 88, 89, 90 or 91, wherein said antibody or a functional fragment thereof is specific for CD38.

Additionally, the present invention relates to A method of inducing specific killing of tumor cells that express CD38, wherein said specific killing occurs by CD38 cross-linking, comprising the step of incubating said cells in the presence of a sufficient amount of an isolated human or humanized anti-CD38 antibody or a functional fragment thereof, wherein said human or humanized anti-CD38 antibody comprises (i) a nucleic acid sequence encoding a light chain depicted in SEQ ID NO: 31, 32, 33, 34, 35, 36, 37, 38, 39, 40, 41, 42, 43, 44, 45, 107 or 108 or (ii) a nucleic acid sequences that hybridizes under high stringency conditions to the complementary strand of SEQ ID NO: 31, 32, 33, 34, 35, 36, 37, 38, 39, 40, 41, 42, 43, 44, 45, 107 or 108, wherein said antibody or a functional fragment thereof is specific for CD38.

Also, the present invention relates to a method of inducing specific killing of tumor cells that express CD38, wherein said specific killing occurs by CD38 cross-linking, comprising the step of incubating said cells in the presence of a sufficient amount of an isolated human or humanized anti-CD38 antibody or a functional fragment thereof, wherein said human or humanized anti-CD38 antibody or said functional fragment thereof comprises (i) a heavy chain amino acid sequence depicted in SEQ ID NO: 16, 17, 18, 19, 20, 21, 22, 23, 24, 25, 26, 27, 28, 29, 30, 92, 93, 94, 95, 96, 97, 98, 99, 100, 101, 102, 103, 104, 105 or 106 or (ii) a variable heavy chain that has at least a sixty percent identity to a variable heavy chain depicted in SEQ ID NO: 16, 17, 18, 19, 20, 21, 22, 23, 24, 25, 26, 27, 28, 29, 30, 92, 93, 94, 95, 96, 97, 98, 99, 100, 101, 102, 103, 104, 105 or 106.

Also, the present invention relates to a method of inducing specific killing of tumor cells that express CD38, wherein said specific killing occurs by CD38 cross-linking, comprising the step of incubating said cells in the presence of a sufficient amount of an isolated human or humanized anti-CD38 antibody or a functional fragment thereof, wherein said human or humanized anti-CD38 antibody comprises (i) and/or a light chain amino acid sequence depicted in SEQ ID NO: 46, 47, 48, 49, 50, 51, 52, 53, 54, 55, 56, 57, 58, 59, 60, 109 or 110 or (ii) a variable light chain that has at least a sixty percent identity to a variable light chain depicted in SEQ ID NO: 46, 47, 48, 49, 50, 51, 52, 53, 54, 55, 56, 57, 58, 59, 60, 109 or 110.

Furthermore, the present invention relates to a method of detecting specific killing of tumor cells that express CD38, by CD38 cross-linking, comprising the steps of:
(i) administering to a subject in need thereof an effective amount of a human or humanized anti-CD38 antibody or a functional fragment thereof, and
(ii) detecting the specific killing activity of said human or humanized anti-CD38 antibody or said functional fragment thereof.

Also, the present invention relates to a method of detecting the presence of CD38 in a tissue or a cell of minipig origin, comprising the steps of:
(i) allowing a human or humanized anti-CD38 antibody or a functional fragment thereof to come into contact with said CD38, and
(ii) detecting the specific binding of said human or humanized anti-CD38 antibody or functional fragment thereof to said CD38 minipig cells, wherein said antibody or functional fragment thereof is also able to specifically bind to CD38 of human origin.

Furthermore, the present invention relates to A method of detecting CD38 in a CD38-expressing erythrocyte, comprising the steps of:
(i) allowing a human or humanized anti-CD38 antibody or a functional fragment thereof to come into contact with said CD38-expressing erythrocyte, and
(ii) detecting the specific binding of said human or humanized anti-CD38 antibody or functional fragment thereof to said CD38-expressing erythrocytes, wherein said antibody or functional fragment thereof is also able to specifically bind to human CD38 from a cell or tissue other than human erythrocytes.

The present invention also relates to an isolated antibody or functional fragment thereof according to the present invention, which comprises (i) an H-CDR3 region depicted in SEQ ID NO: 21 or 22 or (ii) an H-CDR3 region at least a sixty percent identity thereto, and that is specific for human CD38 and marmoset CD38.

BRIEF DESCRIPTION OF THE FIGURES

FIG. 1*a* provides nucleic acid sequences of various antibody variable heavy regions for use in the present invention.

FIG. 1*b* provides amino acid sequences of various antibody variable heavy regions for use in the present invention. CDR regions HCDR1, HCDR2 and HCDR3 are designated from N- to C-terminus in boldface.

FIG. 2*a* provides nucleic acid sequences of various antibody variable light regions for use in the present invention.

FIG. 2*b* provides amino acid sequences of various antibody variable light regions for use in the present invention. CDR regions LCDR1, LCDR2 and LCDR3 are designated from N- to C-terminus in boldface.

FIG. 3 provides amino acid sequences of variable heavy regions of various consensus-based HuCAL antibody master gene sequences. CDR regions HCDR1, HCDR2 and HCDR3 are designated from N- to C-terminus in boldface.

FIG. 4 provides amino acid sequences of variable light regions of various consensus-based HuCAL antibody master gene sequences. CDR regions LCDR1, LCDR2 and LCDR3 are designated from N- to C-terminus in boldface.

FIG. 5 provides the amino acid sequence of CD38 (SWISS-PROT primary accession number P28907).

FIG. 6 provides the nucleotide sequences of the heavy and light chains of chimeric OKT10.

FIG. 7 provides the DNA sequence of pMORPH®_h_IgG1_1 (bp 601-2100) (SEQ ID NO: 74), encoding the IgG1 variable heavy chain (SEQ ID NOS: 129 and 138). The vector is based on the pcDNA3.1+ vectors (Invitrogen). The amino acid sequence of the VH-stuffer sequence is indicated in bold, whereas the final reading frames of the VH-leader sequence and the constant region gene are printed in non-bold. Restriction sites are indicated above the sequence. The priming sites of the sequencing primers are underlined.

FIG. 8 provides the DNA sequence of Ig kappa light chain expression vector pMORPH®_h_Igκ_1 (bp 601-1400) (SEQ ID NO: 75), encoding the variable κ light chain (SEQ ID NO: 130). The vector is based on the pcDNA3.1+ vectors (Invitrogen). The amino acid sequences of the Vκ-stuffer sequence is indicated in bold, whereas the final reading frames of the Vκ-leader sequence and of the constant region gene are printed in non-bold. Restriction sites are indicated above the sequence. The priming sites of the sequencing primers are underlined.

FIG. 9 provides the DNA sequence of HuCAL Ig lambda light chain vector pMORPH®_h_Igλ_1 (bp 601-1400) (SEQ ID NO: 76), encoding the variable λ light chain (SEQ ID NOS: 131 and 139). The amino acid sequence of the Vλ-stuffer sequence is indicated in bold, whereas the final reading frames of the Vλ-leader sequence and of the constant region gene are printed in non-bold. Restriction sites are indicated above the sequence. The priming sites of the sequencing primers are underlined.

FIG. 10 provides different combinations of heavy and light chains in the Fab/IgG format for use in the present invention FIG. 11 provides CD38-expression analysis of Lymphocytes and Erythrocytes obtained by FACS. PBMCs and Erythrocytes were isolated from whole blood of cynomolgus, rhesus and marmoset by density gradient centrifugation followed by FACS-analysis using anti-CD38 Fab antibodies MOR03087 (A, right histograms, light arrow) and MOR03088 (B, right histograms; light arrow). An irrelevant Fab-antibody (A & B, left histograms; black arrow) was used as a negative control.

FIG. 12 provides CD38 expression analysis of Lymphocytes and Erythrocytes obtained by FACS. PBMCs and Erythrocytes were isolated from whole blood of human, cynomolgus and marmoset by density gradient centrifugation followed by FACS-analysis using anti-CD38 IgG1

MOR03087 (right histograms; white arrow). An irrelevant IgG1 control antibody (A & B, left histograms; black arrow) was used as a negative control.

FIG. 13 provides a comparative overview of Cross-Reactivity of different anti-CD38 antibodies.

Figure 14A:
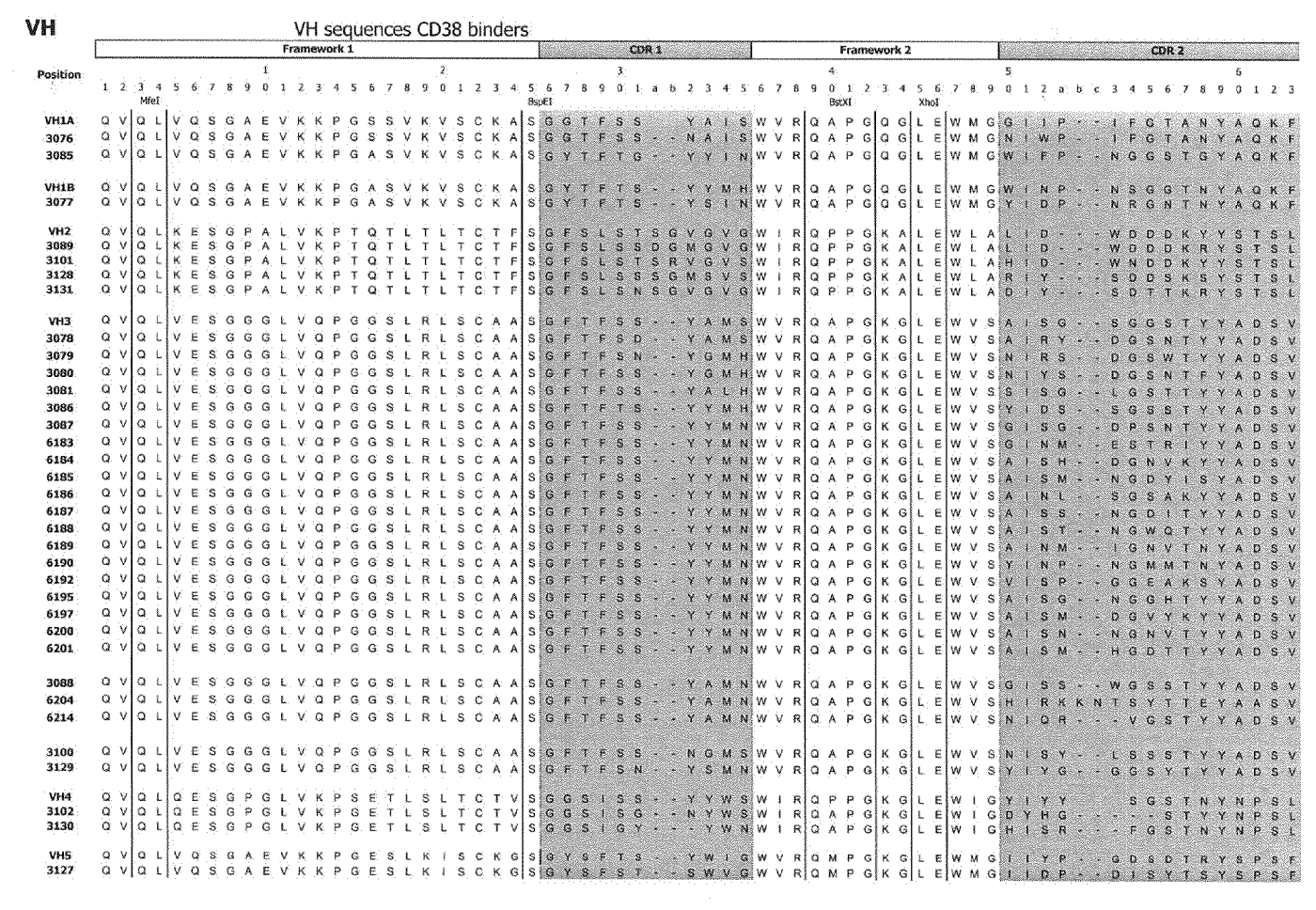
Figure 14A:
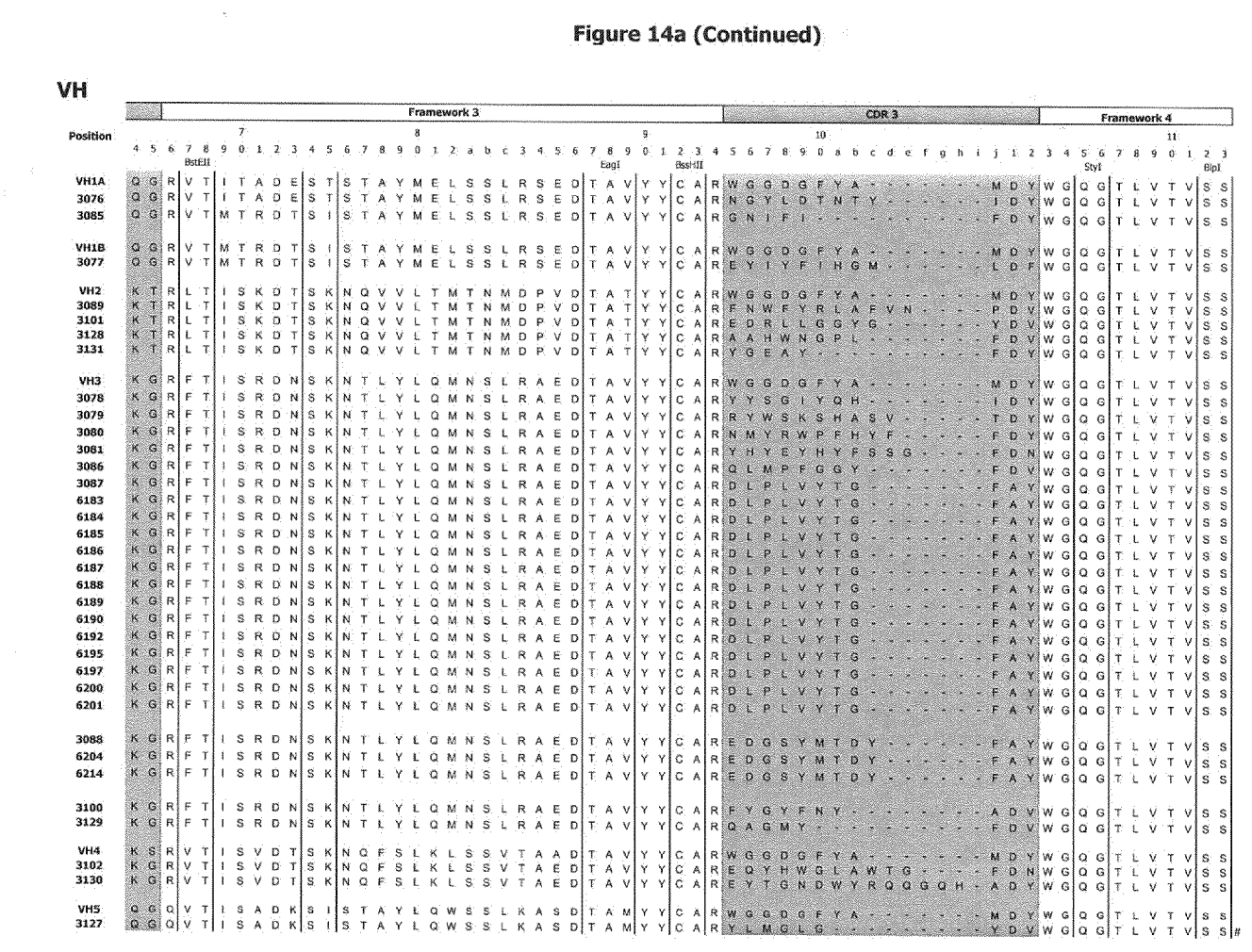
Figure 14B:
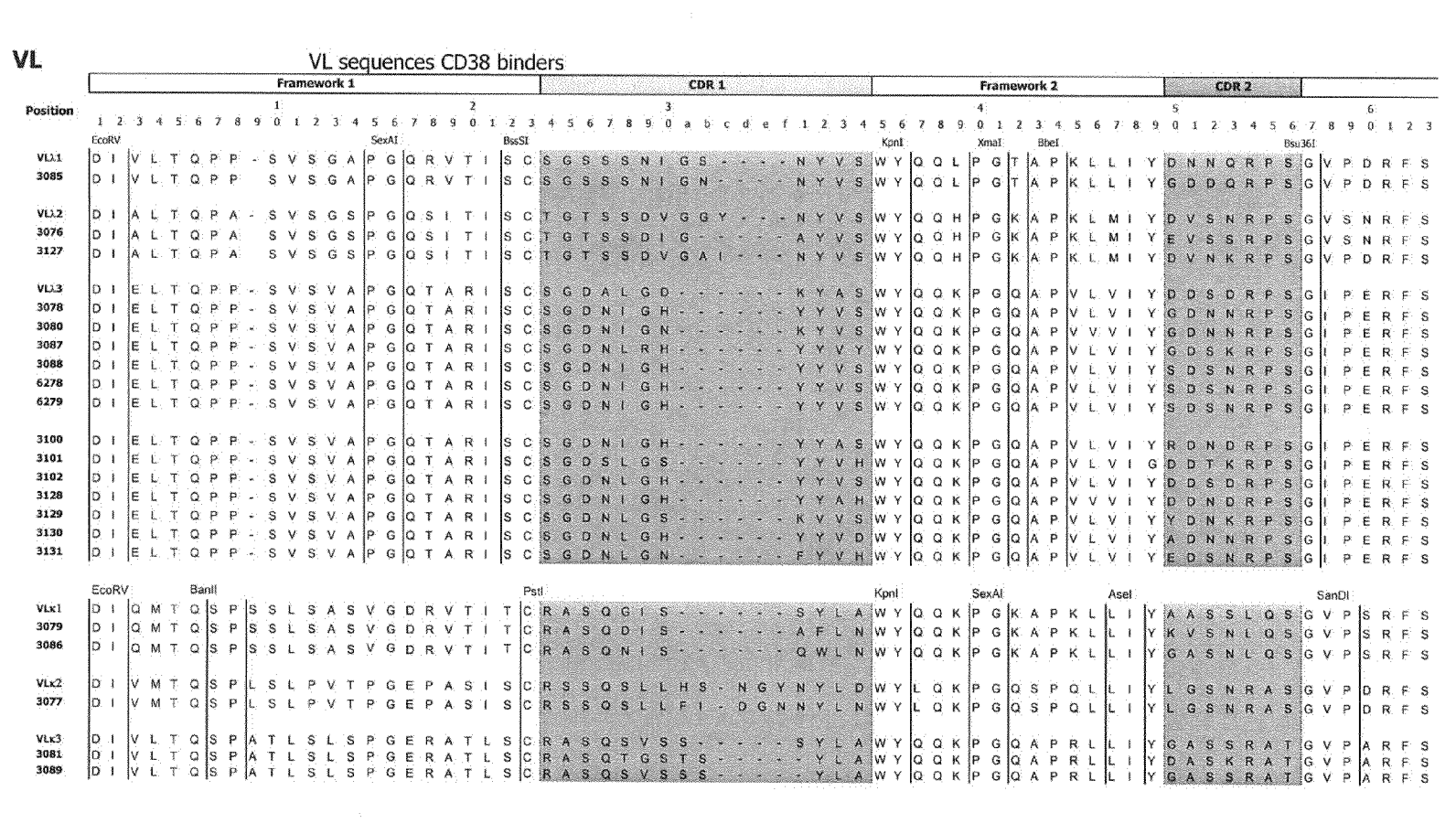
Figure 14B:
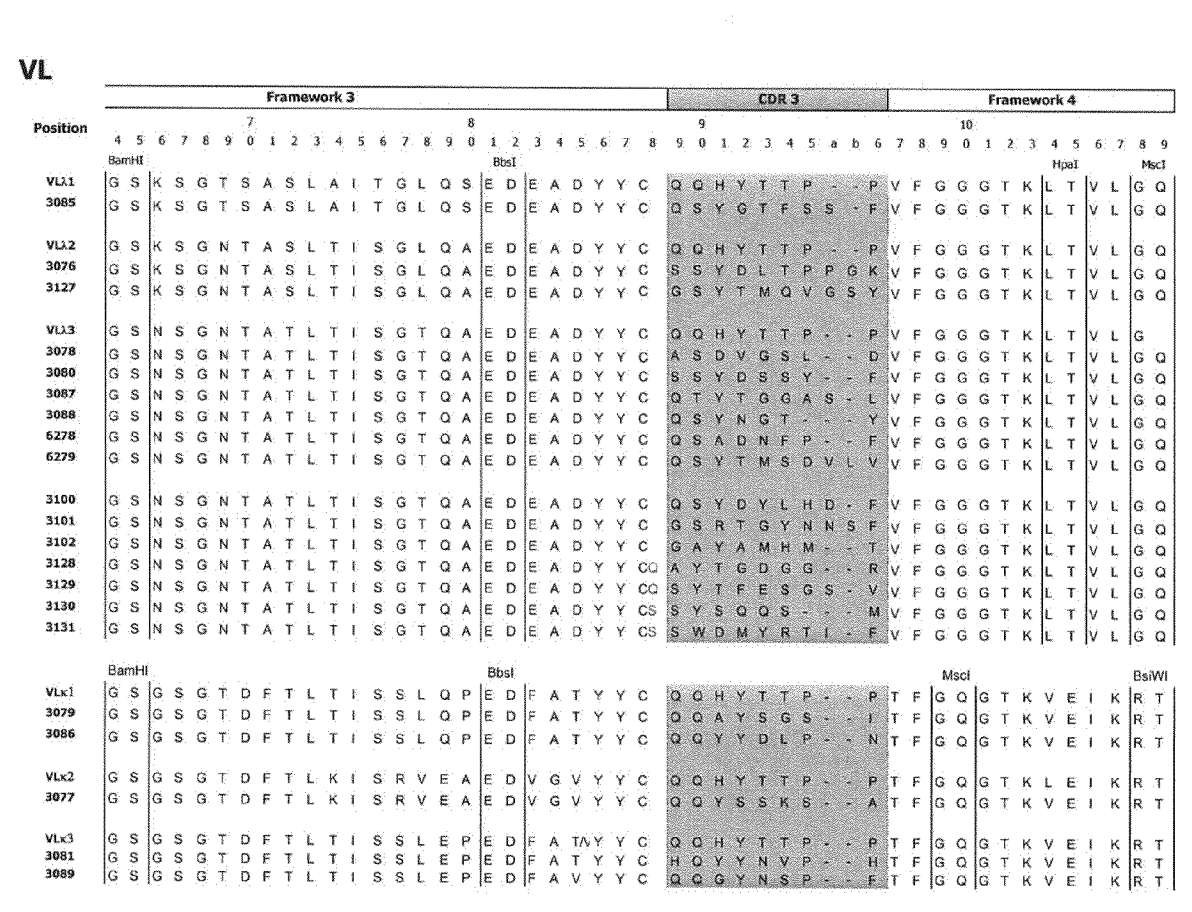

FIGS. 14(a) and 14(b) delineate the CDR and FR regions for certain antibodies for use in the invention and compare amino acids at a given position to each other and to corresponding consensus sequences.

The consensus sequences are VH1A (SEQ ID NO: 61), VH2 (SEQ ID NO: 63), VH3 (SEQ ID NO: 63), VH4 (SEQ ID NO: 64), VH5 (SEQ ID NO: 65), V1_λ1 (SEQ ID NO: 66), V1_λ2 (SEQ ID NO: 67), V1_λ3 (SEQ ID NO: 68), V1_k1 (SEQ ID NO: 69) and V1_k3 (SEQ ID NO: 70). 3076 represents an antibody having a variable heavy region (VH) corresponding to SEQ ID NO: 16 and a variable light (VL) region corresponding to SEQ ID NO: 46. Likewise, 3078 VL (SEQ ID NO: 17) and VL (SEQ ID NO: 47); 3081 VH (SEQ ID NO: 18) and VL (SEQ ID NO: 48); 3085 VH (SEQ ID NO: 19) and VL (SEQ ID NO: 49); 3086 VH (SEQ ID NO: 20) and VL (SEQ ID NO: 50); 3087 VH (SEQ ID NO: 21) and VL (SEQ ID NO: 51); 3088 VH (SEQ ID NO: 22) and VL (SEQ ID NO: 52); 3089 VH (SEQ ID NO: 23) and VL (SEQ ID NO: 53); 3101 VH (SEQ ID NO: 24) and VL (SEQ ID NO: 54); 3102 VH (SEQ ID NO: 25) and VL (SEQ ID NO: 55); 3127 VH (SEQ ID NO: 26) and VL (SEQ ID NO: 56); 3128 VH (SEQ ID NO: 27) and VL (SEQ ID NO: 57); 3129 VH (SEQ ID NO: 28) and VL (SEQ ID NO: 58); 3130 VH (SEQ ID NO: 29) and VL (SEQ ID NO: 59); 3131 VH (SEQ ID NO: 30) and VL (SEQ ID NO: 60); 6183 VH (SEQ ID NO:92); 6184 VH (SEQ ID NO: 93) 6185 VH (SEQ ID NO: 94); 6186 VH (SEQ ID NO: 95); 6187 VH (SEQ ID NO: 96); 6188 VH (SEQ ID NO: 97); 6189 VH (SEQ ID NO:98); 6190 VH (SEQ ID NO: 99); 6192 VH (SEQ ID NO: 100); 6195 VH (SEQ ID NO: 101); 6197 VH (SEQ ID NO: 102); 6200 VH (SEQ ID NO: 103); 6201 VH (SEQ ID NO: 104); 6204 VH (SEQ ID NO: 105); 6214 VH (SEQ ID NO: 106); 6278 VL (SEQ ID NO: 109); and 6279 VL (SEQ ID NO: 110).

DETAILED DESCRIPTION OF THE INVENTION

The present invention is based on the discovery of novel antibodies and methods of using antibodies that are specific to or have a high affinity for CD38 and can deliver a therapeutic benefit to a subject. The antibodies, which may be human or humanized, can be used in many contexts, which are more fully described herein. Suitable antibodies for use in the present invention are disclosed in U.S. 60/614,471, which hereby is incorporated by reference.

A "human" antibody or functional human antibody fragment is hereby defined as one that is not chimeric (e.g., not "humanized") and not from (either in whole or in part) a non-human species. A human antibody or functional antibody fragment can be derived from a human or can be a synthetic human antibody. A "synthetic human antibody" is defined herein as an antibody having a sequence derived, in whole or in part, in silico from synthetic sequences that are based on the analysis of known human antibody sequences. In silico design of a human antibody sequence or fragment thereof can be achieved, for example, by analyzing a database of human antibody or antibody fragment sequences and devising a polypeptide sequence utilizing the data obtained therefrom. Another example of a human antibody or functional antibody fragment, is one that is encoded by a nucleic acid isolated from a library of antibody sequences of human origin (i.e., such library being based on antibodies taken from a human natural source).

A "humanized antibody" or functional humanized antibody fragment is defined herein as one that is (i) derived from a non-human source (e.g., a transgenic mouse which bears a heterologous immune system), which antibody is based on a human germline sequence; or (ii) chimeric, wherein the variable domain is derived from a non-human origin and the constant domain is derived from a human origin or (iii) CDR-grafted, wherein the CDRs of the variable domain are from a non-human origin, while one or more frameworks of the variable domain are of human origin and the constant domain (if any) is of human origin.

As used herein, an antibody "binds specifically to," is "specific to/for" or "specifically recognizes" an antigen (here, CD38) if such antibody is able to discriminate between such antigen and one or more reference antigen(s), since binding specificity is not an absolute, but a relative property. In its most general form (and when no defined reference is mentioned), "specific binding" is referring to the ability of the antibody to discriminate between the antigen of interest and an unrelated antigen, as determined, for example, in accordance with one of the following methods. Such methods comprise, but are not limited to Western blots, ELISA-, RIA-, ECL-, IRMA-tests, FACS, IHC and peptide scans. For example, a standard ELISA assay can be carried out. The scoring may be carried out by standard color development (e.g. secondary antibody with horseradish peroxide and tetramethyl benzidine with hydrogenperoxide). The reaction in certain wells is scored by the optical density, for example, at 450 nm. Typical background (=negative reaction) may be 0.1 OD; typical positive reaction may be 1 OD. This means the difference positive/negative can be more than 10-fold. Typically, determination of binding specificity is performed by using not a single reference antigen, but a set of about three to five unrelated antigens, such as milk powder, BSA, transferrin or the like. It is possible for an antibody to be "specific to" or "specific for" an antigen of 2 or more cells/tissues and/or 2 or more species, provided that the antibody meets binding criteria for each of such cells/tissues and species, for example. Accordingly, an antibody may bind specifically to the target antigen CD38 on various cell types and/or tissues, e.g. erythrocytes, lymphocytes isolated from peripheral blood, spleen or lymph-nodes. In addition, an antibody may be specific to both CD38 of one species and CD38 of another species.

"Specific binding" also may refer to the ability of an antibody to discriminate between the target antigen and one or more closely related antigen(s), which are used as reference points, e.g. between CD38 and CD157. Additionally, "specific binding" may relate to the ability of an antibody to discriminate between different parts of its target antigen, e.g. different domains or regions of CD38, such as epitopes in the N-terminal or in the C-terminal region of CD38, or between one or more key amino acid residues or stretches of amino acid residues of CD38.

Also, as used herein, an "immunoglobulin" (Ig) hereby is defined as a protein belonging to the class IgG, IgM, IgE, IgA, or IgD (or any subclass thereof), and includes all conventionally known antibodies and functional fragments thereof. A "functional fragment" of an antibody/immunoglobulin hereby is defined as a fragment of an antibody/immunoglobulin (e.g., a variable region of an IgG) that retains the antigen-binding region. An "antigen-binding region" of an antibody typically is found in one or more hypervariable region(s) of an antibody, i.e., the CDR-1, -2, and/or -3 regions; however, the variable "framework" regions can also play an important role in antigen binding, such as by providing a scaffold for the CDRs. Preferably, the "antigen-binding region" comprises at least amino acid residues 4 to 103 of the variable light (VL) chain and 5 to 109 of the variable heavy (VH) chain, more preferably amino acid residues 3 to 107 of VL and 4 to 111 of VH, and particularly preferred are the complete VL and VH chains (amino acid positions 1 to 109 of VL and 1 to 113 of VH; numbering according to WO 97/08320). A preferred class of immunoglobulins for use in the present invention is IgG. "Functional fragments" of the invention include the domain of a F(ab')$_2$ fragment, a Fab fragment and scFv. The F(ab')$_2$ or Fab may be engineered to minimize or completely remove the intermolecular disulphide interactions that occur between the $C_{H1}$ and $C_L$ domains.

The term "parental binder" as used in connection with the present invention denotes any binder which has not undergone the process of optimization. A process of optimization is described elsewhere in the present specification.

The term "binder" as used in connection with the present invention may be used in a synonymous manner as the term "immunoglobulin" or "antibody".

An antibody for use in the invention may be derived from a recombinant antibody library that is based on amino acid sequences that have been designed in silico and encoded by nucleic acids that are synthetically created. In silico design of an antibody sequence is achieved, for example, by analyzing a database of human sequences and devising a polypeptide sequence utilizing the data obtained therefrom. Methods for designing and obtaining in silico-created sequences are described, for example, in Knappik et al., J. Mol. Biol. (2000) 296:57; Krebs et al., J. Immunol. Methods. (2001) 254:67; and U.S. Pat. No. 6,300,064 issued to Knappik et al., which hereby are incorporated by reference in their entirety.

Antibodies for Use in the Invention

Throughout this document, reference is made to the following representative antibodies for use in the invention: "antibody nos." or "LACS" or "MOR" 3076 or 03076, 3078 or 03078, 3081 or 03081, 3085 or 03085, 3086 or 03086, 3087 or 03087, 3088 or 03088, 3089 or 03089, 3101 or 03101, 3102 or 03102, 3127 or 03127, 3128 or 03128, 3129 or 03129, 3130 or 03130, 3131 or 03131, 6183 or 06183, 6184 or 06184, 6185 or 06185, 6186 or 06186, 6187 or 06187, 6188 or 06188, 6189 or 06189, 6190 or 06190, 6192 or 06192, 6195 or 06195, 6197 or 06197, 6200 or 06200, 6201 or 06201, 6204 or 06204, 6214 or 06214, 6278 or 06278, 6279 or 06279. LAC 3076 represents an antibody having a variable heavy region corresponding to SEQ ID NO: 1 (DNA)/SEQ ID NO: 16 (protein) and a variable light region corresponding to SEQ ID NO: 31 (DNA)/SEQ ID NO: 46 (protein). LAC 3078 represents an antibody having a variable heavy region corresponding to SEQ ID NO: 2 (DNA)/SEQ ID NO: 17 (protein) and a variable light region corresponding to SEQ ID NO: 32 (DNA)/SEQ ID NO: 47 (protein). LAC 3081 represents an antibody having a variable heavy region corresponding to SEQ ID NO: 3 (DNA)/SEQ ID NO: 18 (protein) and a variable light region corresponding to SEQ ID NO: 33 (DNA)/SEQ ID NO: 48 (protein). LAC 3085 represents an antibody having a variable heavy region corresponding to SEQ ID NO: 4 (DNA)/SEQ ID NO: 19 (protein) and a variable light region corresponding to SEQ ID NO: 34 (DNA)/SEQ ID NO: 49 (protein). LAC 3086 represents an antibody having a variable heavy region corresponding to SEQ ID NO: 5 (DNA)/SEQ ID NO: 20 (protein) and a variable light region corresponding to SEQ ID NO: 35 (DNA)/SEQ ID NO: 50 (protein). LAC 3087 represents an antibody having a variable heavy region corresponding to SEQ ID NO: 6 (DNA)/SEQ ID NO: 21 (protein) and a variable light region corresponding to SEQ ID NO: 36 (DNA)/SEQ ID NO: 51 (protein). LAC 3088 represents an antibody having a variable heavy region corresponding to SEQ ID NO: 7 (DNA)/SEQ ID NO: 22 (protein) and a variable light region corresponding to SEQ ID NO: 37 (DNA)/SEQ ID NO: 52 (protein). LAC 3089 represents an antibody having a variable heavy region corresponding to SEQ ID NO: 8 (DNA)/SEQ ID NO: 23 (protein) and a variable light region corresponding to SEQ ID NO: 38 (DNA)/SEQ ID NO: 53 (protein). LAC 3101 represents an antibody having a variable heavy region corresponding to SEQ ID NO: 9 (DNA)/SEQ ID NO: 24 (protein) and a variable light region corresponding to SEQ ID NO: 39 (DNA)/SEQ ID NO: 54 (protein). LAC 3102 represents an antibody having a variable heavy region corresponding to SEQ ID NO: 10 (DNA)/SEQ ID NO: 25 (protein) and a variable light region corresponding to SEQ ID NO: 40 (DNA)/SEQ ID NO: 55 (protein). LAC 3127 represents an antibody having a variable heavy region corresponding to SEQ ID NO: 11 (DNA)/SEQ ID NO: 26 (protein) and a variable light region corresponding to SEQ ID NO: 41 (DNA)/SEQ ID NO: 56 (protein). LAC 3128 represents an antibody having a variable heavy region corresponding to SEQ ID NO: 12 (DNA)/SEQ ID NO: 27 (protein) and a variable light region corresponding to SEQ ID NO: 42 (DNA)/SEQ ID NO: 57 (protein). LAC 3129 represents an antibody having a variable heavy region corresponding to SEQ ID NO: 13 (DNA)/SEQ ID NO: 28 (protein) and a variable light region corresponding to SEQ ID NO: 43 (DNA)/SEQ ID NO: 58 (protein). LAC 3130 represents an antibody having a variable heavy region corresponding to SEQ ID NO: 14 (DNA)/SEQ ID NO: 29 (protein) and a variable light region corresponding to SEQ ID NO: 44 (DNA)/SEQ ID NO: 59 (protein). LAC 3131 represents an antibody having a variable heavy region corresponding to SEQ ID NO: 15 (DNA)/SEQ ID NO: 30 (protein) and a variable light region corresponding to SEQ ID NO: 45 (DNA)/SEQ ID NO: 60 (protein). Furthermore, optimized clones, which were derived from the parental binders MOR03087 and MOR03088, comprise the following: MOR06183 represents an antibody having a variable heavy region corresponding to SEQ ID NO: 77 (DNA)/SEQ ID NO: 92 (protein). MOR06184 represents an antibody having a variable heavy region corresponding to SEQ ID NO: 78 (DNA)/SEQ ID NO: 93 (protein). MOR06185 represents an antibody having a variable heavy region corresponding to SEQ ID NO: 79 (DNA)/SEQ ID NO: 94 (protein). MOR06186 represents an antibody having a variable heavy region corresponding to SEQ ID NO: 80 (DNA)/SEQ ID NO: 95 (protein). MOR06187 represents an antibody having a variable heavy region corresponding to SEQ ID NO: 81 (DNA)/SEQ ID NO: 96 (protein). MOR06188 represents an antibody having a variable heavy region corresponding to SEQ ID NO: 82 (DNA)/SEQ ID NO: 97. MOR06189 represents an antibody having a variable heavy region corresponding to SEQ ID NO: 83 (DNA)/SEQ ID NO:98 (protein). MOR06190 represents an antibody having a variable heavy region corresponding to SEQ ID NO: 84 (DNA)/SEQ ID NO: 99 (protein). MOR06192 represents an antibody having a variable heavy region corresponding to SEQ ID NO: 85 (DNA)/SEQ ID NO: 100 (protein). MOR06195 represents an antibody having a variable heavy region corresponding to SEQ ID NO: 86 (DNA)/SEQ ID NO: 101 (protein). MOR06197 represents an antibody having a variable heavy region corresponding to SEQ ID NO: 87 (DNA)/SEQ ID NO: 102 (protein). MOR06200 represents an antibody having a variable heavy region corresponding to SEQ ID NO: 88 (DNA)/SEQ ID NO: 103 (protein). MOR06201 represents an antibody having a variable heavy region corresponding to SEQ ID NO: 89 (DNA)/SEQ ID NO: 104 (protein). MOR 06204 represents an antibody having a variable heavy region corresponding to SEQ ID NO: 90 (DNA)/SEQ ID NO: 105 (protein). MOR06214 represents an antibody having a variable heavy region corresponding to SEQ ID NO: 91 (DNA)/SEQ ID NO: 106 (protein). MOR06278 represents an antibody having a variable light region corresponding to SEQ ID NO: 107 (DNA)/SEQ ID NO: 109 (protein). MOR 06279 represents an antibody having a variable light region corresponding to SEQ ID NO: 108 (DNA)/SEQ ID NO: 110 (protein).

Antibodies of the invention were characterized in Fab and/or IgG format and comprise various combinations of the light and heavy chains of optimized and parental binders. FIG. 10 shows several non-limiting combinations which can be used in connection with the present invention.

In one aspect, the invention provides methods for using antibodies having an antigen-binding region that can bind specifically to or has a high affinity for one or more regions of CD38, whose amino acid sequence is depicted by SEQ ID NO: 71. An antibody is said to have a "high affinity" for an antigen if the affinity measurement is at least 100 nM (monovalent affinity of Fab fragment). An antibody or antigen-binding region for use in the present invention preferably can bind to CD38 with an affinity of about less than 600 nM. Preferably, the antibody or antigen-binding region for use in the present invention can bind to CD38 with an affinity of about less than 100 nM, more preferably less than about 60 nM, and still more preferably less than about 30 nM. Further preferred are uses of antibodies that bind to CD38 with an affinity of less than about 10 nM, and more preferably less than 3 about nM. For instance, the affinity of an antibody for use in the invention against CD38 may be about 10.0 nM or 2.4 nM (monovalent affinity of Fab fragment).

Table 1 provides a summary of affinities of representative antibodies, as determined by surface plasmon resonance (Biacore) and FACS Scatchard analysis:

TABLE 1

| Antibody Affinities | | |
|---|---|---|
| Antibody (Fab or IgG1) | BIACORE (Fab) $K_D$ [nM][a] | FACS Scatchard (IgG1)[b] $K_D$ [nM] |
| MOR03076 | 440/596 | n.d. |
| MOR03078 | n.d. | n.d. |
| MOR03081 | 416/450 | 2.5 |
| MOR03085 | 122 | 10 |

TABLE 1-continued

| Antibody Affinities | | |
|---|---|---|
| Antibody (Fab or IgG1) | BIACORE (Fab) $K_D$ [nM][a] | FACS Scatchard (IgG1)[b] $K_D$ [nM] |
| MOR03086 | 30 | n.d. |
| MOR03087 | 17/38 | 5 |
| MOR03088 | 95 | n.d. |
| MOR03089 | 340 | n.d. |
| MOR03101 | 314 | n.d. |
| MOR03102 | 64 | 5 |
| MOR03127 | 168 (54)[c] | n.d. |
| MOR03128 | 117/84[d] | n.d. |
| MOR03129 | 43 | n.d. |
| MOR03130 | n.d. | n.d. |
| MOR03131 | 451 | n.d. |
| Chimeric OKT10 | n.d. | 8.28 |

[a]Fab format; analysis on human CD38 Fc-fusion aa 45-300
[b]IgG1 format; analysis with Raji cells
[c]standard deviation (n = 3)
[d]standard deviation (n = 4)

With reference to Table 1, the affinity of LACs was measured by surface plasmon resonance (Biacore) on human CD38 Fc-fusion and by a flow cytometry procedure utilizing the CD38-expressing human Raji cell line. The Biacore studies were performed on directly immobilized antigen (CD38-Fc fusion protein). The Fab format of LACs exhibit an monovalent affinity range between about 30 and 596 nM on immobilized CD38-Fc fusion protein.

The IgG1 format was used for the cell-based affinity determination (FACS Scatchard). The right column of Table 1 denotes the binding strength of the LACS in this format.

Another preferred feature of preferred antibodies for use in the invention is their specificity for an area within the N-terminal region of CD38. For example, LACs of the invention can bind specifically to the N-terminal region of CD38.

Optimized antibodies of the present invention were further characterized as shown in Tables 2 and 3. Summaries are provided of affinities as determined by surface plasmon resonance (Biacore) and FACS Scatchard analysis. Additionally, FACS-binding to human erythrocytes and ELISA binding studies to CD38 Fc-Fusion protein have also been determined. The characterizations show that several optimized binders show a reduced binding to human erythrocytes and a higher ELISA signal as compared to the parental clone. In addition derivatives of MOR03088 have an improved affinity as shown by FACS Scatchards and affinity determinations.

TABLE 2

Overview characterizations of affinity-matured clones:

| | | Affinities | | Scatchards [EC$_{50}$s] | | FACS anal. FACS-Binding to human Erythrocytes[b] | | ELISA CD38 Fc-Fusion protein[b] |
|---|---|---|---|---|---|---|---|---|
| | | KDs | KDs | | | | | |
| MOR# | Optimization | (Biacore)[a] [nM] | (Bioveris)[a] [pM] | RPMI8226[a] [nM] | OPM2[b] [nM] | (Compared to MOR03087) | Efficacy ADCC[b,c] | (% Reactivity of MOR03087) |
| 03087 | Parental | 5.68 | 48.77 | 5.37 | 17.4*/15.7 | = MOR03087 | + | 100 |
| 6183 | H-CDR2 | 13.47 | 25.98 | 28.06 | 8.91 | <MOR03087 | + | 106 |
| 6184 | H-CDR2 | 9.68 | 66.22 | 4.01 | 10.58 | ~MOR03087 | n.d. | 150 |
| 6185 | H-CDR2 | 4.39 | 13.69 | 7.30 | 11.50 | <MOR03087 | + | 142 |
| 6186 | H-CDR2 | 4.62 | 5.09 | 6.47 | 15.57 | <MOR03087 | n.d. | 117 |
| 6187 | H-CDR2 | 12.46 | 45.38 | 16.85 | 9.37 | ~MOR03087 | n.d. | 145 |
| 6188 | H-CDR2 | 3.96 | 59.32 | 22.71 | 20.15 | <MOR03087 | n.d. | 140 |
| 6189 | H-CDR2 | 4.95 | 24.69 | 9.41 | n.e. | ~MOR03087 | n.d. | 126 |
| 6190 | H-CDR2 | 15.65 | 48.85 | 11.66 | n.e. | <MOR03087 | n.d. | 125 |

TABLE 2-continued

Overview characterizations of affinity-matured clones:

| | | Affinities | | Scatchards [EC$_{50}$s] | | FACS anal. FACS-Binding to human | | ELISA CD38 Fc-Fusion protein[b] |
|---|---|---|---|---|---|---|---|---|
| | | KDs | KDs | | | Erythrocytes[b] | | |
| MOR# | Optimization | (Biacore)[a] [nM] | (Bioveris)[a] [pM] | RPMI8226[a] [nM] | OPM2[b] [nM] | (Compared to MOR03087) | Efficacy ADCC[b,c] | (% Reactivity of MOR03087) |
| 6192 | H-CDR2 | 5.01 | 74.73 | 7.07 | n.e. | ~MOR03087 | n.d. | 111 |
| 6195 | H-CDR2 | 4.52 | 55.73 | 5.60 | n.e. | ~MOR03087 | n.d. | 155 |
| 6197 | H-CDR2 | 4.81 | 12.74 | 6.92 | n.e. | <MOR03087 | n.d. | 138 |
| 6200 | H-CDR2 | 7.92 | 59.91 | 5.02 | 7.15 | >MOR03087 | n.d. | 144 |
| 6201 | H-CDR2 | 6.81 | 18.59 | 9.00 | n.e. | ~MOR03087 | n.d. | 137 |
| 03088 | Parental | 41.40 | 2149.92 | 24.6* | 15.3* | no binding | + | 18 |
| 6204 | H-CDR2 | 22.72 | 58.51 | 6.36 | n.e. | <MOR03087 | n.d. | 56 |
| 6214 | H-CDR2 | 5.26 | 93.65 | 5.32 | n.e. | <MOR03087 | n.d. | 109 |
| 6347 | L-CDR3 | n.d. | n.d. | n.d. | n.d. | n.d. | n.d. | n.d. |
| 6348 | L-CDR3 | n.d. | n.d. | n.d. | n.d. | n.d. | n.d. | n.d. |

[a]Fab-format
[b]IgG-format
[c]Human Effector cells & RPMI8226 Target cells (E:T ratio = 30:1)
+: Killing of RPMI8226 cells in ADCC
n.d.: not determined
*different experiment

TABLE 3

EC$_{50}$ in FACS-Scatchard, ADCC and CDC

| | Characterizations | | | | |
|---|---|---|---|---|---|
| | FACS-Scatchard | | | | CDC |
| Anti-CD38 MAbs: | RPMI8226 EC$_{50}$ [nM][a] | CCRF-CEM EC$_{50}$ [nM][a] | OPM2 EC$_{50}$ [nM][b] | ADCC RPMI8226 EC$_{50}$ [nM][b] | CHO EC$_{50}$ [nM][a] |
| MOR03087 | 6.3 | 14.7 | 17.54 | 0.14 | 3.4 |
| MOR03088 | 24.6 | 25.5 | 2.6 | n.e. | n.e. |
| MOR03080 | 1.8 | 2.6 | 1.9 | 0.13 | 1.9 |

[a]single measurement
[b]mean from 2 measurements

The type of epitope to which an antibody for use in the invention binds may be linear (i.e. one consecutive stretch of amino acids) or conformational (i.e. multiple stretches of amino acids). In order to determine whether the epitope of a particular antibody is linear or conformational, the skilled worker can analyze the binding of antibodies to overlapping peptides (e.g., 13-mer peptides with an overlap of 11 amino acids) covering different domains of CD38. LACS may recognize discontinuous or linear epitopes in the N-terminal region of CD38. Combined with the knowledge provided herein, the skilled worker in the art will know how to use one or more isolated epitopes of CD38 for generating antibodies having an antigen-binding region that is specific for said epitopes (e.g. using synthetic peptides of epitopes of CD38 or cells expressing epitopes of CD38).

An antibody for use in the invention preferably is species cross-reactive with humans and at least one other non-human species. The non-human species can be non-human primate, e.g. rhesus, baboon and/or cynomolgus. Other non-human species can be minipig, rabbit, mouse, rat and/or hamster. An antibody that is cross reactive with at least one other species beside human can provide greater flexibility and benefits over known anti-CD38 antibodies, for purposes of conducting in vivo studies in multiple species with the same antibody. An antibody that is cross reactive with minipig and/or rabbit, for example, can be a candidate for toxicology and safety studies.

Preferably, an antibody for use in the invention not only is able to bind to CD38, but also is able to mediate killing of a cell expressing CD38. More specifically, an antibody for use in the invention can mediate its therapeutic effect by depleting CD38-positive (e.g., malignant) cells via antibody-effector functions. These functions include antibody-dependent cellular cytotoxicity (ADCC) and complement-dependent cytotoxicity (CDC).

CD38-expression, however, is not only found on immune cells within the myeloid (e.g. monocytes, granulocytes) and lymphoid lineage (e.g. activated B and T-cells; plasma cells), but also on the respective precursor cells. Since it is important that those cells are not affected by antibody-mediated killing of malignant cells, the antibodies of the present invention are preferably not cytotoxic to precursor cells.

In addition to its catalytic activities as a cyclic ADP-ribose cyclase and hydrolase, CD38 displays the ability to transduce signals of biological relevance (Hoshino et al., 1997; Ausiello et al., 2000). Those functions can be induced in vivo by, e.g. receptor-ligand interactions or by cross-linking with agonistic anti-CD38 antibodies, leading, e.g. to calcium mobilization, lymphocyte proliferation and release of cytokines. Preferably, the antibodies of the present invention are non-agonistic antibodies.

Peptide Variants

Antibodies for use in the invention are not limited to the specific peptide sequences provided herein. Rather, the invention also embodies the use of variants of these polypeptides. With reference to the instant disclosure and conventionally available technologies and references, the skilled worker will be able to prepare, test and utilize functional variants of the antibodies disclosed herein, while appreciating that variants having the ability to mediate killing of a CD38+ target cell fall within the scope of the present invention. As used in this context, "ability to mediate killing of a CD38+ target cell" means a functional characteristic ascribed to an anti-CD38 antibody for use in the invention. Ability to mediate killing of a CD38+ target cell, thus, includes the ability to mediate killing of a CD38+ target cell, e.g. by ADCC and/or CDC, or by toxin constructs conjugated to an antibody for use in the invention.

A variant can include, for example, an antibody that has at least one altered complementarity determining region (CDR) (hyper-variable) and/or framework (FR) (variable) domain/position, vis-à-vis a peptide sequence disclosed herein. To better illustrate this concept, a brief description of antibody structure follows.

An antibody is composed of two peptide chains, each containing one (light chain) or three (heavy chain) constant domains and a variable region (VL, VH), the latter of which is in each case made up of four FR regions and three interspaced CDRs. The antigen-binding site is formed by one or more CDRs, yet the FR regions provide the structural framework for the CDRs and, hence, play an important role in antigen binding. By altering one or more amino acid residues in a CDR or FR region, the skilled worker routinely can generate mutated or diversified antibody sequences, which can be screened against the antigen, for new or improved properties, for example.

FIGS. 14a (VH) and 14b (VL) delineate the CDR and FR regions for certain antibodies for use in the invention and compare amino acids at a given position to each other and to corresponding consensus or "master gene" sequences (as described in U.S. Pat. No. 6,300,064).

The skilled worker will be able to design peptide variants, the use of which is within the scope of the present invention. It is preferred that variants are constructed by changing amino acids within one or more CDR regions; a variant might also have one or more altered framework regions. Alterations also may be made in the framework regions. For example, a peptide FR domain might be altered where there is a deviation in a residue compared to a germline sequence.

Furthermore, variants may be obtained by using one LAC as starting point for optimization by diversifying one or more amino acid residues in the LAC, preferably amino acid residues in one or more CDRs, and by screening the resulting collection of antibody variants for variants with improved properties. Particularly preferred is diversification of one or more amino acid residues in CDR-3 of VL, CDR-3 of VH, CDR-1 of VL and/or CDR-2 of VH. Diversification can be done by synthesizing a collection of DNA molecules using trinucleotide mutagenesis (TRIM) technology (Virnekäs, B., Ge, L., Plückthun, A., Schneider, K. C., Wellnhofer, G., and Moroney S. E. (1994) Trinucleotide phosphoramidites: ideal reagents for the synthesis of mixed oligonucleotides for random mutagenesis. Nucl. Acids Res. 22, 5600).

Conservative Amino Acid Variants

Polypeptide variants may be made that conserve the overall molecular structure of an antibody peptide sequence described herein. Given the properties of the individual amino acids, some rational substitutions will be recognized by the skilled worker. Amino acid substitutions, i.e., "conservative substitutions," may be made, for instance, on the basis of similarity in polarity, charge, solubility, hydrophobicity, hydrophilicity, and/or the amphipathic nature of the residues involved.

For example, (a) nonpolar (hydrophobic) amino acids include alanine, leucine, isoleucine, valine, proline, phenylalanine, tryptophan, and methionine; (b) polar neutral amino acids include glycine, serine, threonine, cysteine, tyrosine, asparagine, and glutamine; (c) positively charged (basic) amino acids include arginine, lysine, and histidine; and (d) negatively charged (acidic) amino acids include aspartic acid and glutamic acid. Substitutions typically may be made within groups (a)-(d). In addition, glycine and proline may be substituted for one another based on their ability to disrupt α-helices. Similarly, certain amino acids, such as alanine, cysteine, leucine, methionine, glutamic acid, glutamine, histidine and lysine are more commonly found in α-helices, while valine, isoleucine, phenylalanine, tyrosine, tryptophan and threonine are more commonly found in β-pleated sheets. Glycine, serine, aspartic acid, asparagine, and proline are commonly found in turns. Some preferred substitutions may be made among the following groups: (i) S and T; (ii) P and G; and (iii) A, V, L and I. Given the known genetic code, and recombinant and synthetic DNA techniques, the skilled scientist readily can construct DNAs encoding the conservative amino acid variants. In one particular example, amino acid position 3 in SEQ ID NOS: 5, 6, 7, and/or 8 can be changed from a Q to an E.

As used herein, "sequence identity" between two polypeptide sequences indicates the percentage of amino acids that are identical between the sequences. "Sequence similarity" indicates the percentage of amino acids that either are identical or that represent conservative amino acid substitutions. Preferred polypeptide sequences of the invention have a sequence identity in the CDR regions of at least 60%, more preferably, at least 70% or 80%, still more preferably at least 90% and most preferably at least 95%. Preferred antibodies also have a sequence similarity in the CDR regions of at least 80%, more preferably 90% and most preferably 95%. Preferred polypeptide sequences of the invention have a sequence identity in the variable regions of at least 60%, more preferably, at least 70% or 80%, still more preferably at least 90% and most preferably at least 95%. Preferred antibodies also have a sequence similarity in the variable regions of at least 80%, more preferably 90% and most preferably 95%.

DNA Molecules of the Invention

The present invention also relates to uses of DNA molecules that encode an antibody for use in the invention. These sequences include, but are not limited to, those DNA molecules set forth in FIGS. 1a and 2a.

DNA molecules of the invention are not limited to the sequences disclosed herein, but also include variants thereof. DNA variants within the invention may be described by reference to their physical properties in hybridization. The skilled worker will recognize that DNA can be used to identify its complement and, since DNA is double stranded, its equivalent or homolog, using nucleic acid hybridization techniques. It also will be recognized that hybridization can occur with less than 100% complementarity. However, given appropriate choice of conditions, hybridization techniques can be used to differentiate among DNA sequences based on their structural relatedness to a particular probe. For guidance regarding such conditions see, Sambrook et al., 1989 (Sambrook, J., Fritsch, E. F. and Maniatis, T. (1989) Molecular Cloning: A laboratory manual, Cold Spring Harbor Laboratory Press, Cold Spring Harbor, USA) and Ausubel et al., 1995 (Ausubel, F. M., Brent, R., Kingston, R. E., Moore, D. D., Sedman, J. G., Smith, J. A., & Struhl, K. eds. (1995). Current Protocols in Molecular Biology. New York: John Wiley and Sons).

Structural similarity between two polynucleotide sequences can be expressed as a function of "stringency" of the conditions under which the two sequences will hybridize with one another. As used herein, the term "stringency" refers to the extent that the conditions disfavor hybridization. Stringent conditions strongly disfavor hybridization, and only the most structurally related molecules will hybridize to one another under such conditions. Conversely, non-stringent conditions favor hybridization of molecules displaying a lesser degree of structural relatedness. Hybridization stringency, therefore, directly correlates with the structural relationships of two nucleic acid sequences. The following relationships are useful in correlating hybridization and relatedness (where $T_m$ is the melting temperature of a nucleic acid duplex):

a. $T_m=69.3+0.41(G+C)\%$
b. The $T_m$ of a duplex DNA decreases by 1° C. with every increase of 1% in the number of mismatched base pairs.
c. $(T_m)_{\mu 2}-(T_m)_{\mu 1}=18.5\log_{10}\mu 2/\mu 1$ where µ1 and µ2 are the ionic strengths of two solutions.

Hybridization stringency is a function of many factors, including overall DNA concentration, ionic strength, temperature, probe size and the presence of agents which disrupt hydrogen bonding. Factors promoting hybridization include high DNA concentrations, high ionic strengths, low temperatures, longer probe size and the absence of agents that disrupt hydrogen bonding. Hybridization typically is performed in two phases: the "binding" phase and the "washing" phase.

First, in the binding phase, the probe is bound to the target under conditions favoring hybridization. Stringency is usually controlled at this stage by altering the temperature. For high stringency, the temperature is usually between 65° C. and 70° C., unless short (<20 nt) oligonucleotide probes are used. A representative hybridization solution comprises 6×SSC, 0.5% SDS, 5×Denhardt's solution and 100 µg of nonspecific carrier DNA. See Ausubel et al., section 2.9, supplement 27 (1994). Of course, many different, yet functionally equivalent, buffer conditions are known. Where the degree of relatedness is lower, a lower temperature may be chosen. Low stringency binding temperatures are between about 25° C. and 40° C. Medium stringency is between at least about 40° C. to less than about 65° C. High stringency is at least about 65° C.

Second, the excess probe is removed by washing. It is at this phase that more stringent conditions usually are applied. Hence, it is this "washing" stage that is most important in determining relatedness via hybridization. Washing solutions typically contain lower salt concentrations. One exemplary medium stringency solution contains 2×SSC and 0.1% SDS. A high stringency wash solution contains the equivalent (in ionic strength) of less than about 0.2×SSC, with a preferred stringent solution containing about 0.1×SSC. The temperatures associated with various stringencies are the same as discussed above for "binding." The washing solution also typically is replaced a number of times during washing. For example, typical high stringency washing conditions comprise washing twice for 30 minutes at 55° C. and three times for 15 minutes at 60° C.

Accordingly, the present invention includes the use of nucleic acid molecules that hybridize to the molecules of set forth in FIGS. 1a and 2a under high stringency binding and washing conditions, where such nucleic molecules encode an antibody or functional fragment thereof for uses as described herein. Preferred molecules (from an mRNA perspective) are those that have at least 75% or 80% (preferably at least 85%, more preferably at least 90% and most preferably at least 95%) homology or sequence identity with one of the DNA molecules described herein.

Functionally Equivalent Variants

Yet another class of DNA variants the use of which is within the scope of the invention may be described with reference to the product they encode (see the peptides listed in FIGS. 1b and 2b). These functionally equivalent genes are characterized by the fact that they encode the same peptide sequences found in FIGS. 1b and 2b due to the degeneracy of the genetic code.

It is recognized that variants of DNA molecules provided herein can be constructed in several different ways. For example, they may be constructed as completely synthetic DNAs. Methods of efficiently synthesizing oligonucleotides in the range of 20 to about 150 nucleotides are widely available. See Ausubel et al., section 2.11, Supplement 21 (1993). Overlapping oligonucleotides may be synthesized and assembled in a fashion first reported by Khorana et al., J. Mol. Biol. 72:209-217 (1971); see also Ausubel et al., supra, Section 8.2. Synthetic DNAs preferably are designed with convenient restriction sites engineered at the 5' and 3' ends of the gene to facilitate cloning into an appropriate vector.

As indicated, a method of generating variants is to start with one of the DNAs disclosed herein and then to conduct site-directed mutagenesis. See Ausubel et al., supra, chapter 8, Supplement 37 (1997). In a typical method, a target DNA is cloned into a single-stranded DNA bacteriophage vehicle. Single-stranded DNA is isolated and hybridized with an oligonucleotide containing the desired nucleotide alteration(s). The complementary strand is synthesized and the double stranded phage is introduced into a host. Some of the resulting progeny will contain the desired mutant, which can be confirmed using DNA sequencing. In addition, various methods are available that increase the probability that the progeny phage will be the desired mutant. These methods are well known to those in the field and kits are commercially available for generating such mutants.

Recombinant DNA Constructs and Expression

The present invention further provides for the use of recombinant DNA constructs comprising one or more of the nucleotide sequences of the present invention. The recombinant constructs are used in connection with a vector, such as a plasmid or viral vector, into which a DNA molecule encoding an antibody for use in the invention is inserted.

The encoded gene may be produced by techniques described in Sambrook et al., 1989, and Ausubel et al., 1989. Alternatively, the DNA sequences may be chemically synthesized using, for example, synthesizers. See, for example, the techniques described in OLIGONUCLEOTIDE SYNTHESIS (1984, Gait, ed., IRL Press, Oxford), which is incorporated by reference herein in its entirety. Recombinant constructs of the invention are comprised with expression vectors that are capable of expressing the RNA and/or protein products of the encoded DNA(s). The vector may further comprise regulatory sequences, including a promoter operably linked to the open reading frame (ORF). The vector may further comprise a selectable marker sequence. Specific initiation and bacterial secretory signals also may be required for efficient translation of inserted target gene coding sequences.

The present invention further provides for uses of host cells containing at least one of the DNAs disclosed herein. The host cell can be virtually any cell for which expression vectors are available. It may be, for example, a higher eukaryotic host cell, such as a mammalian cell, a lower eukaryotic host cell, such as a yeast cell, but preferably is a prokaryotic cell, such as a bacterial cell. Introduction of the recombinant construct into the host cell can be effected by calcium phosphate transfection, DEAE, dextran mediated transfection, electroporation or phage infection.

Bacterial Expression

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and, if desirable, to provide amplification within the host. Suitable prokaryotic hosts for transformation include *E. coli, Bacillus subtilis, Salmonella typh-*

*imurium* and various species within the genera *Pseudomonas, Streptomyces*, and *Staphylococcus*.

Bacterial vectors may be, for example, bacteriophage-, plasmid- or phagemid-based. These vectors can contain a selectable marker and bacterial origin of replication derived from commercially available plasmids typically containing elements of the well known cloning vector pBR322 (ATCC 37017). Following transformation of a suitable host strain and growth of the host strain to an appropriate cell density, the selected promoter is de-repressed/induced by appropriate means (e.g., temperature shift or chemical induction) and cells are cultured for an additional period. Cells are typically harvested by centrifugation, disrupted by physical or chemical means, and the resulting crude extract retained for further purification.

In bacterial systems, a number of expression vectors may be advantageously selected depending upon the use intended for the protein being expressed. For example, when a large quantity of such a protein is to be produced, for the generation of antibodies or to screen peptide libraries, for example, vectors which direct the expression of high levels of fusion protein products that are readily purified may be desirable.

Therapeutic Methods

Therapeutic methods involve administering to a subject in need of treatment a therapeutically effective amount of an antibody contemplated by the invention. A "therapeutically effective" amount hereby is defined as the amount of an antibody that is of sufficient quantity to deplete CD38-positive cells in a treated area of a subject—either as a single dose or according to a multiple dose regimen, alone or in combination with other agents, which leads to the alleviation of an adverse condition, yet which amount is toxicologically tolerable. The subject may be a human or non-human animal (e.g., rabbit, rat, mouse, monkey or other lower-order primate).

An antibody for use in the invention might be co-administered with known medicaments, and in some instances the antibody might itself be modified. For example, an antibody could be conjugated to an immunotoxin or radioisotope to potentially further increase efficacy.

Disorders and conditions particularly suitable for treatment with an antibody are multiple myeloma (MM) and other haematological diseases, such as chronic lymphocytic leukemia (CLL), chronic myelogenous leukemia (CML), acute myelogenous leukemia (AML), and acute lymphocytic leukemia (ALL). An antibody also might be used to treat inflammatory disease such as rheumatoid arthritis (RA) or systemic lupus erythematosus (SLE).

To treat any of the foregoing disorders, pharmaceutical compositions for use in accordance with the present invention may be formulated in a conventional manner using one or more physiologically acceptable carriers or excipients. An antibody for use in the invention can be administered by any suitable means, which can vary, depending on the type of disorder being treated. Possible administration routes include parenteral (e.g., intramuscular, intravenous, intraarterial, intraperitoneal, or subcutaneous), intrapulmonary and intranasal, and, if desired for local immunosuppressive treatment, intralesional administration. In addition, an antibody for use in the invention might be administered by pulse infusion, with, e.g., declining doses of the antibody. Preferably, the dosing is given by injections, most preferably intravenous or subcutaneous injections, depending in part on whether the administration is brief or chronic. The amount to be administered will depend on a variety of factors such as the clinical symptoms, weight of the individual, whether other drugs are administered. The skilled artisan will recognize that the route of administration will vary depending on the disorder or condition to be treated.

Determining a therapeutically effective amount of the novel polypeptide, according to this invention, largely will depend on particular patient characteristics, route of administration, and the nature of the disorder being treated. General guidance can be found, for example, in the publications of the International Conference on Harmonisation and in REMINGTON'S PHARMACEUTICAL SCIENCES, chapters 27 and 28, pp. 484-528 (18th ed., Alfonso R. Gennaro, Ed., Easton, Pa.: Mack Pub. Co., 1990). More specifically, determining a therapeutically effective amount will depend on such factors as toxicity and efficacy of the medicament. Toxicity may be determined using methods well known in the art and found in the foregoing references. Efficacy may be determined utilizing the same guidance in conjunction with the methods described below in the Examples.

Diagnostic Methods

CD38 is highly expressed on hematological cells in certain malignancies; thus, an anti-CD38 antibody for use in the invention may be employed in order to image or visualize a site of possible accumulation of malignant cells in a patient. In this regard, an antibody can be detectably labeled, through the use of radioisotopes, affinity labels (such as biotin, avidin, etc.) fluorescent labels, paramagnetic atoms, etc. Procedures for accomplishing such labeling are well known to the art. Clinical application of antibodies in diagnostic imaging are reviewed by Grossman, H. B., Urol. Clin. North Amer. 13:465-474 (1986)), Unger, E. C. et al., Invest. Radiol. 20:693-700 (1985)), and Khaw, B. A. et al., Science 209:295-297 (1980)). Preferred antibodies or antigen-binding regions of the invention for use as a diagnostic compound comprise a variable heavy chain sequence selected from the group consisting of SEQ ID NO: 16, 17, 18, 19, 20, 21, 22, 23, 24, 25, 26, 27, 28, 29, 30, 92, 93, 94, 95, 96, 97, 98, 99, 100, 101, 102, 103, 104, 105 and 106 and/or a variable light chain sequence selected from the group consisting of SEQ ID NO: 46, 47, 48, 49, 50, 51, 52, 53, 54, 55, 56, 57, 58, 59, 60, 109 and 110.

The detection of foci of such detectably labeled antibodies might be indicative of a site of tumor development, for example. In one embodiment, this examination is done by removing samples of tissue or blood and incubating such samples in the presence of the detectably labeled antibodies. In a preferred embodiment, this technique is done in a non-invasive manner through the use of magnetic imaging, fluorography, etc. Such a diagnostic test may be employed in monitoring the success of treatment of diseases, where presence or absence of CD38-positive cells is a relevant indicator. The invention also contemplates the use of an anti-CD38 antibody, as described herein for diagnostics in an ex vivo setting.

Therapeutic And Diagnostic Compositions

The antibodies for use in the present invention can be formulated according to known methods to prepare pharmaceutically useful compositions, wherein an antibody for use in the invention (including any functional fragment thereof) is combined in a mixture with a pharmaceutically acceptable carrier vehicle. Suitable vehicles and their formulation are described, for example, in REMINGTON'S PHARMACEUTICAL SCIENCES (18th ed., Alfonso R. Gennaro, Ed., Easton, Pa.: Mack Pub. Co., 1990). In order to form a pharmaceutically acceptable composition suitable for effective administration, such compositions will contain an effective amount of one or more of the antibodies for use in the present invention, together with a suitable amount of carrier vehicle. Preferred antibodies or antigen-binding regions of the invention for use as a diagnostic compound comprise a variable heavy chain sequence selected from the group consisting of SEQ ID NO: 16, 17, 18, 19, 20, 21, 22, 23, 24, 25, 26, 27, 28, 29, 30, 92, 93, 94, 95, 96, 97, 98, 99, 100, 101, 102, 103, 104, 105 and 106 and/or a variable light chain sequence selected from the group consisting of SEQ ID NO: 46, 47, 48, 49, 50, 51, 52, 53, 54, 55, 56, 57, 58, 59, 60, 109 and 110.

Preparations may be suitably formulated to give controlled-release of the active compound. Controlled-release preparations may be achieved through the use of polymers to complex or absorb anti-CD38 antibody. The controlled delivery may be exercised by selecting appropriate macromolecules (for example polyesters, polyamino acids, polyvinyl, pyrrolidone, ethylenevinyl-acetate, methylcellulose, carboxymethylcellulose, or protamine, sulfate) and the concentration of macromolecules as well as the methods of incorporation in order to control release. Another possible method to control the duration of action by controlled release preparations is to incorporate anti-CD38 antibody into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatine-microcapsules and poly (methylmethacylate) microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

The compounds may be formulated for parenteral administration by injection, e.g., by bolus injection or continuous infusion. Formulations for injection may be presented in unit dosage form, e.g., in ampules, or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compositions may, if desired, be presented in a pack or dispenser device, which may contain one or more unit dosage forms containing the active ingredient. The pack may for example comprise metal or plastic foil, such as a blister pack. The pack or dispenser device may be accompanied by instructions for administration.

The invention further is understood by reference to the following working examples, which are intended to illustrate and, hence, not limit the invention.

EXAMPLES

Cell-lines

The following cell-lines were obtained from the European Collection of Cell Cultures (ECACC), the German Collection of Microorganisms (DSMZ) or the American Type Culture collection (ATCC): hybridoma cell line producing the CD38 mouse IgG1 monoclonal antibody OKT10 (ECACC, #87021903), Jurkat cells (DSMZ, ACC282), LP-1 (DSMZ, ACC41), RPMI8226 (ATCC, CCL-155), HEK293 (ATCC, CRL-1573), CHO-K$^1$ (ATCC, CRL-61), Raji (ATCC, CCL-86), and OPM2 (DSMZ, ACC50).

Cells and Culture-conditions

All cells were cultured under standardized conditions at 37° C. and 5% $CO_2$ in a humidified incubator. The cell-lines LP-1, RPMI8226, Jurkat and Raji were cultured in RPMI1640 (Pan biotech GmbH, #P04-16500) supplemented with 10% FCS (PAN biotech GmbH, #P30-3302), 50 U/ml penicillin, 50 µg/ml streptomycin (Gibco, #15140-122) and 2 mM glutamine (Gibco, #25030-024) and, in case of Jurkat- and Raji-cells, additionally 10 mM Hepes (Pan biotech GmbH, #P05-01100) and 1 mM sodium pyruvate (Pan biotech GmbH, #P04-43100) had to be added.

CHO-K1 and HEK293 were grown in DMEM (Gibco, #10938-025) supplemented with 2 mM glutamine and 10% FCS. Stable CD38 CHO-K$^1$ transfectants were maintained in the presence of G418 (PAA GmbH, P11-012) whereas for HEK293 the addition of 1 mM sodium-pyruvate was essential. After transient transfection of HEK293 the 10% FCS was replaced by Ultra low IgG FCS (Invitrogen, #16250-078). The cell-line OKT10 was cultured in IDMEM (Gibco, #31980-022), supplemented with 2 mM glutamine and 20% FCS.

Preparation of Single Cell Suspensions from Peripheral Blood

All blood samples were taken after informed consent. Peripheral blood mononuclear cells (PBMC) were isolated by Histopaque®-1077 (Sigma) according to the manufacturer's instructions from healthy donors. Red blood cells were depleted from these cell suspensions by incubation in ACK Lysis Buffer (0.15 M NH4Cl, 10 mM $KHCO_3$, 0.1 M EDTA) for 5 min at RT or a commercial derivative (Bioscience, #00-4333). Cells were washed twice with PBS and then further processed for flow cytometry or ADCC (see below).

Flow cytometry ("FACS")

All stainings were performed in round bottom 96-well culture plates (Nalge Nunc) with $2 \times 10^5$ cells per well. Cells were incubated with Fab or IgG antibodies at the indicated concentrations in 50 µl FACS buffer (PBS, 3% FCS, 0.02% $NaN_3$) for 40 min at 4° C. Cells were washed twice and then incubated with R-Phycoerythrin (PE) conjugated goat-anti-human or goat-anti-mouse IgG (H+L) F(ab')$_2$ (Jackson Immuno Research), diluted 1:200 in FACS buffer, for 30 min at 4° C. Cells were again washed, resuspended in 0.3 ml FACS buffer and then analyzed by flow cytometry in a FACSCalibur (Becton Dickinson, San Diego, Calif.).

For FACS based Scatchard analyses RPMI8226 cells were stained with at 12 different dilutions (1:2$^n$) starting at 12.5 µg/ml (IgG) final concentration. At least two independent measurements were used for each concentration and $K_D$ values extrapolated from median fluorescence intensities according to Chamow et al. (1994).

Surface Plasmon Resonance

The kinetic constants $k_{on}$ and $k_{off}$ were determined with serial dilutions of the respective Fab binding to covalently immobilized CD38-Fc fusion protein using the BIAcore 3000 instrument (Biacore, Uppsala, Sweden). For covalent antigen immobilization standard EDC-NHS amine coupling chemistry was used. For direct coupling of CD38 Fc-fusion protein CM5 sensor chips (Biacore) were coated with ~600-700 RU in 10 mM acetate buffer, pH 4.5. For the reference flow cell a respective amount of HSA (human serum albumin) was used. Kinetic measurements were done in PBS (136 mM NaCl, 2.7 mM KCl, 10 mM $Na_2HPO_4$, 1.76 mM $KH_2PO_4$ pH 7.4) at a flow rate of 20 µl/min using Fab concentration range from 1.5-500 nM. Injection time for each concentration was 1 min, followed by 2 min dissociation phase. For regeneration 5 µA 10 mM HCl was used. All sensograms were fitted locally using BIA evaluation software 3.1 (Biacore).

Example 1

Antibody Generation from HuCAL Libraries

For the generation of therapeutic antibodies against CD38, selections with the MorphoSys HuCAL GOLD® phage display library were carried out. HuCAL GOLD® is a Fab library based on the HuCAL® concept (Knappik et al., 2000; Krebs et al., 2001), in which all six CDRs are diversified, and which employs the CysDisplay™ technology for linking Fab fragments to the phage surface (Löhning, 2001).

A. Phagemid Rescue, Phage Amplification and Purification

HuCAL GOLD® phagemid library was amplified in 2×TY medium containing 34 µg/ml chloramphenicol and 1% glucose (2×TY-CG). After helper phage infection (VCSM13) at an OD600 of 0.5 (30 min at 37° C. without shaking; 30 min at 37° C. shaking at 250 rpm), cells were spun down (4120 g; 5 min; 4° C.), resuspended in 2×TY/34 µg/ml chloramphenicol/50 µg/ml kanamycin and grown overnight at 22° C. Phages were PEG-precipitated from the supernatant, resuspended in PBS/20% glycerol and stored at −80° C. Phage amplification between two panning rounds was conducted as follows: mid-log phase TG1 cells were infected with eluted phages and plated onto LB-agar supplemented with 1% of glucose and 34 µg/ml of chloramphenicol (LB-CG). After overnight incubation at 30° C., colonies were scraped off, adjusted to an OD600 of 0.5 and helper phage added as described above.

B. Pannings with HuCAL GOLD®

For the selections HuCAL GOLD® antibody-phages were divided into three pools corresponding to different VH master genes (pool 1: VH1/5λκ, pool 2: VH3λκ, pool 3: VH2/4/6λκ). These pools were individually subjected to 3 rounds of whole cell panning on CD38-expressing CHO-K1 cells followed by pH-elution and a post-adsorption step on CD38-negative CHO-K$^1$-cells for depletion of irrelevant antibody-phages. Finally, the remaining antibody phages were used to infect *E. coli* TG1 cells. After centrifugation the bacterial pellet was resuspended in 2×TY medium, plated on agar plates and incubated overnight at 30° C. The selected clones were then scraped from the plates, phages were rescued and amplified. The second and the third round of selections were performed as the initial one.

The Fab encoding inserts of the selected HuCAL GOLD° phages were subcloned into the expression vector pMORPH®x9_Fab_FS (Rauchenberger et al., 2003) to facilitate rapid expression of soluble Fab. The DNA of the selected clones was digested with XbaI and EcoRI thereby cutting out the Fab encoding insert (ompA-VLCL and phoA-Fd), and cloned into the XbaI/EcoRI cut vector pMORPH®x9_Fab_FS. Fab expressed in this vector carry two C-terminal tags (FLAG™ and Strep-tag® II) for detection and purification.

Example 2

Biological Assays

Antibody dependent cellular cytotoxicity (ADCC) and complement-dependent cytotoxicity was measured according to a published protocol based on flow-cytometry analysis (Naundorf et al., 2002) as follows:

ADCC:

For ADCC measurements, target cells (T) were adjusted to 2.0E+05 cells/ml and labeled with 100 ng/ml Calcein AM (Molecular Probes, C-3099) in RPMI1640 medium (Pan biotech GmbH) for 2 minutes at room temperature. Residual calcein was removed by 3 washing steps in RPMI1640 medium. In parallel PBMC were prepared as source for (natural killer) effector cells (E), adjusted to 1.0E+07 and mixed with the labeled target cells to yield a final E:T-ratio of 50:1 or less, depending on the assay conditions. Cells were washed once and the cell-mix resuspended in 200 µl RPMI1640 medium containing the respective antibody at different dilutions. The plate was incubated for 4 hrs under standardized conditions at 37° C. and 5% $CO_2$ in a humidified incubator. Prior to FACS analysis cells were labeled with propidium-iodide (PI) and analyzed by flow-cytometry (Becton-Dickinson). Between 50.000 and 150.000 events were counted for each assay.

The following equation gave rise to the killing activity [in %]:

$$\frac{ED^A}{EL^A + ED^A} \times 100$$

with $ED^A$=events dead cells (calcein+PI stained cells), and $EL^A$=events living cells (calcein stained cells)

CDC:

For CDC measurements, 5.0E+04 CD38 CHO-K1 transfectants were added to a microtiter well plate (Nunc) together with a 1:4 dilution of human serum (Sigma, #S-1764) and the respective antibody. All reagents and cells were diluted in RPMI1640 medium (Pan biotech GmbH) supplemented with 10% FCS. The reaction-mix was incubated for 2 hrs under standardized conditions at 37° C. and 5% $CO_2$ in a humidified incubator. As negative controls served either heat-inactivated complement or CD38-transfectants without antibody. Cells were labeled with PI and subjected to FACS-analysis.

In total 5000 events were counted and the number of dead cells at different antibody concentrations used for the determination of EC50 values. The following equation gave rise to the killing activity [in %]:

$$\frac{ED^C}{EL^C + ED^C} \times 100$$

with $ED^C$=events dead cells (PI stained cells), and $EL^C$=events living cells (unstained)

Cytotoxicity values from a total of 12 different antibody-dilutions (1:2$^n$) in triplicates were used in ADCC and duplicates in CDC for each antibody in order obtain EC-50 values with a standard analysis software (PRISM®, Graph Pad Software).

Example 3

Generation of Stable CD38-transfectants and CD38 Fc-fusion Proteins

In order to generate CD38 protein for panning and screening two different expression systems had to be established. The first strategy included the generation of CD38-Fc-fusion protein, which was purified from supernatants after transient transfection of HEK293 cells. The second strategy involved the generation of a stable CHO-K1-cell line for high CD38 surface expression to be used for selection of antibody-phages via whole cell panning.

As an initial step Jurkat cells (DSMZ ACC282) were used for the generation of cDNA (Invitrogen) followed by amplification of the entire CD38-coding sequence using primers complementary to the first 7 and the last 9 codons of CD38, respectively (primer MTE001 & MTE002rev; Table 4). Sequence analysis of the CD38-insert confirmed the published amino acid sequence by Jackson et al. (1990) except for position 49 which revealed a glutamine instead of a tyrosine as described by Nata et al. (1997). For introduction of restriction endonuclease sites and cloning into different derivatives of expression vector pcDNA3.1 (Stratagene), the purified PCR-product served as a template for the re-amplification of the entire gene (primers MTE006 & MTE007rev, Table 4) or a part (primers MTE004 & MTE009rev, Table 4) of it. In the latter case a fragment encoding for the extracellular domain (aa 45 to 300) was amplified and cloned in frame between a human Vkappa leader sequence and a human Fc-gamma 1 sequence. This vector served as expression vector for the generation of soluble CD38-Fc fusion-protein. Another pcDNA3.1-derivative without leader-sequence was used for insertion of the CD38 full-length gene. In this case a stop codon in front of the Fc-coding region and the missing leader-sequence gave rise to CD38-surface expression. HEK293 cells were transiently transfected with the Fc-fusion protein vector for generation of soluble CD38 Fc-fusion protein and, in case of the full-length derivative, CHO-K1-cells were transfected for the generation of a stable CD38-expressing cell line.

determined by a kinetic LAL based assay (Cambrex European Endotoxin Testing Service, Belgium).

Example 5

Generation and Production of Chimeric OKT10 (chOKT10; SEQ ID NOS: 72 and 73)

For the construction of chOKT10 the mouse VH and VL regions were amplified by PCR using cDNA prepared from the murine OKT10 hybridoma cell line (ECACC #87021903). A set of primers was used as published (Dattamajumdar et al., 1996; Zhou et al., 1994). PCR products were used for Topo-cloning (Invitrogen; pCR11-vector) and single colonies subjected to sequence analysis (M13 reverse primer) which revealed two different kappa light chain sequences and one heavy chain sequence. According to sequence alignments (EMBL-nucleotide sequence database) and literature (Krebber et al, 1997) one of the kappa-sequence belongs to the intrinsic repertoire of the tumor cell fusion partner X63Ag8.653 and hence does not belong to OKT10 antibody. Therefore, only the new kappa sequence and the single VH-fragment was used for further cloning. Both fragments were reamplified for the addition of restriction endonuclease sites followed by cloning into the respective pMOR-

TABLE 4

| Primer # | Sequence (5'->3') |
|---|---|
| MTE001 | ATG GCC AAC TGC GAG TTC AGC (SEQ ID NO: 123) |
| MTE002rev | TCA GAT CTC AGA TGT GCA AGA TGA ATC (SEQ ID NO: 124) |
| MTE004 | TT GGT ACC AGG TGG CGC CAG CAG TG (SEQ ID NO: 125) |
| MTE006 | TT GGT ACC ATG GCC AAC TGC GAG (SEQ ID NO: 126) |
| MTE007rev | CCG ATA TCA* GAT CTC AGA TGT GCA AGA TG (SEQ ID NO: 127) |
| MTE009rev | CCG ATA TC   GAT CTC AGA TGT GCA AGA TG (SEQ ID NO: 128) |

*leading to a stop codon (TGA) in the sense orientation.

Example 4

Cloning, Expression and Purification of HuCAL® IgG1

In order to express full length IgG, variable domain fragments of heavy (VH) and light chains (VL) were subcloned from Fab expression vectors into appropriate pMORPH®_hIg vectors (see FIGS. 7 to 9). Restriction endonuclease pairs BlpI/MfeI (insert-preparation) and BlpI/EcoRI (vector-preparation) were used for subcloning of the VH domain fragment into pMORPH®_hIgG1. Enzyme-pairs EcoRV/HpaI (lambda-insert) and EcoRV/BsiWI (kappa-insert) were used for subcloning of the VL domain fragment into the respective pMORPH®_hIgκ_1 or pMORPH®_h_Igλ_1 vectors. Resulting IgG constructs were expressed in HEK293 cells (ATCC CRL-1573) by transient transfection using standard calcium phosphate-DNA coprecipitation technique.

IgGs were purified from cell culture supernatants by affinity chromatography via Protein A Sepharose column. Further down stream processing included a buffer exchange by gel filtration and sterile filtration of purified IgG. Quality control revealed a purity of >90% by reducing SDS-PAGE and >90% monomeric IgG as determined by analytical size exclusion chromatography. The endotoxin content of the material was PHO IgG1-expression vectors. The sequences for the heavy chain (SEQ ID NO: 72) and light chain (SEQ ID NO: 73) are given in FIG. 6. HEK293 cells were transfected transiently and the supernatant analyzed in FACS for the chimeric OKT10 antibody binding to the CD38 over-expressing Raji cell line (ATCC).

Example 6

Cross Reactivity Analysis by FACS (MOR 03087 and MOR 03088)

1. Materials and Methods:

FIGS. 11 and 12 show FACS analyses of lymphocytes and erythrocytes: EDTA-treated blood samples were obtained from healthy humans (after obtaining informed consent) and from non human primates (Rhesus, Cynomolgus and Marmoset) and were subjected to density gradient centrifugation using the Histopaque cell separation system according to the instructions of the supplier (Sigma). For FACS-analysis, cells from the interphase (PBMC-fraction) and pellet (Erythrocyte-fraction) were incubated with anti-CD38 HuCAL® antibodies in different formats An overview of cross reactivity profiles of different anti CD38 antibodies is shown in FIG.

2. Summary and Conclusion:

The results show that among all CD38 antibodies only MOR03087 and MOR03088 showed cross-reactivity to marmoset PBMCs. Surprisingly, CD38-expression on marmoset erythrocytes is almost not detectable as compared to the strong expression on cynomolgus and rhesus erythrocytes. Thus, the CD38 expression on marmoset erythrocytes and PBMCs is more reflecting the human situation, where CD38 expression is low on erythrocytes and moderate to high on PBMCs. Marmoset is therefore considered to be suited as a model to study toxicity of molecules binding to CD38.

Based on the above study, it was decided to further optimize the binders MOR 03087 and MOR 03088, as described elsewhere in the specification, see e.g. paragraph relating to "Antibodies for use in the invention". A person skilled in the art would expect that also the derivative antibodies of the parentals would show a comparable cross reactivity profile.

REFERENCES

Antonelli, A., Baj., G., Marchetti., P., Fallahi, P., Surico, N., Pupilli, C., Malavasi, F., Ferrannini, P. (2001). Human anti-CD38 autoantibodies raise intracellular calcium and stimulate insulin release in human pancreatic islets. Diabetes 50: 985-991

Ausiello C. M., Urbani F., Lande R., la Sala A., Di Carlo B., Baj G., Surico N., Hilgers J., Deaglio S., Funaro A., Malavasi F. (2000) Functional topography of discrete domains of human CD38. Tissue Antigens. 2000 December; 56(6): 539-47.

Chamow, S. M., Zhang, D. Z., Tan, X. Y, Mathre, S. M., Marsters, S. A., Peers, D. H., Byrn, R. A., Ashknazi, A., Junghans, R. P (1994). humanized, bispecific immunoadhesin-antibody that retargets CD3+ effectors to kill HIV-1-infected cells. J. Immunol. 1994 Nov. 1; 153(9):4268-80

Dattamajumdar, A. K., Jacobsen, D. P., Hood, L. E., Osman, G. E. (1996). Rapid cloning of rearranged mouse immunoglobulin variable genes. Immunogentetics 43, 141-151

Ellis J. H., Barber, K. A., Tutt, A., Hale, C., Lewis, A. P., Glennie, M. J., Stevenson, G. T., and Crowe, J. (1995). Engineered anti-CD38 monoclonal antibodies for immunotherapy of multiple myeloma. J. Immunol. 155:925-937.

Ferrero, E., Orciani, M., Vacca, P., Ortolan, E., Crovella, S., Titti, F., Saccucci, F., Malavasi, F. (2004). Characterization and phylogenetic epitope mapping of CD38 ADPR cyclase in the cynomolgus macaque. BMC Immunology 5:21

Flavell, D. J., Boehm, D. A., Noss, A., Warnes, S. L., and Flavell, S. U. Therapy of human T-cell acute lymphoblastic leukaemia with a combination of anti-CD7 and anti-CD38-saporin immunotoxins is significantly better than therapy with each individual immunotoxin, Br. J. Cancer. 84:571-578 (2001).

Funaro, A., Spagnoli, G. C., Ausiello, C. M., Alessio, M., Roggero, S., Delia, D., Zaccolo, M., and Malavasi, F. (1990) Involvement of the multilineage CD38 molecule in a unique pathway of cell activation and proliferation. J. Immunol. 145, 2390-2396.

Golay, J., Zaffaroni, Luisella, Vaccari, T., Lazzari, M., Borleri, G.-M., Bernasconi, S., Tedesco, F., Rambaldi, Al, Introna, M. (2000). Biological response of B lymphoma to anti-CD20 monoclonal antibody in vitro: CD55 and CD59 regulate complement-mediated cell lysis. Blood 95: 3900-3908.

Hayashi, T., Treon, S. P., Hideshima, T., Tai, Y-T., Akiyama, M., Richardson, R., Chauhan, D., Grewal, I. S., Anderson, K. C. (2003). Recombinant humanized anti-CD40 monoclonal antibody triggers autologous antibody-dependent cell-mediated cytotoxicity against multiple myeloma. Br. J. Heamatol. 121, 592-596.

Hoshino S., Kukimoto I., Kontani K., Inoue S., Kanda Y., Malavasi F., Katada T. (1997) Mapping of the catalytic and epitopic sites of human CD38/NAD+ glycohydrolase to a functional domain in the carboxyl terminus. J. Immunol. 158(2):741-7.

Jackson D. G., Bell J. I. (1990) Isolation of a cDNA encoding the human CD38 (T10) molecule, a cell surface glycoprotein with an unusual discontinuous pattern of expression during lymphocyte differentiation. J. Immunol. 144(7): 2811-5.

Knappik, A., Ge, L., Honegger, A., Pack, P., Fischer, M., Wellnhofer, G., Hoess, A., Wolle, J., Pluckthun, A., and Virnekas, B. (2000). Fully synthetic human combinatorial antibody libraries (HuCAL) based on modular consensus frameworks and CDRs randomized with trinucleotides. J Mol Biol 296, 57-86.

Kono, K., Takahashi, A., Ichihara, F., Sugai, H., Fujii, H., and Matsumoto, Y. (2002). Impaired antibody-dependent cellular cytotoxicity mediated by Herceptin in patients with gastric cancer. Cancer Res. 62, 5813-5817.

Konopleva M., Estrov Z., Zhao S., Andreeff M., Mehta K. (1998) Ligation of cell surface CD38 protein with agonistic monoclonal antibody induces a cell growth signal in myeloid leukemia cells. J. Immunol. 161(9):4702-8.

Krebber, A., Bornhauser, S., Burmester, J., Honegger, A., Willuda, J., Bossard, H. R., Plückthun, A. (1997). Reliable cloning of functional antibody variable domains from hybridomas and spleen cell repertoires employing a reengineered phage display system. J. Imm. Meth. 201, 35-55.

Krebs, B., Rauchenberger, R., Reiffert, S., Rothe, C., Tesar, M., Thomassen, E., Cao, M., Dreier, T., Fischer, D., Hoss, A., Inge, L., Knappik, A., Marget, M., Pack, P., Meng, X. Q., Schier, R., Sohlemann, P., Winter, J., Wolle, J., and Kretzschmar, T. (2001). High-throughput generation and engineering of recombinant human antibodies. J Immunol Methods 254, 67-84.

Löhning, C. (2001). Novel methods for displaying (poly) peptides/proteins on bacteriophage particles via disulfide bonds. WO 01/05950.

Malavasi, F., Caligaris-Cappio, F., Milanese, C., Dellabona, P., Richiardi, P., Carbonara, A. O. (1984). Characterization of a murine monoclonal antibody specific for human early lymphohemopoietic cells. Hum. Immunol. 9: 9-20

Maloney, D. G., Smith, B., and Rose, A. (2002). Rituximab: Mechanism of Action and Resistance. Sem. Oncol. 29, 2-9.

Marchetti, P., Antonelli, A., Lupi, R., Marselli, L., Fallahi, P., Nesti, C., Baj, G., Ferrannini, E. (2002). Prolonged in vitro exposure to autoantibodies against CD38 impairs the function and survival of human pancreatic islets. Diabetes 51, 474-477.

Mehta, K., Ocanas, L., Malavasi, f., Marks; J. W., Rosenblum, M. G (2004). Retinoic acid-induced CD38 antigen as a target for immunotoxin-mediated killing of leukemia cells. Mol. Cancer. Ther. 3, 345-352

Namba, M., Otsuki, T., Mori, M., Togawa, A., Wada, H., Sugihara, T., Yawata, Y., Kimoto, T. (1989). Establishment of five human myeloma cell lines. In Vitro Cell Dev. Biol. 25: 723.

Nata K., Takamura T., Karasawa T., Kumagai T., Hashioka W., Tohgo A., Yonekura H., Takasawa S., Nakamura S., Okamoto H. (1997). Human gene encoding CD38 (ADP-ribosyl cyclase/cyclic ADP-ribose hydrolase): organization, nucleotide sequence and alternative splicing. Gene 186(2):285-92.

Naundorf, S., Preithner, S., Mayer, P., Lippold, S., Wolf, A., Hanakam, F., Fichtner, I., Kufer, P., Raum, T., Riethmüller, G., Baeuerle, P. A., Dreier, T. (2002). Int. J. Cancer 100, 101-110.

Plückthun A, and Pack P. (1997) New protein engineering approaches to multivalent and bispecific antibody fragments. Immunotechnology 3(2):83-105.

Rauchenberger R., Borges E., Thomassen-Wolf E., Rom E., Adar R., Yaniv Y., Malka M., Chumakov I., Kotzer S., Resnitzky D., Knappik A., Reiffert S., Prassler J., Jury K., Waldherr D., Bauer S., Kretzschmar T., Yayon A., Rothe C. (2003). Human combinatorial Fab library yielding specific and functional antibodies against the human fibroblast growth factor receptor 3. J Biol. Chem. 278(40):38194-205.

Reff, M. E., Carner, K., Chambers, K. S., Chinn, P. C., Leonard, J. E., Raab, R., Newman, R. A., Hanna, N., Anderson, D. R. (1994). Depletion of B cells in vivo by a chimeric mouse human monoclonal antibody to CD20. Blood 83: 435-445

Santin, A. D., Bellone, S., Gokden, M., Palmieri, M., Dunn, D., Agha, J., Roman, J. J., Hutchins, L., Pecorelli, S., O'Brian, T., Cannon, M. J., Parham, G. P. (2002). Overexpression of HER-2/Neu in Uterine serous papillary cancer. Cl. Cancer Res. 8: 1271-1279.

Shinkawa, T., Nakamura, K., Yamane, N., Shoji-Hosaka, E., Kanda, Y., Sakurada, M., Uchida, K., Anazawa, H., Satoh, M., Yamasaki, M., Hanai, N., Shitara, K. (2003). The absence of fucose but Not the presence of galactose or bisectin N-Acteylglucosamine of human IgG1 complex-type oligoscaccharides shows the critical role of enhancing antibody-dependent cellular cytotoxicity. J. Biol. Chem. 278, 3466-3473.

Zhou, H., Fisher, R. J., Papas, T. S. (1994). Optimization of primer sequences for mouse scFv repertoire display library construction. Nucleic Acids Res. 22: 888-889.

The invention claimed is:

1. An isolated nucleic acid encoding an antibody or antigen-binding fragment thereof that binds to CD38, comprising the nucleic acid sequences encoding the three variable heavy chain complementarity determining regions (H-CDRs) and the nucleic acid sequences encoding the three variable light-chain complementarity determining regions (L-CDRs) in the nucleic acid sequences encoding a variable heavy chain and a variable light chain pair selected from:
(i) SEQ ID NO: 3 and 33;
(ii) SEQ ID NO: 5 and 35;
(iii) SEQ ID NO: 6 and 36;
(iv) SEQ ID NO: 7 and 37; and
(v) SEQ ID NO: 10 and 40.

2. The isolated nucleic acid of claim 1, comprising the nucleic acid sequences encoding the three H-CDRs in SEQ ID NO: 3, and the nucleic acid sequences encoding the three L-CDRs in SEQ ID NO: 33.

3. The isolated nucleic acid of claim 1, comprising the nucleic acid sequences encoding the three H-CDRs in SEQ ID NO: 5, and the nucleic acid sequences encoding the three L-CDRs in SEQ ID NO: 35.

4. The isolated nucleic acid of claim 1, comprising the nucleic acid sequences encoding the three H-CDRs in SEQ ID NO: 6, and the nucleic acid sequences encoding the three L-CDRs in SEQ ID NO: 36.

5. The isolated nucleic acid of claim 1, comprising the nucleic acid sequences encoding the three H-CDRs in SEQ ID NO: 7, and the nucleic acid sequences encoding the three L-CDRs in SEQ ID NO: 37.

6. The isolated nucleic acid of claim 1, comprising the nucleic acid sequences encoding the three H-CDRs in SEQ ID NO: 10, and the nucleic acid sequences encoding the three L-CDRs in SEQ ID NO: 40.

7. The isolated nucleic acid of claim 1, comprising a nucleic acid sequence encoding a variable heavy chain, said nucleic acid sequence encoding the framework regions of the variable heavy chain being at least 80% identical to SEQ ID NO: 3, 5, 6, 7, or 10.

8. The isolated nucleic acid of claim 7, comprising a nucleic acid sequence encoding a variable heavy chain, said nucleic acid sequence encoding the framework regions of the variable heavy chain being at least 90% identical to SEQ ID NO: 3, 5, 6, 7, or 10.

9. The isolated nucleic acid of claim 8, comprising SEQ ID NO: 3, 5, 6, 7, or 10.

10. The isolated nucleic acid of claim 1, comprising a nucleic acid sequence encoding a variable light chain, said nucleic acid sequence encoding the framework regions of the variable light chain being at least 80% identical to SEQ ID NO: 33, 35, 36, 37, or 40.

11. The isolated nucleic acid of claim 10, comprising a nucleic acid sequence encoding a variable light chain, said nucleic acid sequence encoding the framework regions of the variable light chain being at least 90% identical to SEQ ID NO: 33, 35, 36, 37, or 40.

12. The isolated nucleic acid of claim 11, comprising SEQ ID NO: 33, 35, 36, 37,or 40.

13. The isolated nucleic acid of claim 4, comprising a nucleic acid sequence encoding a variable heavy chain, said nucleic acid sequence encoding the framework regions of the variable heavy chain being at least 80% identical to SEQ ID NO: 6.

14. The isolated nucleic acid of claim 13, comprising a nucleic acid sequence encoding a variable heavy chain, said nucleic acid sequence encoding the framework regions of the variable heavy chain being at least 90% identical to SEQ ID NO: 6.

15. The isolated nucleic acid of claim 14, comprising SEQ ID NO: 6.

16. The isolated nucleic acid of claim 5, comprising a nucleic acid sequence encoding a variable heavy chain, said nucleic acid sequence encoding the framework regions of the variable heavy chain being at least 80% identical to SEQ ID NO: 7.

17. The isolated nucleic acid of claim 16, comprising a nucleic acid sequence encoding a variable heavy chain, said nucleic acid sequence encoding the framework regions of the variable heavy chain being at least 90% identical to SEQ ID NO: 7

18. The isolated nucleic acid of claim 17, comprising SEQ ID NO: 7.

19. The isolated nucleic acid of claim 4, comprising a nucleic acid sequence encoding a variable light chain, said nucleic acid sequence encoding the framework regions of the variable light chain being at least 80% identical to SEQ ID NO: 36.

20. The isolated nucleic acid of claim 19, comprising a nucleic acid sequence encoding a variable light chain, said nucleic acid sequence encoding the framework regions of the variable light chain being at least 90% identical to SEQ ID NO: 36.

21. The isolated nucleic acid of claim 20, comprising SEQ ID NO: 36.

22. The isolated nucleic acid of claim 5, comprising a nucleic acid sequence encoding a variable light chain, said nucleic acid sequence encoding the framework regions of the variable light chain being at least 80% identical to SEQ ID NO: 37.

23. The isolated nucleic acid of claim 22, comprising a nucleic acid sequence encoding a variable light chain, said nucleic acid sequence encoding the framework regions of the variable light chain being at least 90% identical to SEQ ID NO: 37.

24. The isolated nucleic acid of claim 23, comprising SEQ ID NO: 37.

25. The isolated nucleic acid of claim 1, comprising a nucleic acid sequence pair encoding a heavy and light chain pair, said nucleic acid sequence pair encoding the framework regions of the heavy and light chain pair having at least 80% identity to the pairs selected from: (i) SEQ ID NO: 3 and 33; (ii) SEQ ID NO: 5 and 35; (iii) SEQ ID NO: 6 and 36; (iv) SEQ ID NO: 7 and 37; and (v) SEQ ID NO: 10 and 40.

26. The isolated nucleic acid of claim 1, comprising a nucleic acid sequence pair encoding a heavy and light chain pair, said nucleic acid sequence pair encoding the framework regions of the heavy and light chain pair having at least 90% identity to the pairs selected from: (i) SEQ ID NO: 3 and 33; (ii) SEQ ID NO: 5 and 35; (iii) SEQ ID NO: 6 and 36; (iv) SEQ ID NO: 7 and 37; and (v) SEQ ID NO: 10 and 40.

27. The isolated nucleic acid of claim 1, comprising SEQ ID NO: 3 and SEQ ID NO: 33.

28. The isolated nucleic acid of claim 1, comprising SEQ ID NO: 5 and SEQ ID NO: 35.

29. The isolated nucleic acid of claim 25, comprising a nucleic acid sequence encoding a heavy chain, said nucleic acid sequence encoding the framework regions of the heavy chain being at least 80% identical to SEQ ID NO: 6, and a nucleic acid sequence encoding a light chain, said nucleic acid sequence encoding the framework regions of the light chain being at least 80% identical to SEQ ID NO: 36.

30. The isolated nucleic acid of claim 26, comprising a nucleic acid sequence encoding the heavy chain, said nucleic acid sequence encoding the framework regions of the heavy chain being at least 90% identical to SEQ ID NO: 6, and a nucleic acid sequence encoding the light chain, said nucleic acid sequence encoding the framework regions of the light chain being at least 90% identical to SEQ ID NO: 36.

31. The isolated nucleic acid of claim 1, comprising SEQ ID NO: 6 and SEQ ID NO: 36.

32. The isolated nucleic acid of claim 25, comprising a nucleic acid sequence encoding the heavy chain, said nucleic acid sequence encoding the framework regions of the heavy chain being at least 80% identical to SEQ ID NO: 7, and a nucleic acid sequence encoding the light chain, said nucleic acid sequence encoding the framework regions of the light chain being at least 80% identical to SEQ ID NO: 37.

33. The isolated nucleic acid of claim 26, comprising a nucleic acid sequence encoding a heavy chain, said nucleic acid sequence encoding the framework regions of the heavy chain being at least 90% identical to SEQ ID NO:7, and a nucleic acid sequence encoding a light chain, said nucleic acid sequence encoding the framework regions of the light chain being at least 90% identical to SEQ ID NO: 37.

34. The isolated nucleic acid of claim 1, comprising SEQ ID NO: 7 and SEQ ID NO: 37.

35. The isolated nucleic acid of claim 1, comprising SEQ ID NO: 10 and SEQ ID NO: 40.

36. The isolated nucleic acid of claim 1, encoding an scFv, Fab or F(ab)$_2$ fragment.

37. The isolated nucleic acid of claim 1, encoding an IgG.

38. The isolated nucleic acid of claim 37, encoding IgGl.

39. A vector comprising the isolated nucleic acid of claim 1.

40. A cultured cell, comprising the vector of claim 39.

* * * * *

SEQUENCE LISTING

```
<160> NUMBER OF SEQ ID NOS: 139

<210> SEQ ID NO 1
<211> LENGTH: 363
<212> TYPE: DNA
<213> ORGANISM: Homo sapiens

<400> SEQUENCE: 1
caggtgcaat tggttcagtc tggcgcggaa gtgaaaaaac cgggcagcag cgtgaaagtg      60
agctgcaaag cctccggagg cacttttttct tctaatgcta tttcttgggt gcgccaagcc     120
cctgggcagg gtctcgagtg gatgggcaat atctggccga tttttggcac tgcgaattac     180
gcgcagaagt ttcagggccg ggtgaccatt accgcggatg aaagcaccag caccgcgtat     240 atgaactga gcagcctgcg tagcgaagat acggccgtgt attattgcgc gcgtaatggt     300
tatcttgata ctaatactta tattgattat tggggccaag gcaccctggt gacggttagc     360
tca                                                                    363

<210> SEQ ID NO 2
<211> LENGTH: 360
<212> TYPE: DNA
<213> ORGANISM: Homo sapiens

<400> SEQUENCE: 2
caggtgcaat tggtggaaag cggcggcggc ctggtgcaac cgggcggcag cctgcgtctg      60
agctgcgcgg cctccggatt tacctttttct gattatgcta tgtcttgggt gcgccaagcc     120
cctgggaagg gtctcgagtg ggtgagcgct atccgttatg atggtagcaa tacctattat     180
gcggatagcg tgaaaggccg ttttaccatt tcacgtgata attcgaaaaa caccctgtat     240
ctgcaaatga acagcctgcg tgcggaagat acggccgtgt attattgcgc gcgttattat     300
tctggtattt atcagcatat tgattattgg ggccaaggca ccctggtgac ggttagctca     360

<210> SEQ ID NO 3
<211> LENGTH: 369
<212> TYPE: DNA
<213> ORGANISM: Homo sapiens

<400> SEQUENCE: 3
caggtgcaat tggtggaaag cggcggcggc ctggtgcaac cgggcggcag cctgcgtctg      60
```

```
agctgcgcgg cctccggatt tacctttcct tcttatgctc ttcattgggt gcgccaagcc    120
cctgggaagg gtctcgagtg ggtgagctct atctctggtc ttggtagcac tacctattat    180
gcggatagcg tgaaaggccg ttttaccatt tcacgtgata attcgaaaaa caccctgtat    240
ctgcaaatga acagcctgcg tgcggaagat acggccgtgt attattgcgc gcgttatcat    300
tatgagtatc attattttc ttctggtttt gataattggg gccaaggcac cctggtgacg    360
gttagctca                                                            369

<210> SEQ ID NO 4
<211> LENGTH: 351
<212> TYPE: DNA
<213> ORGANISM: Homo sapiens

<400> SEQUENCE: 4
caggtgcaat tggttcagag cggcgcggaa gtgaaaaaac cgggcgcgag cgtgaaagtg     60
agctgcaaag cctccggata tacctttact ggttattata ttaattgggt ccgccaagcc    120
cctgggcagg gtctcgagtg gatgggctgg atctttccga atggtggctc tacgggttac    180
gcgcagaagt tcagggccg ggtgaccatg acccgtgata ccagcattag caccgcgtat    240
atggaactga gcagcctgcg tagcgaagat acggccgtgt attattgcgc gcgtggtaat    300
atttttattt ttgattattg gggccaaggc accctggtga cggttagctc a             351

<210> SEQ ID NO 5
<211> LENGTH: 360
<212> TYPE: DNA
<213> ORGANISM: Homo sapiens

<400> SEQUENCE: 5
caggtgcaat tggtggaaag cggcggcggc ctggtgcaac cgggcggcag cctgcgtctg     60
agctgcgcgg cctccggatt tacctttact tcttattata tgcattgggt gcgccaagcc    120
cctgggaagg gtctcgagtg ggtgagctat atcgattctt ctggtagctc tacctattat    180
gcggatagcg tgaaaggccg ttttaccatt tcacgtgata attcgaaaaa caccctgtat    240
ctgcaaatga acagcctgcg tgcggaagat acggccgtgt attattgcgc gcgtcagctt    300
atgccttttg gtggttattt tgatgtttgg ggccaaggca ccctggtgac ggttagctca    360

<210> SEQ ID NO 6
<211> LENGTH: 360
<212> TYPE: DNA
<213> ORGANISM: Homo sapiens

<400> SEQUENCE: 6
caggtgcaat tggtggaaag cggcggcggc ctggtgcaac cgggcggcag cctgcgtctg     60
agctgcgcgg cctccggatt taccttttct tcttattata tgaattgggt gcgccaagcc    120
cctgggaagg gtctcgagtg ggtgagcggt atctctggtg atcctagcaa tacctattat    180
gcggatagcg tgaaaggccg ttttaccatt tcacgtgata attcgaaaaa caccctgtat    240
ctgcaaatga acagcctgcg tgcggaagat acggccgtgt attattgcgc gcgtgatctt    300
cctcttgttt atactggttt tgcttattgg ggccaaggca ccctggtgac ggttagctca    360

<210> SEQ ID NO 7
<211> LENGTH: 363
<212> TYPE: DNA
<213> ORGANISM: Homo sapiens
```

<400> SEQUENCE: 7

```
caggtgcaat tggtggaaag cggcggcggc ctggtgcaac cgggcggcag cctgcgtctg      60
agctgcgcgg cctccggatt tacctttttct tcttatgcta tgaattgggt gcgccaagcc    120
cctgggaagg gtctcgagtg ggtgagcggt atctcttctt ggggtagctc tacctattat    180
gcggatagcg tgaaaggccg ttttaccatt tcacgtgata attcgaaaaa caccctgtat    240
ctgcaaatga acagcctgcg tgcggaagat acggccgtgt attattgcgc gcgtgaggat    300
ggttcttata tgactgatta ttttgcttat tggggccaag caccctggt gacggttagc     360
tca                                                                  363
```

<210> SEQ ID NO 8
<211> LENGTH: 372
<212> TYPE: DNA
<213> ORGANISM: Homo sapiens

<400> SEQUENCE: 8

```
caggtgcaat tgaaagaaag cggcccggcc ctggtgaaac cgacccaaac cctgaccctg    60
acctgtacct tttccggatt tagcctgtct tctgatggta tgggtgtggg ttggattcgc   120
cagccgcctg ggaaagccct cgagtggctg gctcttatcg attgggatga tgataagcgt   180
tatagcacca gcctgaaaac gcgtctgacc attagcaaag atacttcgaa aaatcaggtg   240
gtgctgacta tgaccaacat ggacccggtg gatacggcca ctattattg cgcgcgtttt   300
aattggtttt atcgtcttgc ttttgttaat cctgatgttt ggggccaagg caccctggtg   360
acggttagct ca                                                         372
```

<210> SEQ ID NO 9
<211> LENGTH: 366
<212> TYPE: DNA
<213> ORGANISM: Homo sapiens

<400> SEQUENCE: 9

```
caggtgcaat tgaaagaaag cggcccggcc ctggtgaaac cgacccaaac cctgaccctg    60
acctgtacct tttccggatt tagcctgtct acttctcgtg ttggtgtgtc ttggattcgc   120
cagccgcctg ggaaagccct cgagtggctg gctcatatcg attggaatga tgataagtat   180
tatagcacca gcctgaaaac gcgtctgacc attagcaaag atacttcgaa aaatcaggtg   240
gtgctgacta tgaccaacat ggacccggtg gatacggcca ctattattg cgcgcgtgag   300
gatcgtcttc ttggtggtta tggttatgat gtttggggcc aaggcaccct ggtgacggtt   360
agctca                                                                366
```

<210> SEQ ID NO 10
<211> LENGTH: 360
<212> TYPE: DNA
<213> ORGANISM: Homo sapiens

<400> SEQUENCE: 10

```
caggtgcaat tgcaagaaag tggtccgggc ctggtgaaac cgggcgaaac cctgagcctg    60
acctgcaccg tttccggagg cagcatttct ggtaattatt ggtctggat tcgccaggcc   120
cctgggaagg gtctcgagtg gattggcgat tatcatggct ctacctatta taatccgagc   180
ctgaaaggcc gggtgaccat tagcgttgat acttcgaaaa accagtttag cctgaaactg   240
agcagcgtga cggcggaaga tacggccgtg tattattgcg cgcgtgagca gtatcattgg   300
ggtcttgctt ggactggttt tgataattgg ggccaaggca ccctggtgac ggttagctca   360
```

<210> SEQ ID NO 11
<211> LENGTH: 354
<212> TYPE: DNA
<213> ORGANISM: Homo sapiens

<400> SEQUENCE: 11

```
caggtgcaat tggttcagag cggcgcggaa gtgaaaaaac cgggcgaaag cctgaaaatt      60
agctgcaaag gttccggata ttccttttct acttcttggg ttggttgggt gcgccagatg     120
cctgggaagg gtctcgagtg gatgggcatt atcgatccgg atattagcta tacctcttat     180
tctccgagct ttcagggcca ggtgaccatt agcgcggata aaagcattag caccgcgtat     240
cttcaatgga gcagcctgaa agcgagcgat acggccatgt attattgcgc gcgttatctt     300
atgggtcttg ttatgatgt ttggggccaa ggcaccctgg tgacggttag ctca            354
```

<210> SEQ ID NO 12
<211> LENGTH: 363
<212> TYPE: DNA
<213> ORGANISM: Homo sapiens

<400> SEQUENCE: 12

```
caggtgcaat tgaaagaaag cggcccggcc ctggtgaaaac cgacccaaac cctgaccctg      60
acctgtacct tttccggatt tagcctgtct tcttctggta tgtctgtgtc ttggattcgc     120
cagccgcctg ggaaagccct cgagtggctg gctcgtatct attctgatga ttctaagtct     180
tatagcacca gcctgaaaac gcgtctgacc attagcaaag atacttcgaa aaatcaggtg     240
gtgctgacta tgaccaacat ggacccggtg atacggcca cctattattg cgcgcgtgct     300
gctcattgga atggtcctct ttttgatgtt tggggccaag gcaccctggt gacggttagc     360
tca                                                                   363
```

<210> SEQ ID NO 13
<211> LENGTH: 351
<212> TYPE: DNA
<213> ORGANISM: Homo sapiens

<400> SEQUENCE: 13

```
caggtgcaat tggtggaaag cggcggcggc ctggtgcaac cgggcggcag cctgcgtctg      60
agctgcgcgg cctccggatt tacctttcct aattattcta tgaattgggt gcgccaagcc     120
cctgggaagg gtctcgagtg ggtgagctat atctatggtg gtggtagcta tacctattat     180
gcggatagcg tgaaaggccg ttttaccatt tcacgtgata attcgaaaaa cacccctgtat     240
ctgcaaatga acagcctgcg tgcggaagat acggccgtgt attattgcgc gcgtcaggct     300
ggtatgtatt ttgatgtttg gggccaaggc accctggtga cggttagctc a              351
```

<210> SEQ ID NO 14
<211> LENGTH: 372
<212> TYPE: DNA
<213> ORGANISM: Homo sapiens

<400> SEQUENCE: 14

```
caggtgcaat tgcaagaaag tggtccgggc ctggtgaaac cgggcgaaac cctgagcctg      60
acctgcaccg tttccggagg cagcattggt tattattgga attggattcg ccaggccct     120
gggaagggtc tcgagtggat tggccatatc tctcgttttg gctctaccaa ttataatccg     180
agcctgaaag gccgggtgac cattagcgtt gatacttcga aaaaccagtt tagcctgaaa     240
```

```
ctgagcagcg tgacggcgga agatacggcc gtgtattatt gcgcgcggga gtatactggt    300
aatgattggt atcgtcagca gggtcagcat gctgattatt ggggccaagg caccctggtg    360
acggttagct ca                                                        372
```

```
<210> SEQ ID NO 15
<211> LENGTH: 354
<212> TYPE: DNA
<213> ORGANISM: Homo sapiens

<400> SEQUENCE: 15
```

```
caggtgcaat tgaaagaaag cggcccggcc ctggtgaaac cgacccaaac cctgaccctg     60
acctgtacct tttccggatt tagcctgtct aattctggtg ttggtgtggg ttggattcgc    120
cagccgcctg gaaagccct cgagtggctg gctgatatct attctgatac tactaagcgt    180
tatagcacca gcctgaaaac gcgtctgacc attagcaaag atacttcgaa aaatcaggtg    240
gtgctgacta tgaccaacat ggacccggtg gatacggcca cctattattg cgcgcgttat    300
ggtgaggctt attttgatta ttggggccaa ggcaccctgg tgacggttag ctca          354
```

```
<210> SEQ ID NO 16
<211> LENGTH: 121
<212> TYPE: PRT
<213> ORGANISM: Homo sapiens

<400> SEQUENCE: 16
```

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Asn
            20                  25                  30

Ala Ile Ser Trp Val Arg Gln Ala Pro Gly Gln Gly Leu Glu Trp Met
        35                  40                  45

Gly Asn Ile Trp Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Gly Tyr Leu Asp Thr Asn Thr Tyr Ile Asp Tyr Trp Gly
            100                 105                 110

Gln Gly Thr Leu Val Thr Val Ser Ser
        115                 120
```

```
<210> SEQ ID NO 17
<211> LENGTH: 120
<212> TYPE: PRT
<213> ORGANISM: Homo sapiens

<400> SEQUENCE: 17
```

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Ala Ile Arg Tyr Asp Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
```

65                  70                  75                  80
Leu Gln Met Asn Ser Leu Arg Ala Glu Asp Thr Ala Val Tyr Tyr Cys
                85                  90                  95
Ala Arg Tyr Tyr Ser Gly Ile Tyr Gln His Ile Asp Tyr Trp Gly Gln
            100                 105                 110
Gly Thr Leu Val Thr Val Ser Ser
            115                 120

<210> SEQ ID NO 18
<211> LENGTH: 123
<212> TYPE: PRT
<213> ORGANISM: Homo sapiens

<400> SEQUENCE: 18

Gln Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Leu His Trp Val Arg Gln Ala Pro Gly Lys Gly Leu Glu Trp Val
        35                  40                  45
Ser Ser Ile Ser Gly Leu Gly Ser Thr Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Tyr His Tyr Glu Tyr His Tyr Phe Ser Ser Gly Phe Asp Asn
            100                 105                 110
Trp Gly Gln Gly Thr Leu Val Thr Val Ser Ser
            115                 120

<210> SEQ ID NO 19
<211> LENGTH: 117
<212> TYPE: PRT
<213> ORGANISM: Homo sapiens

<400> SEQUENCE: 19

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Gly Tyr
            20                  25                  30
Tyr Ile Asn Trp Val Arg Gln Ala Pro Gly Gln Gly Leu Glu Trp Met
        35                  40                  45
Gly Trp Ile Phe Pro Asn Gly Gly Ser Thr Gly Tyr Ala Gln Lys Phe
    50                  55                  60
Gln Gly Arg Val Thr Met Thr Arg Asp Thr Ser Ile Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Gly Asn Ile Phe Ile Phe Asp Tyr Trp Gly Gln Gly Thr Leu
            100                 105                 110
Val Thr Val Ser Ser
            115

<210> SEQ ID NO 20
<211> LENGTH: 120
<212> TYPE: PRT

<213> ORGANISM: Homo sapiens

<400> SEQUENCE: 20

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Tyr Met His Trp Val Arg Gln Ala Pro Gly Lys Gly Leu Glu Trp Val
        35                  40                  45

Ser Tyr Ile Asp Ser Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Leu Met Pro Phe Gly Gly Tyr Phe Asp Val Trp Gly Gln
            100                 105                 110

Gly Thr Leu Val Thr Val Ser Ser
        115                 120

<210> SEQ ID NO 21
<211> LENGTH: 120
<212> TYPE: PRT
<213> ORGANISM: Homo sapiens

<400> SEQUENCE: 21

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Asn Trp Val Arg Gln Ala Pro Gly Lys Gly Leu Glu Trp Val
        35                  40                  45

Ser Gly Ile Ser Gly Asp Pro Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Pro Leu Val Tyr Thr Gly Phe Ala Tyr Trp Gly Gln
            100                 105                 110

Gly Thr Leu Val Thr Val Ser Ser
        115                 120

<210> SEQ ID NO 22
<211> LENGTH: 121
<212> TYPE: PRT
<213> ORGANISM: Homo sapiens

<400> SEQUENCE: 22

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Gly Ile Ser Ser Trp Gly Ser Thr Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Asp Gly Ser Tyr Met Thr Asp Tyr Phe Ala Tyr Trp Gly
            100                 105                 110

Gln Gly Thr Leu Val Thr Val Ser Ser
        115                 120
```

<210> SEQ ID NO 23
<211> LENGTH: 124
<212> TYPE: PRT
<213> ORGANISM: Homo sapiens

<400> SEQUENCE: 23

```
Gln Val Gln Leu Lys Glu Ser Gly Pro Ala Leu Val Lys Pro Thr Gln
 1               5                  10                  15

Thr Leu Thr Leu Thr Cys Thr Phe Ser Gly Phe Ser Leu Ser Ser Asp
                 20                  25                  30

Gly Met Gly Val Gly Trp Ile Arg Gln Pro Pro Gly Lys Ala Leu Glu
            35                  40                  45

Trp Leu Ala Leu Ile Asp Trp Asp Asp Lys Arg Tyr Ser Thr Ser Ser
 50                  55                  60

Leu Lys Thr Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Phe Asn Trp Phe Tyr Arg Leu Ala Phe Val Asn Pro Asp
            100                 105                 110

Val Trp Gly Gln Gly Thr Leu Val Thr Val Ser Ser
            115                 120
```

<210> SEQ ID NO 24
<211> LENGTH: 122
<212> TYPE: PRT
<213> ORGANISM: Homo sapiens

<400> SEQUENCE: 24

```
Gln Val Gln Leu Lys Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ser
                 20                  25                  30

Arg Val Gly Val Ser Trp Ile Arg Gln Pro Pro Gly Lys Ala Leu Glu
            35                  40                  45

Trp Leu Ala His Ile Asp Trp Asn Asp Lys Tyr Tyr Ser Thr Ser Ser
 50                  55                  60

Leu Lys Thr Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Glu Asp Arg Leu Leu Gly Gly Tyr Gly Tyr Asp Val Trp
            100                 105                 110

Gly Gln Gly Thr Leu Val Thr Val Ser Ser
        115                 120
```

<210> SEQ ID NO 25

<211> LENGTH: 120
<212> TYPE: PRT
<213> ORGANISM: Homo sapiens

<400> SEQUENCE: 25

Gln Val Gln Leu Gln Glu Ser Gly Pro Gly Leu Val Lys Pro Gly Glu
1               5                   10                  15
Thr Leu Ser Leu Thr Cys Thr Val Ser Gly Gly Ser Ile Ser Gly Asn
            20                  25                  30
Tyr Trp Ser Trp Ile Arg Gln Ala Pro Gly Lys Gly Leu Glu Trp Ile
        35                  40                  45
Gly Asp Tyr His Gly Ser Thr Tyr Tyr Asn Pro Ser Leu Lys Gly Arg
    50                  55                  60
Val Thr Ile Ser Val Asp Thr Ser Lys Asn Gln Phe Ser Leu Lys Leu
65                  70                  75                  80
Ser Ser Val Thr Ala Glu Asp Thr Ala Val Tyr Tyr Cys Ala Arg Glu
                85                  90                  95
Gln Tyr His Trp Gly Leu Ala Trp Thr Gly Phe Asp Asn Trp Gly Gln
            100                 105                 110
Gly Thr Leu Val Thr Val Ser Ser
        115                 120

<210> SEQ ID NO 26
<211> LENGTH: 118
<212> TYPE: PRT
<213> ORGANISM: Homo sapiens

<400> SEQUENCE: 26

Gln Val Gln Leu Val Gln Ser Gly Ala Glu Val Lys Lys Pro Gly Glu
1               5                   10                  15
Ser Leu Lys Ile Ser Cys Lys Gly Ser Gly Tyr Ser Phe Ser Thr Ser
            20                  25                  30
Trp Val Gly Trp Val Arg Gln Met Pro Gly Lys Gly Leu Glu Trp Met
        35                  40                  45
Gly Ile Ile Asp Pro Asp Ile Ser Tyr Thr Tyr Ser Pro Ser Phe
    50                  55                  60
Gln Gly Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Ala Arg Tyr Leu Met Gly Leu Gly Tyr Asp Val Trp Gly Gln Gly Thr
            100                 105                 110
Leu Val Thr Val Ser Ser
        115

<210> SEQ ID NO 27
<211> LENGTH: 121
<212> TYPE: PRT
<213> ORGANISM: Homo sapiens

<400> SEQUENCE: 27

Gln Val Gln Leu Lys Glu Ser Gly Pro Ala Leu Val Lys Pro Thr Gln
1               5                   10                  15
Thr Leu Thr Leu Thr Cys Thr Phe Ser Gly Phe Ser Leu Ser Ser Ser
            20                  25                  30
Gly Met Ser Val Ser Trp Ile Arg Gln Pro Pro Gly Lys Ala Leu Glu
        35                  40                  45

```
Trp Leu Ala Arg Ile Tyr Ser Asp Asp Ser Lys Ser Tyr Ser Thr Ser
    50                  55                  60
Leu Lys Thr Arg Leu Thr Ile Ser Lys Asp Thr Ser Lys Asn Gln Val
65                  70                  75                  80
Val Leu Thr Met Thr Asn Met Asp Pro Val Asp Thr Ala Thr Tyr Tyr
                85                  90                  95
Cys Ala Arg Ala Ala His Trp Asn Gly Pro Leu Phe Asp Val Trp Gly
                100                 105                 110
Gln Gly Thr Leu Val Thr Val Ser Ser
            115                 120
```

<210> SEQ ID NO 28
<211> LENGTH: 117
<212> TYPE: PRT
<213> ORGANISM: Homo sapiens

<400> SEQUENCE: 28

```
Gln Val Gln Leu Val Glu Ser Gly Gly Leu Val Gln Pro Gly Gly
1               5                   10                  15
Ser Leu Arg Leu Ser Cys Ala Ala Ser Gly Phe Thr Phe Ser Asn Tyr
                20                  25                  30
Ser Met Asn Trp Val Arg Gln Ala Pro Gly Lys Gly Leu Glu Trp Val
                35                  40                  45
Ser Tyr Ile Tyr Gly Gly Gly Ser Tyr Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Gln Ala Gly Met Tyr Phe Asp Val Trp Gly Gln Gly Thr Leu
                100                 105                 110
Val Thr Val Ser Ser
            115
```

<210> SEQ ID NO 29
<211> LENGTH: 124
<212> TYPE: PRT
<213> ORGANISM: Homo sapiens

<400> SEQUENCE: 29

```
Gln Val Gln Leu Gln Glu Ser Gly Pro Gly Leu Val Lys Pro Gly Glu
1               5                   10                  15
Thr Leu Ser Leu Thr Cys Thr Val Ser Gly Gly Ser Ile Gly Tyr Tyr
                20                  25                  30
Trp Asn Trp Ile Arg Gln Ala Pro Gly Lys Gly Leu Glu Trp Ile Gly
                35                  40                  45
His Ile Ser Arg Phe Gly Ser Thr Asn Tyr Asn Pro Ser Leu Lys Gly
    50                  55                  60
Arg Val Thr Ile Ser Val Asp Thr Ser Lys Asn Gln Phe Ser Leu Lys
65                  70                  75                  80
Leu Ser Ser Val Thr Ala Glu Asp Thr Ala Val Tyr Tyr Cys Ala Arg
                85                  90                  95
Glu Tyr Thr Gly Asn Asp Trp Tyr Arg Gln Gly Gln His Ala Asp
                100                 105                 110
Tyr Trp Gly Gln Gly Thr Leu Val Thr Val Ser Ser
            115                 120
```

<210> SEQ ID NO 30
<211> LENGTH: 118
<212> TYPE: PRT
<213> ORGANISM: Homo sapiens

<400> SEQUENCE: 30

Gln Val Gln Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Asn Ser
            20                  25                  30

Gly Val Gly Val Gly Trp Ile Arg Gln Pro Pro Gly Lys Ala Leu Glu
        35                  40                  45

Trp Leu Ala Asp Ile Tyr Ser Asp Thr Thr Lys Arg Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Tyr Gly Glu Ala Tyr Phe Asp Tyr Trp Gly Gln Gly Thr
            100                 105                 110

Leu Val Thr Val Ser Ser
        115

<210> SEQ ID NO 31
<211> LENGTH: 333
<212> TYPE: DNA
<213> ORGANISM: Homo sapiens

<400> SEQUENCE: 31
gatatcgcac tgacccagcc agcttcagtg agcggctcac caggtcagag cattaccatc        60
tcgtgtacgg gtactagcag cgatattggt gcttatgtgt cttggtacca gcagcatccc       120
gggaaggcgc cgaaacttat gatttatgag gtttcttctc gtccctcagg cgtgagcaac       180
cgttttagcg gatccaaaag cggcaacacc gcgagcctga ccattagcgg cctgcaagcg       240
gaagacgaag cggattatta ttgctcttct tatgatctta ctcctcctgg taaggtgttt       300
ggcggcggca cgaagttaac cgttcttggc cag                                   333

<210> SEQ ID NO 32
<211> LENGTH: 324
<212> TYPE: DNA
<213> ORGANISM: Homo sapiens

<400> SEQUENCE: 32
gatatcgaac tgacccagcc gccttcagtg agcgttgcac caggtcagac cgcgcgtatc        60
tcgtgtagcg gcgataatat tggtcattat tatgtttctt ggtaccagca gaaacccggg       120
caggcgccag ttcttgtgat ttatggtgat aataatcgtc cctcaggcat cccggaacgc       180
tttagcggat ccaacagcgg caacaccgcg accctgacca ttagcggcac tcaggcggaa       240
gacgaagcgg attattattg cgcttctgat gttggttctc ttgatgtgtt tggcggcggc       300
acgaagttaa ccgttcttgg ccag                                             324

<210> SEQ ID NO 33
<211> LENGTH: 330
<212> TYPE: DNA
<213> ORGANISM: Homo sapiens

<400> SEQUENCE: 33

```
gatatcgtgc tgacccagag cccggcgacc ctgagcctgt ctccgggcga acgtgcgacc    60
ctgagctgca gagcgagcca gactggttct acttcttatc tggcttggta ccagcagaaa   120
ccaggtcaag caccgcgtct attaatttat gatgcttcta agcgtgcaac tggggtcccg   180
gcgcgtttta gcggctctgg atccggcacg gattttaccc tgaccattag cagcctggaa   240
cctgaagact ttgcgactta ttattgccat cagtattata cgttcctca tacctttggc    300 cagggtacga aagttgaaat taaacgtacg                                     330
```

<210> SEQ ID NO 34
<211> LENGTH: 333
<212> TYPE: DNA
<213> ORGANISM: Homo sapiens

<400> SEQUENCE: 34

```
gatatcgtgc tgacccagcc gccttcagtg agtggcgcac caggtcagcg tgtgaccatc    60
tcgtgtagcg gcagcagcag caacattggt aataattatg tgtcttggta ccagcagttg   120
cccgggacgg cgccgaaact tctgatttat ggtgatgatc agcgtccctc aggcgtgccg   180
gatcgtttta gcggatccaa aagcggcacc agcgcgagcc ttgcgattac gggcctgcaa   240
agcgaagacg aagcggatta ttattgccag tcttatggta ctttttcttc ttttgtgttt   300
ggcggcggca cgaagttaac cgttcttggc cag                                 333
```

<210> SEQ ID NO 35
<211> LENGTH: 327
<212> TYPE: DNA
<213> ORGANISM: Homo sapiens

<400> SEQUENCE: 35

```
gatatccaga tgacccagag cccgtctagc ctgagcgcga gcgtgggtga tcgtgtgacc    60
attacctgca gcgcgagcca gaatatttct cagtggctga attggtacca gcagaaacca   120
ggtaaagcac cgaaactatt aatttatggt gcttctaatt tgcaaagcgg ggtcccgtcc   180
cgttttagcg gctctggatc cggcactgat tttaccctga ccattagcag cctgcaacct   240
gaagactttg cgacttatta ttgccagcag tattatgatc ttcctaatac ctttggccag   300
ggtacgaaag ttgaaattaa acgtacg                                        327
```

<210> SEQ ID NO 36
<211> LENGTH: 327
<212> TYPE: DNA
<213> ORGANISM: Homo sapiens

<400> SEQUENCE: 36

```
gatatcgaac tgacccagcc gccttcagtg agcgttgcac caggtcagac cgcgcgtatc    60
tcgtgtagcg gcgataatct tcgtcattat tatgtttatt ggtaccagca gaaacccggg   120
caggcgccag ttcttgtgat ttatggtgat tctaagcgtc cctcaggcat cccggaacgc   180
tttagcggat ccaacagcgg caacaccgcg accctgacca ttagcggcac tcaggcggaa   240
gacgaagcgg attattattg ccagacttat actggtggtg cttctcttgt gtttggcggc   300
ggcacgaagt taaccgttct tggccag                                        327
```

<210> SEQ ID NO 37
<211> LENGTH: 321
<212> TYPE: DNA
<213> ORGANISM: Homo sapiens

```
<400> SEQUENCE: 37
gatatcgaac tgacccagcc gccttcagtg agcgttgcac caggtcagac cgcgcgtatc    60
tcgtgtagcg gcgataatat tggtcattat tatgtttctt ggtaccagca gaaacccggg   120
caggcgccag ttcttgtgat ttattctgat tctaatcgtc cctcaggcat cccggaacgc   180
tttagcggat ccaacagcgg caacaccgcg accctgacca ttagcggcac tcaggcggaa   240
gacgaagcgg attattattg ccagtcttat aatggtactt atgtgtttgg cggcggcacg   300
aagttaaccg ttcttggcca g                                              321

<210> SEQ ID NO 38
<211> LENGTH: 330
<212> TYPE: DNA
<213> ORGANISM: Homo sapiens

<400> SEQUENCE: 38
gatatcgtgc tgacccagag cccggcgacc ctgagcctgt ctccgggcga acgtgcgacc    60
ctgagctgca gagcgagcca gtctgtttct tcttcttatc tggcttggta ccagcagaaa   120
ccaggtcaag caccgcgtct attaatttat ggtgcttctt ctcgtgcaac tggggtcccg   180
gcgcgtttta gcggctctgg atccggcacg gattttaccc tgaccattag cagcctggaa   240
cctgaagact ttgcggttta ttattgccag cagggttata attctccttt tacctttggc   300
cagggtacga agttgaaat taaacgtacg                                      330

<210> SEQ ID NO 39
<211> LENGTH: 330
<212> TYPE: DNA
<213> ORGANISM: Homo sapiens

<400> SEQUENCE: 39
gatatcgaac tgacccagcc gccttcagtg agcgttgcac caggtcagac cgcgcgtatc    60
tcgtgtagcg gcgattctct tggttcttat tatgttcatt ggtaccagca gaaacccggg   120
caggcgccag ttcttgtgat tggtgatgat actaagcgtc cctcaggcat cccggaacgc   180
tttagcggat ccaacagcgg caacaccgcg accctgacca ttagcggcac tcaggcggaa   240
gacgaagcgg attattattg cggttctcgt actggttata taattctttt tgtgtttggc   300
ggcggcacga agttaaccgt tcttggccag                                     330

<210> SEQ ID NO 40
<211> LENGTH: 324
<212> TYPE: DNA
<213> ORGANISM: Homo sapiens

<400> SEQUENCE: 40
gatatcgaac tgacccagcc gccttcagtg agcgttgcac caggtcagac cgcgcgtatc    60
tcgtgtagcg gcgataatct tggtcattat tatgtttctt ggtaccagca gaaacccggg   120
caggcgccag ttcttgtgat ttatgatgat tctgatcgtc cctcaggcat cccggaacgc   180
tttagcggat ccaacagcgg caacaccgcg accctgacca ttagcggcac tcaggcggaa   240
gacgaagcgg attattattg cggtgcttat gctatgcata tgactgtgtt tggcggcggc   300
acgaagttaa ccgttcttgg ccag                                           324

<210> SEQ ID NO 41
<211> LENGTH: 339
<212> TYPE: DNA
<213> ORGANISM: Homo sapiens
```

<400> SEQUENCE: 41

```
gatatcgcac tgacccagcc agcttcagtg agcggctcac caggtcagag cattaccatc    60
tcgtgtacgg gtactagcag cgatgttggt gctattaatt atgtgtcttg gtaccagcag   120
catcccggga aggcgccgaa acttatgatt tatgatgtta ataagcgtcc ctcaggcgtg   180
ccggatcgtt ttagcggatc caaaagcggc aacaccgcga gcctgaccat tagcggcctg   240
caagcggaag acgaagcgga ttattattgc ggttccttata ctatgcaggt tggttcttat   300
gtgtttggcg gcggcacgaa gttaaccgtt cttggccag                          339
```

<210> SEQ ID NO 42
<211> LENGTH: 327
<212> TYPE: DNA
<213> ORGANISM: Homo sapiens

<400> SEQUENCE: 42

```
gatatcgaac tgacccagcc gccttcagtg agcgttgcac caggtcagac cgcgcgtatc    60
tcgtgtagcg gcgataatat tggtcattat tatgctcatt ggtaccagca gaaacccggg   120
caggcgccag ttgttgtgat ttatgatgat aatgatcgtc cctcaggcat cccggaacgc   180
tttagcggat ccaacagcgg caacaccgcg accctgacca ttagcggcac tcaggcggaa   240
gacgaagcgg attattattg ccaggcttat actggtgatg gtggtcgtgt gtttggcggc   300
ggcacgaagt taaccgttct tggccag                                       327
```

<210> SEQ ID NO 43
<211> LENGTH: 330
<212> TYPE: DNA
<213> ORGANISM: Homo sapiens

<400> SEQUENCE: 43

```
gatatcgaac tgacccagcc gccttcagtg agcgttgcac caggtcagac cgcgcgtatc    60
tcgtgtagcg gcgataatct tggttctaag gttgtttctt ggtaccagca gaaacccggg   120
caggcgccag ttcttgtgat ttattatgat aataagcgtc cctcaggcat cccggaacgc   180
tttagcggat ccaacagcgg caacaccgcg accctgacca ttagcggcac tcaggcggaa   240
gacgaagcgg attattattg ccagtcttat acttttgagt ctggttctgt tgtgtttggc   300
ggcggcacga agttaaccgt tcttggccag                                    330
```

<210> SEQ ID NO 44
<211> LENGTH: 324
<212> TYPE: DNA
<213> ORGANISM: Homo sapiens

<400> SEQUENCE: 44

```
gatatcgaac tgacccagcc gccttcagtg agcgttgcac caggtcagac cgcgcgtatc    60
tcgtgtagcg gcgataatct tggtcattat tatgttgatt ggtaccagca gaaacccggg   120
caggcgccag ttcttgtgat ttatgctgat aataatcgtc cctcaggcat cccggaacgc   180
tttagcggat ccaacagcgg caacaccgcg accctgacca ttagcggcac tcaggcggaa   240
gacgaagcgg attattattg ctcttcttat tctcagcagt ctatggtgtt tggcggcggc   300
acgaagttaa ccgttcttgg ccag                                          324
```

<210> SEQ ID NO 45
<211> LENGTH: 330
<212> TYPE: DNA

<210> SEQ ID NO 46
<211> LENGTH: 111
<212> TYPE: PRT
<213> ORGANISM: Homo sapiens

<400> SEQUENCE: 45

```
gatatcgaac tgacccagcc gccttcagtg agcgttgcac caggtcagac cgcgcgtatc    60
tcgtgtagcg gcgataatct tggtaatttt tatgttcatt ggtaccagca gaaacccggg   120
caggcgccag ttcttgtgat ttatgaggat tctaatcgtc cctcaggcat cccggaacgc   180
tttagcggat ccaacagcgg caacaccgcg accctgacca ttagcggcac tcaggcggaa   240
gacgaagcgg attattattg ctcttcttgg gatatgtatc gtactatttt tgtgtttggc   300
ggcggcacga agttaaccgt tcttggccag                                    330
```

<210> SEQ ID NO 46
<211> LENGTH: 111
<212> TYPE: PRT
<213> ORGANISM: Homo sapiens

<400> SEQUENCE: 46

Asp Ile Ala Leu Thr Gln Pro Ala Ser Val Ser Gly Ser Pro Gly Gln
1               5                   10                  15
Ser Ile Thr Ile Ser Cys Thr Gly Thr Ser Ser Asp Ile Gly Ala Tyr
            20                  25                  30
Val Ser Trp Tyr Gln Gln His Pro Gly Lys Ala Pro Lys Leu Met Ile
        35                  40                  45
Tyr Glu Val Ser Ser Arg Pro Ser Gly Val Ser Asn Arg Phe Ser Gly
    50                  55                  60
Ser Lys Ser Gly Asn Thr Ala Ser Leu Thr Ile Ser Gly Leu Gln Ala
65                  70                  75                  80
Glu Asp Glu Ala Asp Tyr Tyr Cys Ser Ser Tyr Asp Leu Thr Pro Pro
                85                  90                  95
Gly Lys Val Phe Gly Gly Gly Thr Lys Leu Thr Val Leu Gly Gln
            100                 105                 110

<210> SEQ ID NO 47
<211> LENGTH: 108
<212> TYPE: PRT
<213> ORGANISM: Homo sapiens

<400> SEQUENCE: 47

Asp Ile Glu Leu Thr Gln Pro Pro Ser Val Ser Val Ala Pro Gly Gln
1               5                   10                  15
Thr Ala Arg Ile Ser Cys Ser Gly Asp Asn Ile Gly His Tyr Tyr Val
            20                  25                  30
Ser Trp Tyr Gln Gln Lys Pro Gly Gln Ala Pro Val Leu Val Ile Tyr
        35                  40                  45
Gly Asp Asn Asn Arg Pro Ser Gly Ile Pro Glu Arg Phe Ser Gly Ser
    50                  55                  60
Asn Ser Gly Asn Thr Ala Thr Leu Thr Ile Ser Gly Thr Gln Ala Glu
65                  70                  75                  80
Asp Glu Ala Asp Tyr Tyr Cys Ala Ser Asp Val Gly Ser Leu Asp Val
                85                  90                  95
Phe Gly Gly Gly Thr Lys Leu Thr Val Leu Gly Gln
            100                 105

<210> SEQ ID NO 48
<211> LENGTH: 110
<212> TYPE: PRT
<213> ORGANISM: Homo sapiens

<400> SEQUENCE: 48

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Thr Gly Ser Thr Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Lys Arg Ala Thr Gly Val Pro Ala Arg Phe Ser
50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys His Gln Tyr Tyr Asn Val Pro
            85                  90                  95

His Thr Phe Gly Gln Gly Thr Lys Val Glu Ile Lys Arg Thr
        100                 105                 110

<210> SEQ ID NO 49
<211> LENGTH: 111
<212> TYPE: PRT
<213> ORGANISM: Homo sapiens

<400> SEQUENCE: 49

Asp Ile Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Gly Asp Asp Gln Arg Pro Ser Gly Val Pro Asp Arg Phe Ser
50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Tyr Gly Thr Phe Ser
            85                  90                  95

Ser Phe Val Phe Gly Gly Gly Thr Lys Leu Thr Val Leu Gly Gln
        100                 105                 110

<210> SEQ ID NO 50
<211> LENGTH: 109
<212> TYPE: PRT
<213> ORGANISM: Homo sapiens

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Ser Gln Trp
            20                  25                  30

Leu Asn Trp Tyr Gln Gln Lys Pro Gly Lys Ala Pro Lys Leu Leu Ile
        35                  40                  45

Tyr Gly Ala Ser Asn Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asp Leu Pro Asn
            85                  90                  95

```
Thr Phe Gly Gln Gly Thr Lys Val Glu Ile Lys Arg Thr
            100                 105
```

<210> SEQ ID NO 51
<211> LENGTH: 109
<212> TYPE: PRT
<213> ORGANISM: Homo sapiens

<400> SEQUENCE: 51

```
Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Arg His Tyr Tyr Val
            20                  25                  30

Tyr Trp Tyr Gln Gln Lys Pro Gly Gln Ala Pro Val Leu Val Ile Tyr
        35                  40                  45

Gly Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Thr Gly Gly Ala Ser Leu
                85                  90                  95

Val Phe Gly Gly Gly Thr Lys Leu Thr Val Leu Gly Gln
            100                 105
```

<210> SEQ ID NO 52
<211> LENGTH: 107
<212> TYPE: PRT
<213> ORGANISM: Homo sapiens

<400> SEQUENCE: 52

```
Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly His Tyr Tyr Val
            20                  25                  30

Ser Trp Tyr Gln Gln Lys Pro Gly Gln Ala Pro Val Leu Val Ile Tyr
        35                  40                  45

Ser Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Asn Gly Thr Tyr Val Phe
                85                  90                  95

Gly Gly Gly Thr Lys Leu Thr Val Leu Gly Gln
            100                 105
```

<210> SEQ ID NO 53
<211> LENGTH: 110
<212> TYPE: PRT
<213> ORGANISM: Homo sapiens

<400> SEQUENCE: 53

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
```

-continued

```
                    50                  55                  60
Gly Ser Gly Ser Gly Thr Asp Phe Thr Leu Thr Ile Ser Ser Leu Glu
 65                  70                  75                  80

Pro Glu Asp Phe Ala Val Tyr Tyr Cys Gln Gln Gly Tyr Asn Ser Pro
                 85                  90                  95

Phe Thr Phe Gly Gln Gly Thr Lys Val Glu Ile Lys Arg Thr
                100                 105                 110
```

<210> SEQ ID NO 54
<211> LENGTH: 110
<212> TYPE: PRT
<213> ORGANISM: Homo sapiens

<400> SEQUENCE: 54

```
Asp Ile Glu Leu Thr Gln Pro Pro Ser Val Ser Val Ala Pro Gly Gln
 1               5                  10                  15

Thr Ala Arg Ile Ser Cys Ser Gly Asp Ser Leu Gly Ser Tyr Tyr Val
                20                  25                  30

His Trp Tyr Gln Gln Lys Pro Gly Gln Ala Pro Val Leu Val Ile Gly
             35                  40                  45

Asp Asp Thr Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gly Ser Arg Thr Gly Tyr Asn Asn Ser
                 85                  90                  95

Phe Val Phe Gly Gly Gly Thr Lys Leu Thr Val Leu Gly Gln
                100                 105                 110
```

<210> SEQ ID NO 55
<211> LENGTH: 108
<212> TYPE: PRT
<213> ORGANISM: Homo sapiens

<400> SEQUENCE: 55

```
Asp Ile Glu Leu Thr Gln Pro Pro Ser Val Ser Val Ala Pro Gly Gln
 1               5                  10                  15

Thr Ala Arg Ile Ser Cys Ser Gly Asp Asn Leu Gly His Tyr Tyr Val
                20                  25                  30

Ser Trp Tyr Gln Gln Lys Pro Gly Gln Ala Pro Val Leu Val Ile Tyr
             35                  40                  45

Asp Asp Ser Asp Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gly Ala Tyr Ala Met His Met Thr Val
                 85                  90                  95

Phe Gly Gly Gly Thr Lys Leu Thr Val Leu Gly Gln
                100                 105
```

<210> SEQ ID NO 56
<211> LENGTH: 113
<212> TYPE: PRT
<213> ORGANISM: Homo sapiens

<400> SEQUENCE: 56

```
Asp Ile Ala Leu Thr Gln Pro Ala Ser Val Ser Gly Ser Pro Gly Gln
 1               5                  10                  15
```

```
Ser Ile Thr Ile Ser Cys Thr Gly Thr Ser Ser Asp Val Gly Ala Ile
         20                  25                  30

Asn Tyr Val Ser Trp Tyr Gln Gln His Pro Gly Lys Ala Pro Lys Leu
         35                  40                  45

Met Ile Tyr Asp Val Asn Lys Arg Pro Ser Gly Val Pro Asp Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gly Ser Tyr Thr Met Gln
                 85                  90                  95

Val Gly Ser Tyr Val Phe Gly Gly Gly Thr Lys Leu Thr Val Leu Gly
                100                 105                 110

Gln

<210> SEQ ID NO 57
<211> LENGTH: 109
<212> TYPE: PRT
<213> ORGANISM: Homo sapiens

<400> SEQUENCE: 57

Asp Ile Glu Leu Thr Gln Pro Pro Ser Val Ser Val Ala Pro Gly Gln
 1               5                  10                  15

Thr Ala Arg Ile Ser Cys Ser Gly Asp Asn Ile Gly His Tyr Tyr Ala
         20                  25                  30

His Trp Tyr Gln Gln Lys Pro Gly Gln Ala Pro Val Val Val Ile Tyr
         35                  40                  45

Asp Asp Asn Asp Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Ala Tyr Thr Gly Asp Gly Gly Arg
                 85                  90                  95

Val Phe Gly Gly Gly Thr Lys Leu Thr Val Leu Gly Gln
                100                 105

<210> SEQ ID NO 58
<211> LENGTH: 110
<212> TYPE: PRT
<213> ORGANISM: Homo sapiens

<400> SEQUENCE: 58

Asp Ile Glu Leu Thr Gln Pro Pro Ser Val Ser Val Ala Pro Gly Gln
 1               5                  10                  15

Thr Ala Arg Ile Ser Cys Ser Gly Asp Asn Leu Gly Ser Lys Val Val
         20                  25                  30

Ser Trp Tyr Gln Gln Lys Pro Gly Gln Ala Pro Val Leu Val Ile Tyr
         35                  40                  45

Tyr Asp Asn Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Ser Tyr Thr Phe Glu Ser Gly Ser
                 85                  90                  95

Val Val Phe Gly Gly Gly Thr Lys Leu Thr Val Leu Gly Gln
                100                 105                 110
```

<210> SEQ ID NO 59
<211> LENGTH: 108
<212> TYPE: PRT
<213> ORGANISM: Homo sapiens

<400> SEQUENCE: 59

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Gly His Tyr Tyr Val
            20                  25                  30

Asp Trp Tyr Gln Gln Lys Pro Gly Gln Ala Pro Val Leu Val Ile Tyr
        35                  40                  45

Ala Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Ser Tyr Ser Gln Gln Ser Met Val
                85                  90                  95

Phe Gly Gly Gly Thr Lys Leu Thr Val Leu Gly Gln
            100                 105

<210> SEQ ID NO 60
<211> LENGTH: 110
<212> TYPE: PRT
<213> ORGANISM: Homo sapiens

<400> SEQUENCE: 60

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Gly Asn Phe Tyr Val
            20                  25                  30

His Trp Tyr Gln Gln Lys Pro Gly Gln Ala Pro Val Leu Val Ile Tyr
        35                  40                  45

Glu Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Ser Trp Asp Met Tyr Arg Thr Ile
                85                  90                  95

Phe Val Phe Gly Gly Gly Thr Lys Leu Thr Val Leu Gly Gln
            100                 105                 110

<210> SEQ ID NO 61
<211> LENGTH: 120
<212> TYPE: PRT
<213> ORGANISM: Homo sapiens

<400> SEQUENCE: 61

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr

```
                65                  70                  75                  80
Met Glu Leu Ser Ser Leu Arg Ser Glu Asp Thr Ala Val Tyr Tyr Cys
                        85                  90                  95

Ala Arg Trp Gly Gly Asp Gly Phe Tyr Ala Met Asp Tyr Trp Gly Gln
                100                 105                 110

Gly Thr Leu Val Thr Val Ser Ser
            115                 120

<210> SEQ ID NO 62
<211> LENGTH: 121
<212> TYPE: PRT
<213> ORGANISM: Homo sapiens

<400> SEQUENCE: 62

Gln Val Gln Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Val Gly Val Gly Trp Ile Arg Gln Pro Pro Gly Lys Ala Leu Glu
            35                  40                  45

Trp Leu Ala Leu Ile Asp Trp Asp Asp Lys Tyr Tyr Ser Thr Ser
50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Trp Gly Gly Asp Gly Phe Tyr Ala Met Asp Tyr Trp Gly
                100                 105                 110

Gln Gly Thr Leu Val Thr Val Ser Ser
            115                 120

<210> SEQ ID NO 63
<211> LENGTH: 120
<212> TYPE: PRT
<213> ORGANISM: Homo sapiens

<400> SEQUENCE: 63

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Gly Asp Gly Phe Tyr Ala Met Asp Tyr Trp Gly Gln
                100                 105                 110

Gly Thr Leu Val Thr Val Ser Ser
            115                 120

<210> SEQ ID NO 64
<211> LENGTH: 119
<212> TYPE: PRT
```

<213> ORGANISM: Homo sapiens

<400> SEQUENCE: 64

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Trp Gly Gly Asp Gly Phe Tyr Ala Met Asp Tyr Trp Gly Gln Gly
            100                 105                 110

Thr Leu Val Thr Val Ser Ser
        115

<210> SEQ ID NO 65
<211> LENGTH: 120
<212> TYPE: PRT
<213> ORGANISM: Homo sapiens

<400> SEQUENCE: 65

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 66
<211> LENGTH: 110
<212> TYPE: PRT
<213> ORGANISM: Homo sapiens

<400> SEQUENCE: 66

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile Tyr Asp Asn Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Gln His Tyr Thr Thr Pro
                85                  90                  95

Pro Val Phe Gly Gly Gly Thr Lys Leu Thr Val Leu Gly Gln
            100                 105                 110

<210> SEQ ID NO 67
<211> LENGTH: 111
<212> TYPE: PRT
<213> ORGANISM: Homo sapiens

<400> SEQUENCE: 67

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Gln His Tyr Thr Thr
                85                  90                  95

Pro Pro Val Phe Gly Gly Gly Thr Lys Leu Thr Val Leu Gly Gln
            100                 105                 110

<210> SEQ ID NO 68
<211> LENGTH: 107
<212> TYPE: PRT
<213> ORGANISM: Homo sapiens

<400> SEQUENCE: 68

Asp Ile Glu Leu Thr Gln Pro Pro Ser Val Ser Val Ala Pro Gly Gln
1               5                   10                  15

Thr Ala Arg Ile Ser Cys Ser Gly Asp Ala Leu Gly Asp Lys Tyr Ala
                20                  25                  30

Ser Trp Tyr Gln Gln Lys Pro Gly Gln Ala Pro Val Leu Val Ile Tyr
            35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Gln His Tyr Thr Thr Pro Pro Val
                85                  90                  95

Phe Gly Gly Gly Thr Lys Leu Thr Val Leu Gly
            100                 105

<210> SEQ ID NO 69
<211> LENGTH: 108
<212> TYPE: PRT
<213> ORGANISM: Homo sapiens

<400> SEQUENCE: 69

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Gly Ile Ser Ser Tyr
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg
            100                 105
```

<210> SEQ ID NO 70
<211> LENGTH: 110
<212> TYPE: PRT
<213> ORGANISM: Homo sapiens

<400> SEQUENCE: 70

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Val Pro Ala Arg Phe Ser
        50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln His Tyr Thr Thr Pro
                85                  90                  95

Pro Thr Phe Gly Gln Gly Thr Lys Val Glu Ile Lys Arg Thr
            100                 105                 110
```

<210> SEQ ID NO 71
<211> LENGTH: 300
<212> TYPE: PRT
<213> ORGANISM: Homo sapiens

<400> SEQUENCE: 71

```
Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
                20                  25                  30

Leu Ile Leu Val Val Val Leu Ala Val Val Val Pro Arg Trp Arg Gln
            35                  40                  45

Gln Trp Ser Gly Pro Gly Thr Thr Lys Arg Phe Pro Glu Thr Val Leu
        50                  55                  60

Ala Arg Cys Val Lys Tyr Thr Glu Ile His Pro Glu Met Arg His Val
65                  70                  75                  80

Asp Cys Gln Ser Val Trp Asp Ala Phe Lys Gly Ala Phe Ile Ser Lys
                85                  90                  95

His Pro Cys Asn Ile Thr Glu Glu Asp Tyr Gln Pro Leu Met Lys Leu
            100                 105                 110

Gly Thr Gln Thr Val Pro Cys Asn Lys Ile Leu Leu Trp Ser Arg Ile
        115                 120                 125
```

```
Lys Asp Leu Ala His Gln Phe Thr Gln Val Gln Arg Asp Met Phe Thr
    130                 135                 140
Leu Glu Asp Thr Leu Leu Gly Tyr Leu Ala Asp Asp Leu Thr Trp Cys
145                 150                 155                 160
Gly Glu Phe Asn Thr Ser Lys Ile Asn Tyr Gln Ser Cys Pro Asp Trp
                165                 170                 175
Arg Lys Asp Cys Ser Asn Asn Pro Val Ser Val Phe Trp Lys Thr Val
            180                 185                 190
Ser Arg Arg Phe Ala Glu Ala Ala Cys Asp Val Val His Val Met Leu
        195                 200                 205
Asn Gly Ser Arg Ser Lys Ile Phe Asp Lys Asn Ser Thr Phe Gly Ser
210                 215                 220
Val Glu Val His Asn Leu Gln Pro Glu Lys Val Gln Thr Leu Glu Ala
225                 230                 235                 240
Trp Val Ile His Gly Gly Arg Glu Asp Ser Arg Asp Leu Cys Gln Asp
                245                 250                 255
Pro Thr Ile Lys Glu Leu Glu Ser Ile Ile Ser Lys Arg Asn Ile Gln
            260                 265                 270
Phe Ser Cys Lys Asn Ile Tyr Arg Pro Asp Lys Phe Leu Gln Cys Val
        275                 280                 285
Lys Asn Pro Glu Asp Ser Ser Cys Thr Ser Glu Ile
290                 295                 300
```

<210> SEQ ID NO 72
<211> LENGTH: 1317
<212> TYPE: DNA
<213> ORGANISM: Homo sapiens

<400> SEQUENCE: 72

```
caggtggaat tggtggaatc tggaggatcc ctgaaactct cctgtgcagc ctcaggattc      60
gattttagta gatcctggat gaattgggtc cggcaggctc caggaaaagg ctagaatgg     120
attggagaaa ttaatccaga tagcagtacg ataaactata cgacatctct aaaggataaa    180
ttcatcatct ccagagacaa cgccaaaaat acgctgtacc tgcaaatgac caaagtgaga    240
tctgaggaca cagcccttta ttactgtgca agatatggta actggtttcc ttattgggc     300
caagggactc tggtcactgt cagctcagcc tccaccaagg gtccatcggt cttccccctg    360
gcaccctcct ccaagagcac ctctgggggc acagcggccc tgggctgcct ggtcaaggac    420
tacttccccg aaccggtgac ggtgtcgtgg aactcaggcg ccctgaccag cggcgtgcac    480
accttcccgg ctgtcctaca gtcctcagga ctctactccc tcagcagcgt ggtgaccgtg    540
ccctccagca gcttgggcac ccagacctac atctgcaacg tgaatcacaa gcccagcaac    600
accaaggtgg acaagaaagt tgagcccaaa tcttgtgaca aaactcacac atgcccaccg    660
tgcccagcac ctgaactcct ggggggaccg tcagtcttcc tcttcccccc aaaacccaag    720
gacaccctca tgatctcccg gacccctgag gtcacatgcg tggtggtgga cgtgagccac    780
gaagaccctg aggtcaagtt caactggtac gtggacggcg tggaggtgca taatgccaag    840
acaaagccgc gggaggagca gtacaacagc acgtaccggg tggtcagcgt cctcaccgtc    900
ctgcaccagg actggctgaa tggcaaggag tacaagtgca aggtctccaa caaagccctc    960
ccagccccca tcgagaaaac catctccaaa gccaaaggc agccccgaga accacaggtg    1020
tacaccctgc cccatcccg ggatgagctg accaagaacc aggtcagcct gacctgcctg    1080
gtcaaaggct tctatcccag cgacatcgcc gtggagtggg agagcaatgg gcagccggag    1140
```

```
aacaactaca agaccacgcc tcccgtgctg gactccgacg gctccttctt cctctacagc   1200
aagctcaccg tggacaagag caggtggcag caggggaacg tcttctcatg ctccgtgatg   1260
catgaggctc tgcacaacca ctacacgcag aagagcctct ccctgtctcc gggtaaa      1317
```

<210> SEQ ID NO 73
<211> LENGTH: 642
<212> TYPE: DNA
<213> ORGANISM: Homo sapiens

<400> SEQUENCE: 73

```
gatatcctga tgacccagtc tcaaaaaatc atgcccacat cagtgggaga cagggtcagc    60
gtcacctgca aggccagtca aaatgtggat actaatgtag cctggtatca acagaaacca   120
ggacagtctc ctaaagcact gatttactcg gcatcctacc gatacagtgg agtccctgat   180
cgcttcacag gcagtggatc tgggacagat ttcactctca ccatcaccaa tgtgcagtct   240
gaggacttgg cagagtattt ctgtcagcaa tatgacagct atcctctcac gttcggtgct   300
gggaccaagc tggacctgaa acgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga aaacacaaa gtctacgcct gcgaagtcac ccatcagggc   600
ctgagctcgc ccgtcacaaa gagcttcaac aggggagagt gt                       642
```

<210> SEQ ID NO 74
<211> LENGTH: 1500
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 74

```
tcgctattac catggtgatg cggttttggc agtacatcaa tgggcgtgga tagcggtttg    60
actcacgggg atttccaagt ctccacccca ttgacgtcaa tgggagtttg ttttggcacc   120
aaaatcaacg ggactttcca aaatgtcgta caactccgcc ccattgacgc aaatgggcg   180 gtaggcgtgt acggtgggag gtctatataa gcagagctct ctggctaact agagaaccca   240
ctgcttactg gcttatcgaa attaatacga ctcactatag ggagacccaa gctggctagc   300
gccaccatga aacacctgtg gttcttcctc ctgctggtgg cagctcccag atgggtcctg   360
tcccaggtgg aattctgcag gcggttagct cagcctccac caagggtcca tcggtcttcc   420
ccctggcacc ctcctccaag agcacctctg ggggcacagc ggccctgggc tgcctggtca   480
aggactactt ccccgaaccg gtgacggtgt cgtggaactc aggcgccctg accagcggcg   540
tgcacacctt cccggctgtc ctacagtcct caggactcta ctccctcagc agcgtggtga   600
ccgtgccctc cagcagcttg ggcacccaga cctacatctg caacgtgaat cacaagccca   660
gcaacaccaa ggtggacaag aaagttgagc ccaaatcttg tgacaaaact cacacatgcc   720
caccgtgccc agcacctgaa ctcctggggg gaccgtcagt cttcctcttc cccccaaaac   780
ccaaggacac cctcatgatc tcccggaccc ctgaggtcac atgcgtggtg gtggacgtga   840
gccacgaaga ccctgaggtc aagttcaact ggtacgtgga cggcgtggag gtgcataatg   900
ccaagacaaa gccgcgggag gagcagtaca acagcacgta ccgggtggtc agcgtcctca   960
```

```
ccgtcctgca ccaggactgg ctgaatggca aggagtacaa gtgcaaggtc tccaacaaag    1020
ccctcccagc ccccatcgag aaaccatct  ccaaagccaa agggcagccc cgagaaccac    1080
aggtgtacac cctgccccca tcccgggatg agctgaccaa gaaccaggtc agcctgacct    1140
gcctggtcaa aggcttctat cccagcgaca tcgccgtgga gtgggagagc aatgggcagc    1200
cggagaacaa ctacaagacc acgcctcccg tgctggactc cgacggctcc ttcttcctct    1260
acagcaagct caccgtggac aagagcaggt ggcagcaggg gaacgtcttc tcatgctccg    1320
tgatgcatga ggctctgcac aaccactaca cgcagaagag cctctccctg tctccgggta    1380
aatgagggcc cgtttaaacc cgctgatcag cctcgactgt gccttctagt tgccagccat    1440
ctgttgtttg cccctccccc gtgccttcct tgaccctgga aggtgccact cccactgtcc    1500

<210> SEQ ID NO 75
<211> LENGTH: 800
<212> TYPE: DNA
<213> ORGANISM: Homo sapiens
<220> FEATURE:
<221> NAME/KEY: CDS
<222> LOCATION: (307)..(705)

<400> SEQUENCE: 75
tcgctattac catggtgatg cggttttggc agtacatcaa tgggcgtgga tagcggtttg    60
actcacgggg atttccaagt ctccacccca ttgacgtcaa tgggagtttg ttttggcacc    120
aaaatcaacg ggactttcca aatgtcgta  acaactccgc cccattgacg caaatgggcg    180
gtaggcgtgt acggtgggag gtctatataa gcagagctct ctggctaact agagaaccca    240
ctgcttactg gcttatcgaa attaatacga ctcactatag ggagacccaa gctggctagc    300 gccacc atg gtg ttg cag acc cag gtc ttc att tct ctg ttg ctc tgg      348
       Met Val Leu Gln Thr Gln Val Phe Ile Ser Leu Leu Leu Trp
       1               5                   10 atc tct ggt gcc tac ggg gat atc gtg atg att aaa cgt acg gtg gct      396
Ile Ser Gly Ala Tyr Gly Asp Ile Val Met Ile Lys Arg Thr Val Ala
15                  20                  25                  30 gca cca tct gtc ttc atc ttc ccg cca tct gat gag cag ttg aaa tct      444
Ala Pro Ser Val Phe Ile Phe Pro Pro Ser Asp Glu Gln Leu Lys Ser
                35                  40                  45 gga act gcc tct gtt gtg tgc ctg ctg aat aac ttc tat ccc aga gag      492
Gly Thr Ala Ser Val Val Cys Leu Leu Asn Asn Phe Tyr Pro Arg Glu
            50                  55                  60 gcc aaa gta cag tgg aag gtg gat aac gcc ctc caa tcg ggt aac tcc      540
Ala Lys Val Gln Trp Lys Val Asp Asn Ala Leu Gln Ser Gly Asn Ser
        65                  70                  75 cag gag agt gtc aca gag cag gac agc aag gac agc acc tac agc ctc      588
Gln Glu Ser Val Thr Glu Gln Asp Ser Lys Asp Ser Thr Tyr Ser Leu
    80                  85                  90 agc agc acc ctg acg ctg agc aaa gca gac tac gag aaa cac aaa gtc      636
Ser Ser Thr Leu Thr Leu Ser Lys Ala Asp Tyr Glu Lys His Lys Val
95                  100                 105                 110 tac gcc tgc gaa gtc acc cat cag ggc ctg agc tcg ccc gtc aca aag      684
Tyr Ala Cys Glu Val Thr His Gln Gly Leu Ser Ser Pro Val Thr Lys
                115                 120                 125 agc ttc aac agg gga gag tgt tagggggccccg tttaaacccg ctgatcagcc       735
Ser Phe Asn Arg Gly Glu Cys
                130 tcgactgtgc cttctagttg ccagccatct gttgtttgcc cctccccgt gccttccttg    795 accct                                                                800
```

<210> SEQ ID NO 76
<211> LENGTH: 800
<212> TYPE: DNA
<213> ORGANISM: Homo sapiens
<220> FEATURE:
<221> NAME/KEY: CDS
<222> LOCATION: (307)..(384)
<220> FEATURE:
<221> NAME/KEY: CDS
<222> LOCATION: (386)..(712)

<400> SEQUENCE: 76

```
tcgctattac catggtgatg cggttttggc agtacatcaa tgggcgtgga tagcggtttg    60
actcacgggg atttccaagt ctccacccca ttgacgtcaa tgggagtttg ttttggcacc   120
aaaatcaacg ggactttcca aaatgtcgta acaactccgc cccattgacg caaatgggcg   180
gtaggcgtgt acggtgggag gtctatataa gcagagctct ctggctaact agagaaccca   240
ctgcttactg gcttatcgaa attaatacga ctcactatag ggagacccaa gctggctagc   300 gccacc atg gcc tgg gct ctg ctg ctc ctc acc ctc ctc act cag ggc      348
       Met Ala Trp Ala Leu Leu Leu Leu Thr Leu Leu Thr Gln Gly
       1               5                  10 aca gga tcc tgg gct gat atc gtg atg cac gaa gtt a acc gtc cta ggt  397
Thr Gly Ser Trp Ala Asp Ile Val Met His Glu Val   Thr Val Leu Gly
15                  20                  25                  30 cag ccc aag gct gcc ccc tcg gtc act ctg ttc ccg ccc tcc tct gag    445
Gln Pro Lys Ala Ala Pro Ser Val Thr Leu Phe Pro Pro Ser Ser Glu
                35                  40                  45 gag ctt caa gcc aac aag gcc aca ctg gtg tgt ctc ata agt gac ttc    493
Glu Leu Gln Ala Asn Lys Ala Thr Leu Val Cys Leu Ile Ser Asp Phe
            50                  55                  60 tac ccg gga gcc gtg aca gtg gcc tgg aag gga gat agc agc ccc gtc    541
Tyr Pro Gly Ala Val Thr Val Ala Trp Lys Gly Asp Ser Ser Pro Val
        65                  70                  75 aag gcg gga gtg gag acc acc aca ccc tcc aaa caa agc aac aac aag    589
Lys Ala Gly Val Glu Thr Thr Thr Pro Ser Lys Gln Ser Asn Asn Lys
    80                  85                  90 tac gcg gcc agc agc tat ctg agc ctg acg cct gag cag tgg aag tcc    637
Tyr Ala Ala Ser Ser Tyr Leu Ser Leu Thr Pro Glu Gln Trp Lys Ser
95                 100                 105                 110 cac aga agc tac agc tgc cag gtc acg cat gaa ggg agc acc gtg gag    685
His Arg Ser Tyr Ser Cys Gln Val Thr His Glu Gly Ser Thr Val Glu
                115                 120                 125 aag aca gtg gcc cct aca gaa tgt tca tagggcccg tttaaacccg            732
Lys Thr Val Ala Pro Thr Glu Cys Ser
                130                 135 ctgatcagcc tcgactgtgc cttctagttg ccagccatct gttgtttgcc cctcccccgt   792
gccttcct                                                            800
```

<210> SEQ ID NO 77
<211> LENGTH: 360
<212> TYPE: DNA
<213> ORGANISM: Homo sapiens

<400> SEQUENCE: 77

```
caggtgcaat tggtggaaag cggcggcggc ctggtgcaac cgggcggcag cctgcgtctg    60
agctgcgcgg cctccggatt tacctttttct tcttattata tgaattgggt gcgccaagcc   120
cctgggaagg gtctcgagtg ggtgagcggt attaatatgg agtctactcg tatttattat   180
gctgattctg ttaagggtcg ttttaccatt tcacgtgata attcgaaaaa caccctgtat   240
```

```
ctgcaaatga acagcctgcg tgcggaagat acggccgtgt attattgcgc gcgtgatctt     300
cctcttgttt atactggttt tgcttattgg ggccaaggca ccctggtgac ggttagctca     360
```

<210> SEQ ID NO 78
<211> LENGTH: 360
<212> TYPE: DNA
<213> ORGANISM: Homo sapiens

<400> SEQUENCE: 78

```
caggtgcaat tggtggaaag cggcggcggc ctggtgcaac cgggcggcag cctgcgtctg      60
agctgcgcgg cctccggatt tacctttcct tcttattata tgaattgggt gcgccaagcc     120
cctgggaagg gtctcgagtg ggtgagcgct atttctcatg atggtaatgt taagtattat     180
gctgattctg ttaagggtcg ttttaccatt tcacgtgata attcgaaaaa caccctgtat     240
ctgcaaatga acagcctgcg tgcggaagat acggccgtgt attattgcgc gcgtgatctt     300
cctcttgttt atactggttt tgcttattgg ggccaaggca ccctggtgac ggttagctca     360
```

<210> SEQ ID NO 79
<211> LENGTH: 360
<212> TYPE: DNA
<213> ORGANISM: Homo sapiens

<400> SEQUENCE: 79

```
caggtgcaat tggtggaaag cggcggcggc ctggtgcaac cgggcggcag cctgcgtctg      60
agctgcgcgg cctccggatt tacctttcct tcttattata tgaattgggt gcgccaagcc     120
cctgggaagg gtctcgagtg ggtgagcgct atttctatga atggtgatta tatttcttat     180
gctgattctg ttaagggtcg ttttaccatt tcacgtgata attcgaaaaa caccctgtat     240
ctgcaaatga acagcctgcg tgcggaagat acggccgtgt attattgcgc gcgtgatctt     300
cctcttgttt atactggttt tgcttattgg ggccaaggca ccctggtgac ggttagctca     360
```

<210> SEQ ID NO 80
<211> LENGTH: 360
<212> TYPE: DNA
<213> ORGANISM: Homo sapiens

<400> SEQUENCE: 80

```
caggtgcaat tggtggaaag cggcggcggc ctggtgcaac cgggcggcag cctgcgtctg      60
agctgcgcgg cctccggatt tacctttcct tcttattata tgaattgggt gcgccaagcc     120
cctgggaagg gtctcgagtg ggtgagcgct attaatcttt ctggttctgc taagtattat     180
gctgattctg ttaagggtcg ttttaccatt tcacgtgata attcgaaaaa caccctgtat     240
ctgcaaatga acagcctgcg tgcggaagat acggccgtgt attattgcgc gcgtgatctt     300
cctcttgttt atactggttt tgcttattgg ggccaaggca ccctggtgac ggttagctca     360
```

<210> SEQ ID NO 81
<211> LENGTH: 360
<212> TYPE: DNA
<213> ORGANISM: Homo sapiens

<400> SEQUENCE: 81

```
caggtgcaat tggtggaaag cggcggcggc ctggtgcaac cgggcggcag cctgcgtctg      60
agctgcgcgg cctccggatt tacctttcct tcttattata tgaattgggt gcgccaagcc     120
cctgggaagg gtctcgagtg ggtgagcgct atttcttcta atggtgatat tacttattat     180
```

```
gctgattctg ttaagggtcg ttttaccatt tcacgtgata attcgaaaaa caccctgtat    240
ctgcaaatga acagcctgcg tgcggaagat acggccgtgt attattgcgc gcgtgatctt    300
cctcttgttt atactggttt tgcttattgg ggccaaggca ccctggtgac ggttagctca    360
```

<210> SEQ ID NO 82
<211> LENGTH: 360
<212> TYPE: DNA
<213> ORGANISM: Homo sapiens

<400> SEQUENCE: 82

```
caggtgcaat tggtggaaag cggcggcggc ctggtgcaac cgggcggcag cctgcgtctg     60
agctgcgcgg cctccggatt tacctttttct tcttattata tgaattgggt gcgccaagcc    120
cctgggaagg gtctcgagtg ggtgagcgct atttctacta atggttggca gacttattat    180
gctgattctg ttaagggtcg ttttaccatt tcacgtgata attcgaaaaa caccctgtat    240
ctgcaaatga acagcctgcg tgcggaagat acggccgtgt attattgcgc gcgtgatctt    300
cctcttgttt atactggttt tgcttattgg ggccaaggca ccctggtgac ggttagctca    360
```

<210> SEQ ID NO 83
<211> LENGTH: 360
<212> TYPE: DNA
<213> ORGANISM: Homo sapiens

<400> SEQUENCE: 83

```
caggtgcaat tggtggaaag cggcggcggc ctggtgcaac cgggcggcag cctgcgtctg     60
agctgcgcgg cctccggatt tacctttttct tcttattata tgaattgggt gcgccaagcc    120
cctgggaagg gtctcgagtg ggtgagcgct attaatatga ttggtaatgt tactaattat    180
gctgattctg ttaagggtcg ttttaccatt tcacgtgata attcgaaaaa caccctgtat    240
ctgcaaatga acagcctgcg tgcggaagat acggccgtgt attattgcgc gcgtgatctt    300
cctcttgttt atactggttt tgcttattgg ggccaaggca ccctggtgac ggttagctca    360
```

<210> SEQ ID NO 84
<211> LENGTH: 360
<212> TYPE: DNA
<213> ORGANISM: Homo sapiens

<400> SEQUENCE: 84

```
caggtgcaat tggtggaaag cggcggcggc ctggtgcaac cgggcggcag cctgcgtctg     60
agctgcgcgg cctccggatt tacctttttct tcttattata tgaattgggt gcgccaagcc    120
cctgggaagg gtctcgagtg ggtgagctat attaatccta atggtatgat gactaattat    180
gctgattctg ttaagggtcg ttttaccatt tcacgtgata attcgaaaaa caccctgtat    240
ctgcaaatga acagcctgcg tgcggaagat acggccgtgt attattgcgc gcgtgatctt    300
cctcttgttt atactggttt tgcttattgg ggccaaggca ccctggtgac ggttagctca    360
```

<210> SEQ ID NO 85
<211> LENGTH: 360
<212> TYPE: DNA
<213> ORGANISM: Homo sapiens

<400> SEQUENCE: 85

```
caggtgcaat tggtggaaag cggcggcggc ctggtgcaac cgggcggcag cctgcgtctg     60
agctgcgcgg cctccggatt tacctttttct tcttattata tgaattgggt gcgccaagcc    120
cctgggaagg gtctcgagtg ggtgagcgtt atttctcctg gtggtgaggc taagtcttat    180
```

```
gctgattctg ttaagggtcg ttttaccatt tcacgtgata attcgaaaaa caccctgtat    240
ctgcaaatga acagcctgcg tgcggaagat acggccgtgt attattgcgc gcgtgatctt    300
cctcttgttt atactggttt tgcttattgg ggccaaggca ccctggtgac ggttagctca    360
```

<210> SEQ ID NO 86
<211> LENGTH: 360
<212> TYPE: DNA
<213> ORGANISM: Homo sapiens

<400> SEQUENCE: 86

```
caggtgcaat tggtggaaag cggcggcggc ctggtgcaac cgggcggcag cctgcgtctg     60
agctgcgcgg cctccggatt tacctttttct tcttattata tgaattgggt gcgccaagcc   120
cctgggaagg gtctcgagtg ggtgagcgct atttctggta atggtggtca tacttattat   180
gctgattctg ttaagggtcg ttttaccatt tcacgtgata attcgaaaaa caccctgtat    240
ctgcaaatga acagcctgcg tgcggaagat acggccgtgt attattgcgc gcgtgatctt    300
cctcttgttt atactggttt tgcttattgg ggccaaggca ccctggtgac ggttagctca    360
```

<210> SEQ ID NO 87
<211> LENGTH: 360
<212> TYPE: DNA
<213> ORGANISM: Homo sapiens

<400> SEQUENCE: 87

```
caggtgcaat tggtggaaag cggcggcggc ctggtgcaac cgggcggcag cctgcgtctg     60
agctgcgcgg cctccggatt tacctttttct tcttattata tgaattgggt gcgccaagcc   120
cctgggaagg gtctcgagtg ggtgagcgct atttctatgg atggtgttta taagtattat   180
gctgattctg ttaagggtcg ttttaccatt tcacgtgata attcgaaaaa caccctgtat    240
ctgcaaatga acagcctgcg tgcggaagat acggccgtgt attattgcgc gcgtgatctt    300
cctcttgttt atactggttt tgcttattgg ggccaaggca ccctggtgac ggttagctca    360
```

<210> SEQ ID NO 88
<211> LENGTH: 360
<212> TYPE: DNA
<213> ORGANISM: Homo sapiens

<400> SEQUENCE: 88

```
caggtgcaat tggtggaaag cggcggcggc ctggtgcaac cgggcggcag cctgcgtctg     60
agctgcgcgg cctccggatt tacctttttct tcttattata tgaattgggt gcgccaagcc   120
cctgggaagg gtctcgagtg ggtgagcgct atttctaata atggtaatgt tacttattat   180
gctgattctg ttaagggtcg ttttaccatt tcacgtgata attcgaaaaa caccctgtat    240
ctgcaaatga acagcctgcg tgcggaagat acggccgtgt attattgcgc gcgtgatctt    300
cctcttgttt atactggttt tgcttattgg ggccaaggca ccctggtgac ggttagctca    360
```

<210> SEQ ID NO 89
<211> LENGTH: 360
<212> TYPE: DNA
<213> ORGANISM: Homo sapiens

<400> SEQUENCE: 89

```
caggtgcaat tggtggaaag cggcggcggc ctggtgcaac cgggcggcag cctgcgtctg     60
agctgcgcgg cctccggatt tacctttttct tcttattata tgaattgggt gcgccaagcc   120
```

```
cctgggaagg gtctcgagtg ggtgagcgct atttctatgc atggtgatac tacttattat    180
gctgattctg ttaagggtcg ttttaccatt tcacgtgata attcgaaaaa caccctgtat    240
ctgcaaatga acagcctgcg tgcggaagat acggccgtgt attattgcgc gcgtgatctt    300
cctcttgttt atactggttt tgcttattgg ggccaaggca ccctggtgac ggttagctca    360
```

<210> SEQ ID NO 90
<211> LENGTH: 369
<212> TYPE: DNA
<213> ORGANISM: Homo sapiens

<400> SEQUENCE: 90

```
caggtgcaat tggtggaaag cggcggcggc ctggtgcaac cgggcggcag cctgcgtctg     60
agctgcgcgg cctccggatt taccttttct tcttatgcta tgaattgggt gcgccaagcc    120
cctgggaagg gtctcgagtg ggtgagccat attcgtaaga agaatacttc ttatactact    180
gagtatgctg cttctgttaa gggtcgtttt accatttcac gtgataattc gaaaaacacc    240
ctgtatctgc aaatgaacag cctgcgtgcg aagatacggg ccgtgtatta ttgcgcgcgt    300
gaggatggtt cttatatgac tgattatttt gcttattggg gccaaggcac cctggtgacg    360
gttagctca                                                             369
```

<210> SEQ ID NO 91
<211> LENGTH: 360
<212> TYPE: DNA
<213> ORGANISM: Homo sapiens

<400> SEQUENCE: 91

```
caggtgcaat tggtggaaag cggcggcggc ctggtgcaac cgggcggcag cctgcgtctg     60
agctgcgcgg cctccggatt taccttttct tcttatgcta tgaattgggt gcgccaagcc    120
cctgggaagg gtctcgagtg ggtgagcaat attcagcgtg ttggttctac ttattatgct    180
gattctgtta agggtcgttt taccatttca cgtgataatt cgaaaaacac cctgtatctg    240
caaatgaaca gcctgcgtgc ggaagatacg gccgtgtatt attgcgcgcg tgaggatggt    300
tcttatatga ctgattattt tgcttattgg ggccaaggca ccctggtgac ggttagctca    360
```

<210> SEQ ID NO 92
<211> LENGTH: 120
<212> TYPE: PRT
<213> ORGANISM: Homo sapiens

<400> SEQUENCE: 92

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Asn Trp Val Arg Gln Ala Pro Gly Lys Gly Leu Glu Trp Val
        35                  40                  45

Ser Gly Ile Asn Met Glu Ser Thr Arg Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Pro Leu Val Tyr Thr Gly Phe Ala Tyr Trp Gly Gln
            100                 105                 110
```

```
Gly Thr Leu Val Thr Val Ser Ser
        115                 120

<210> SEQ ID NO 93
<211> LENGTH: 120
<212> TYPE: PRT
<213> ORGANISM: Homo sapiens

<400> SEQUENCE: 93

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Asn Trp Val Arg Gln Ala Pro Gly Lys Gly Leu Glu Trp Val
        35                  40                  45

Ser Ala Ile Ser His Asp Gly Asn Val Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Pro Leu Val Tyr Thr Gly Phe Ala Tyr Trp Gly Gln
            100                 105                 110

Gly Thr Leu Val Thr Val Ser Ser
        115                 120

<210> SEQ ID NO 94
<211> LENGTH: 120
<212> TYPE: PRT
<213> ORGANISM: Homo sapiens

<400> SEQUENCE: 94

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Asn Trp Val Arg Gln Ala Pro Gly Lys Gly Leu Glu Trp Val
        35                  40                  45

Ser Ala Ile Ser Met Asn Gly Asp Tyr Ile Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Pro Leu Val Tyr Thr Gly Phe Ala Tyr Trp Gly Gln
            100                 105                 110

Gly Thr Leu Val Thr Val Ser Ser
        115                 120

<210> SEQ ID NO 95
<211> LENGTH: 120
<212> TYPE: PRT
<213> ORGANISM: Homo sapiens

<400> SEQUENCE: 95

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
```

```
                    20                  25                  30

Tyr Met Asn Trp Val Arg Gln Ala Pro Gly Lys Gly Leu Glu Trp Val
                35                  40                  45

Ser Ala Ile Asn Leu Ser Gly Ser Ala Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Pro Leu Val Tyr Thr Gly Phe Ala Tyr Trp Gly Gln
               100                 105                 110

Gly Thr Leu Val Thr Val Ser Ser
           115                 120

<210> SEQ ID NO 96
<211> LENGTH: 120
<212> TYPE: PRT
<213> ORGANISM: Homo sapiens

<400> SEQUENCE: 96

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Tyr Met Asn Trp Val Arg Gln Ala Pro Gly Lys Gly Leu Glu Trp Val
                35                  40                  45

Ser Ala Ile Ser Ser Asn Gly Asp Ile Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Pro Leu Val Tyr Thr Gly Phe Ala Tyr Trp Gly Gln
               100                 105                 110

Gly Thr Leu Val Thr Val Ser Ser
           115                 120

<210> SEQ ID NO 97
<211> LENGTH: 120
<212> TYPE: PRT
<213> ORGANISM: Homo sapiens

<400> SEQUENCE: 97

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Tyr Met Asn Trp Val Arg Gln Ala Pro Gly Lys Gly Leu Glu Trp Val
                35                  40                  45

Ser Ala Ile Ser Thr Asn Gly Trp Gln Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Pro Leu Val Tyr Thr Gly Phe Ala Tyr Trp Gly Gln
```

Gly Thr Leu Val Thr Val Ser Ser
        115                 120

<210> SEQ ID NO 98
<211> LENGTH: 120
<212> TYPE: PRT
<213> ORGANISM: Homo sapiens

<400> SEQUENCE: 98

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Asn Trp Val Arg Gln Ala Pro Gly Lys Gly Leu Glu Trp Val
        35                  40                  45

Ser Ala Ile Asn Met Ile Gly Asn Val Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Pro Leu Val Tyr Thr Gly Phe Ala Tyr Trp Gly Gln
            100                 105                 110

Gly Thr Leu Val Thr Val Ser Ser
        115                 120

<210> SEQ ID NO 99
<211> LENGTH: 120
<212> TYPE: PRT
<213> ORGANISM: Homo sapiens

<400> SEQUENCE: 99

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Asn Trp Val Arg Gln Ala Pro Gly Lys Gly Leu Glu Trp Val
        35                  40                  45

Ser Tyr Ile Asn Pro Asn Gly Met Met Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Pro Leu Val Tyr Thr Gly Phe Ala Tyr Trp Gly Gln
            100                 105                 110

Gly Thr Leu Val Thr Val Ser Ser
        115                 120

<210> SEQ ID NO 100
<211> LENGTH: 120
<212> TYPE: PRT
<213> ORGANISM: Homo sapiens

<400> SEQUENCE: 100

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Asn Trp Val Arg Gln Ala Pro Gly Lys Gly Leu Glu Trp Val
        35                  40                  45

Ser Val Ile Ser Pro Gly Gly Glu Ala Lys Ser Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Pro Leu Val Tyr Thr Gly Phe Ala Tyr Trp Gly Gln
                100                 105                 110

Gly Thr Leu Val Thr Val Ser Ser
            115                 120

<210> SEQ ID NO 101
<211> LENGTH: 120
<212> TYPE: PRT
<213> ORGANISM: Homo sapiens

<400> SEQUENCE: 101

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Asn Trp Val Arg Gln Ala Pro Gly Lys Gly Leu Glu Trp Val
        35                  40                  45

Ser Ala Ile Ser Gly Asn Gly Gly His Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Pro Leu Val Tyr Thr Gly Phe Ala Tyr Trp Gly Gln
                100                 105                 110

Gly Thr Leu Val Thr Val Ser Ser
            115                 120

<210> SEQ ID NO 102
<211> LENGTH: 120
<212> TYPE: PRT
<213> ORGANISM: Homo sapiens

<400> SEQUENCE: 102

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Asn Trp Val Arg Gln Ala Pro Gly Lys Gly Leu Glu Trp Val
        35                  40                  45

Ser Ala Ile Ser Met Asp Gly Val Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

```
Ala Arg Asp Leu Pro Leu Val Tyr Thr Gly Phe Ala Tyr Trp Gly Gln
            100                 105                 110

Gly Thr Leu Val Thr Val Ser Ser
        115                 120

<210> SEQ ID NO 103
<211> LENGTH: 120
<212> TYPE: PRT
<213> ORGANISM: Homo sapiens

<400> SEQUENCE: 103

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Asn Trp Val Arg Gln Ala Pro Gly Lys Gly Leu Glu Trp Val
        35                  40                  45

Ser Ala Ile Ser Asn Asn Gly Asn Val Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Pro Leu Val Tyr Thr Gly Phe Ala Tyr Trp Gly Gln
            100                 105                 110

Gly Thr Leu Val Thr Val Ser Ser
        115                 120

<210> SEQ ID NO 104
<211> LENGTH: 120
<212> TYPE: PRT
<213> ORGANISM: Homo sapiens

<400> SEQUENCE: 104

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Asn Trp Val Arg Gln Ala Pro Gly Lys Gly Leu Glu Trp Val
        35                  40                  45

Ser Ala Ile Ser Met His Gly Asp Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Pro Leu Val Tyr Thr Gly Phe Ala Tyr Trp Gly Gln
            100                 105                 110

Gly Thr Leu Val Thr Val Ser Ser
        115                 120

<210> SEQ ID NO 105
<211> LENGTH: 123
<212> TYPE: PRT
<213> ORGANISM: Homo sapiens

<400> SEQUENCE: 105
```

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser His Ile Arg Lys Lys Asn Thr Ser Tyr Thr Glu Tyr Ala Ala
50                      55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
            85                  90                  95

Tyr Cys Ala Arg Glu Asp Gly Ser Tyr Met Thr Asp Tyr Phe Ala Tyr
            100                 105                 110

Trp Gly Gln Gly Thr Leu Val Thr Val Ser Ser
            115                 120

<210> SEQ ID NO 106
<211> LENGTH: 120
<212> TYPE: PRT
<213> ORGANISM: Homo sapiens

<400> SEQUENCE: 106

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Asn Ile Gln Arg Val Gly Ser Thr Tyr Tyr Ala Asp Ser Val Lys
50                      55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Glu Asp Gly Ser Tyr Met Thr Asp Tyr Phe Ala Tyr Trp Gly Gln
            100                 105                 110

Gly Thr Leu Val Thr Val Ser Ser
            115                 120

<210> SEQ ID NO 107
<211> LENGTH: 324
<212> TYPE: DNA
<213> ORGANISM: Homo sapiens

<400> SEQUENCE: 107
gatatcgaac tgacccagcc gccttcagtg agcgttgcac caggtcagac cgcgcgtatc      60
tcgtgtagcg gcgataatat tggtcattat tatgtttctt ggtaccagca gaaacccggg     120
caggcgccag ttcttgtgat ttattctgat tctaatcgtc cctcaggcat cccggaacgc     180
tttagcggat ccaacagcgg caacaccgcg accctgacca ttagcggcac tcaggcggaa     240
gacgaagcgg attattattg ccagtctgct gataattttc cttttgtgtt tggcggcggc     300
acgaagttaa ccgtcctagg tcag                                            324

<210> SEQ ID NO 108
<211> LENGTH: 330

<212> TYPE: DNA
<213> ORGANISM: Homo sapiens

<400> SEQUENCE: 108

```
gatatcgaac tgacccagcc gccttcagtg agcgttgcac caggtcagac cgcgcgtatc    60
tcgtgtagcg gcgataatat tggtcattat tatgtttctt ggtaccagca gaaacccggg   120
caggcgccag ttcttgtgat ttattctgat tctaatcgtc cctcaggcat cccggaacgc   180
tttagcggat ccaacagcgg caacaccgcg accctgacca ttagcggcac tcaggcggaa   240
gacgaagcgg attattattg ccagtcttat actatgtctg atgttcttgt tgtgtttggc   300
ggcggcacga agttaaccgt cctaggtcag                                    330
```

<210> SEQ ID NO 109
<211> LENGTH: 108
<212> TYPE: PRT
<213> ORGANISM: Homo sapiens

<400> SEQUENCE: 109

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly His Tyr Tyr Val
            20                  25                  30

Ser Trp Tyr Gln Gln Lys Pro Gly Gln Ala Pro Val Leu Val Ile Tyr
        35                  40                  45

Ser Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Ala Asp Asn Phe Pro Phe Val
                85                  90                  95

Phe Gly Gly Gly Thr Lys Leu Thr Val Leu Gly Gln
            100                 105

<210> SEQ ID NO 110
<211> LENGTH: 110
<212> TYPE: PRT
<213> ORGANISM: Homo sapiens

<400> SEQUENCE: 110

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly His Tyr Tyr Val
            20                  25                  30

Ser Trp Tyr Gln Gln Lys Pro Gly Gln Ala Pro Val Leu Val Ile Tyr
        35                  40                  45

Ser Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Thr Met Ser Asp Val Leu
                85                  90                  95

Val Val Phe Gly Gly Gly Thr Lys Leu Thr Val Leu Gly Gln
            100                 105                 110

<210> SEQ ID NO 111
<211> LENGTH: 363
<212> TYPE: DNA

<213> ORGANISM: Homo sapiens

<400> SEQUENCE: 111

```
caggtgcaat tggttcagag cggcgcggaa gtgaaaaaac cgggcgcgag cgtgaaagtg    60
agctgcaaag cctccggata tacctttact tcttattcta ttaattgggt ccgccaagcc   120
cctgggcagg gtctcgagtg gatgggctat atcgatccga atcgtggcaa tacgaattac   180
gcgcagaagt tcagggccg ggtgaccatg acccgtgata ccagcattag caccgcgtat   240
atggaactga gcagcctgcg tagcgaagat acggccgtgt attattgcgc gcgtgagtat   300
atttatttta ttcatggtat gcttgatttt tggggccaag gcaccctggt gacggttagc   360
tca                                                                 363
```

<210> SEQ ID NO 112
<211> LENGTH: 366
<212> TYPE: DNA
<213> ORGANISM: Homo sapiens

<400> SEQUENCE: 112

```
caggtgcaat tggtggaaag cggcggcggc ctggtgcaac cgggcggcag cctgcgtctg    60
agctgcgcgg cctccggatt tacctttct aattatggta tgcattgggt gcgccaagcc   120
cctgggaagg gtctcgagtg ggtgagcaat atccgttctg atggtagctg gacctattat   180
gcggatagcg tgaaaggccg ttttaccatt tcacgtgata attcgaaaaa caccctgtat   240
ctgcaaatga acagcctgcg tgcggaagat acggccgtgt attattgcgc gcgtcgttat   300
tggtctaagt ctcatgcttc tgttactgat tattgggcc aaggcaccct ggtgacggtt   360
agctca                                                              366
```

<210> SEQ ID NO 113
<211> LENGTH: 366
<212> TYPE: DNA
<213> ORGANISM: Homo sapiens

<400> SEQUENCE: 113

```
caggtgcaat tggtggaaag cggcggcggc ctggtgcaac cgggcggcag cctgcgtctg    60
agctgcgcgg cctccggatt tacctttct tcttatggta tgcattgggt gcgccaagcc   120
cctgggaagg gtctcgagtg ggtgagcaat atctattctg atggtagcaa tacctttat    180
gcggatagcg tgaaaggccg ttttaccatt tcacgtgata attcgaaaaa caccctgtat   240
ctgcaaatga acagcctgcg tgcggaagat acggccgtgt attattgcgc gcgtaatatg   300
tatcgttggc cttttcatta ttttttgat tattgggcc aaggcaccct ggtgacggtt    360
agctca                                                              366
```

<210> SEQ ID NO 114
<211> LENGTH: 121
<212> TYPE: PRT
<213> ORGANISM: Homo sapiens

<400> SEQUENCE: 114

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ser Ile Asn Trp Val Arg Gln Ala Pro Gly Gln Gly Leu Glu Trp Met
        35                  40                  45

```
Gly Tyr Ile Asp Pro Asn Arg Gly Asn Thr Asn Tyr Ala Gln Lys Phe
    50              55                  60
Gln Gly Arg Val Thr Met Thr Arg Asp Thr Ser Ile Ser Thr Ala Tyr
65              70                  75                  80
Met Glu Leu Ser Ser Leu Arg Ser Glu Asp Thr Ala Val Tyr Tyr Cys
                85                  90                  95
Ala Arg Glu Tyr Ile Tyr Phe Ile His Gly Met Leu Asp Phe Trp Gly
                100                 105                 110
Gln Gly Thr Leu Val Thr Val Ser Ser
            115                 120
```

<210> SEQ ID NO 115
<211> LENGTH: 122
<212> TYPE: PRT
<213> ORGANISM: Homo sapiens

<400> SEQUENCE: 115

```
Gln Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asn Tyr
                20                  25                  30
Gly Met His Trp Val Arg Gln Ala Pro Gly Lys Gly Leu Glu Trp Val
            35                  40                  45
Ser Asn Ile Arg Ser Asp Gly Ser Trp Thr Tyr Tyr Ala Asp Ser Val
    50              55                  60
Lys Gly Arg Phe Thr Ile Ser Arg Asp Asn Ser Lys Asn Thr Leu Tyr
65              70                  75                  80
Leu Gln Met Asn Ser Leu Arg Ala Glu Asp Thr Ala Val Tyr Tyr Cys
                85                  90                  95
Ala Arg Tyr Trp Ser Lys Ser His Ala Ser Val Thr Asp Tyr Trp
                100                 105                 110
Gly Gln Gly Thr Leu Val Thr Val Ser Ser
            115                 120
```

<210> SEQ ID NO 116
<211> LENGTH: 122
<212> TYPE: PRT
<213> ORGANISM: Homo sapiens

<400> SEQUENCE: 116

```
Gln Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
                20                  25                  30
Gly Met His Trp Val Arg Gln Ala Pro Gly Lys Gly Leu Glu Trp Val
            35                  40                  45
Ser Asn Ile Tyr Ser Asp Gly Ser Asn Thr Phe Tyr Ala Asp Ser Val
    50              55                  60
Lys Gly Arg Phe Thr Ile Ser Arg Asp Asn Ser Lys Asn Thr Leu Tyr
65              70                  75                  80
Leu Gln Met Asn Ser Leu Arg Ala Glu Asp Thr Ala Val Tyr Tyr Cys
                85                  90                  95
Ala Arg Asn Met Tyr Arg Trp Pro Phe His Tyr Phe Phe Asp Tyr Trp
                100                 105                 110
Gly Gln Gly Thr Leu Val Thr Val Ser Ser
            115                 120
```

<210> SEQ ID NO 117
<211> LENGTH: 342
<212> TYPE: DNA
<213> ORGANISM: Homo sapiens

<400> SEQUENCE: 117

```
gatatcgtga tgacccagag cccactgagc ctgccagtga ctccgggcga gcctgcgagc      60
attagctgca gaagcagcca aagcctgctt tttattgatg caataatta tctgaattgg     120
taccttcaaa aaccaggtca aagcccgcag ctattaattt atcttggttc taatcgtgcc    180
agtggggtcc cggatcgttt tagcggctct ggatccggca ccgattttac cctgaaaatt    240
agccgtgtgg aagctgaaga cgtgggcgtg tattattgcc agcagtattc ttctaagtct    300
gctacctttg gccagggtac gaaagttgaa attaaacgta cg                       342
```

<210> SEQ ID NO 118
<211> LENGTH: 327
<212> TYPE: DNA
<213> ORGANISM: Homo sapiens

<400> SEQUENCE: 118

```
gatatccaga tgacccagag cccgtctagc ctgagcgcga gcgtgggtga tcgtgtgacc      60
attacctgca gagcgagcca ggatatttct gcttttctga attggtacca gcagaaacca    120
ggtaaagcac cgaaactatt aatttataag gtttctaatt tgcaaagcgg ggtcccgtcc    180
cgttttagcg gctctggatc cggcactgat tttaccctga ccattagcag cctgcaacct    240
gaagactttg cgacttatta ttgccagcag gcttattctg ttctattac ctttggccag     300
ggtacgaaag ttgaaattaa acgtacg                                         327
```

<210> SEQ ID NO 119
<211> LENGTH: 324
<212> TYPE: DNA
<213> ORGANISM: Homo sapiens

<400> SEQUENCE: 119

```
gatatcgaac tgacccagcc gccttcagtg agcgttgcac aggtcagac cgcgcgtatc       60
tcgtgtagcg gcgataatat tggtaataag tatgtttctt ggtaccagca gaaacccggg    120
caggcgccag ttgttgtgat ttatggtgat aataatcgtc cctcaggcat cccgaacgc     180
tttagcggat ccaacagcgg caacaccgcg accctgacca ttagcggcac tcaggcggaa    240
gacgaagcgg attattattg ctcttcttat gattcttctt attttgtgtt tggcggcggc    300
acgaagttaa ccgttcttgg ccag                                           324
```

<210> SEQ ID NO 120
<211> LENGTH: 114
<212> TYPE: PRT
<213> ORGANISM: Homo sapiens

<400> SEQUENCE: 120

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Phe Ile
            20                  25                  30

Asp Gly Asn Asn Tyr Leu Asn Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gln Gln Tyr
                 85                  90                  95

Ser Ser Lys Ser Ala Thr Phe Gly Gln Gly Thr Lys Val Glu Ile Lys
            100                 105                 110

Arg Thr

<210> SEQ ID NO 121
<211> LENGTH: 109
<212> TYPE: PRT
<213> ORGANISM: Homo sapiens

<400> SEQUENCE: 121

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Ser Ala Phe
                 20                  25                  30

Leu Asn Trp Tyr Gln Gln Lys Pro Gly Lys Ala Pro Lys Leu Leu Ile
             35                  40                  45

Tyr Lys Val Ser Asn Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Tyr Ser Gly Ser Ile
                 85                  90                  95

Thr Phe Gly Gln Gly Thr Lys Val Glu Ile Lys Arg Thr
            100                 105

<210> SEQ ID NO 122
<211> LENGTH: 108
<212> TYPE: PRT
<213> ORGANISM: Homo sapiens

<400> SEQUENCE: 122

Asp Ile Glu Leu Thr Gln Pro Pro Ser Val Ser Val Ala Pro Gly Gln
  1               5                  10                  15

Thr Ala Arg Ile Ser Cys Ser Gly Asp Asn Ile Gly Asn Lys Tyr Val
                 20                  25                  30

Ser Trp Tyr Gln Gln Lys Pro Gly Gln Ala Pro Val Val Ile Tyr
             35                  40                  45

Gly Asp Asn Asn Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Ser Ser Tyr Asp Ser Ser Tyr Phe Val
                 85                  90                  95

Phe Gly Gly Gly Thr Lys Leu Thr Val Leu Gly Gln
            100                 105

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 123
atggccaact gcgagttcag c                                              21

<210> SEQ ID NO 124
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
tcagatctca gatgtgcaag atgaatc                                        27

<210> SEQ ID NO 125
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
ttggtaccag gtggcgccag cagtg                                          25

<210> SEQ ID NO 126
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
ttggtaccat ggccaactgc gag                                            23

<210> SEQ ID NO 127
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
ccgatatcag atctcagatg tgcaagatg                                      29

<210> SEQ ID NO 128
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
ccgatatcga tctcagatgt gcaagatg                                       28

<210> SEQ ID NO 129
<211> LENGTH: 29
<212> TYPE: PRT
<213> ORGANISM: Homo sapiens

<400> SEQUENCE: 129

Met Lys His Leu Trp Phe Phe Leu Leu Leu Val Ala Ala Pro Arg Trp
1               5                   10                  15

```
Val Leu Ser Gln Val Glu Phe Cys Arg Arg Leu Ala Gln
            20                  25
```

<210> SEQ ID NO 130
<211> LENGTH: 133
<212> TYPE: PRT
<213> ORGANISM: Homo sapiens

<400> SEQUENCE: 130

```
Met Val Leu Gln Thr Gln Val Phe Ile Ser Leu Leu Leu Trp Ile Ser
1               5                   10                  15

Gly Ala Tyr Gly Asp Ile Val Met Ile Lys Arg Thr Val Ala Ala Pro
            20                  25                  30

Ser Val Phe Ile Phe Pro Pro Ser Asp Glu Gln Leu Lys Ser Gly Thr
        35                  40                  45

Ala Ser Val Val Cys Leu Leu Asn Asn Phe Tyr Pro Arg Glu Ala Lys
    50                  55                  60

Val Gln Trp Lys Val Asp Asn Ala Leu Gln Ser Gly Asn Ser Gln Glu
65                  70                  75                  80

Ser Val Thr Glu Gln Asp Ser Lys Asp Ser Thr Tyr Ser Leu Ser Ser
                85                  90                  95

Thr Leu Thr Leu Ser Lys Ala Asp Tyr Glu Lys His Lys Val Tyr Ala
            100                 105                 110

Cys Glu Val Thr His Gln Gly Leu Ser Ser Pro Val Thr Lys Ser Phe
        115                 120                 125

Asn Arg Gly Glu Cys
    130
```

<210> SEQ ID NO 131
<211> LENGTH: 26
<212> TYPE: PRT
<213> ORGANISM: Homo sapiens

<400> SEQUENCE: 131

```
Met Ala Trp Ala Leu Leu Leu Leu Thr Leu Leu Thr Gln Gly Thr Gly
1               5                   10                  15

Ser Trp Ala Asp Ile Val Met His Glu Val
            20                  25
```

<210> SEQ ID NO 132
<211> LENGTH: 120
<212> TYPE: PRT
<213> ORGANISM: Homo sapiens

<400> SEQUENCE: 132

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95
```

Ala Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 133
<211> LENGTH: 119
<212> TYPE: PRT
<213> ORGANISM: Homo sapiens

<400> SEQUENCE: 133

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Gly Met Ser Trp Val Arg Gln Ala Pro Gly Lys Gly Leu Glu Trp Val
        35                  40                  45

Ser Asn Ile Ser Tyr Leu Ser Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Gly Tyr Phe Asn Tyr Ala Asp Val Trp Gly Gln Gly
            100                 105                 110

Thr Leu Val Thr Val Ser Ser
        115

<210> SEQ ID NO 134
<211> LENGTH: 109
<212> TYPE: PRT
<213> ORGANISM: Homo sapiens

<400> SEQUENCE: 134

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly His Tyr Tyr Ala
            20                  25                  30

Ser Trp Tyr Gln Gln Lys Pro Gly Gln Ala Pro Val Leu Val Ile Tyr
        35                  40                  45

Arg Asp Asn Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Asp Tyr Leu His Asp Phe
                85                  90                  95

Val Phe Gly Gly Gly Thr Lys Leu Thr Val Leu Gly Gln
            100                 105

<210> SEQ ID NO 135
<211> LENGTH: 109
<212> TYPE: PRT
<213> ORGANISM: Homo sapiens

<400> SEQUENCE: 135

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr

```
                    20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr
            100                 105

<210> SEQ ID NO 136
<211> LENGTH: 114
<212> TYPE: PRT
<213> ORGANISM: Homo sapiens

<400> SEQUENCE: 136

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gln Gln His
                 85                  90                  95

Tyr Thr Thr Pro Pro Thr Phe Gly Gln Gly Thr Lys Leu Glu Ile Lys
            100                 105                 110

Arg Thr

<210> SEQ ID NO 137
<211> LENGTH: 110
<212> TYPE: PRT
<213> ORGANISM: Homo sapiens
<220> FEATURE:
<221> NAME/KEY: MOD_RES
<222> LOCATION: (86)
<223> OTHER INFORMATION: Thr or Val

<400> SEQUENCE: 137

Asp Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Val Pro Ala Arg Phe Ser
 50                  55                  60

Gly Ser Gly Ser Gly Thr Asp Phe Thr Leu Thr Ile Ser Ser Leu Glu
 65                  70                  75                  80

Pro Glu Asp Phe Ala Xaa Tyr Tyr Cys Gln Gln His Tyr Thr Thr Pro
                 85                  90                  95

Pro Thr Phe Gly Gln Gly Thr Lys Val Glu Ile Lys Arg Thr
```

<210> SEQ ID NO 138
<211> LENGTH: 330
<212> TYPE: PRT
<213> ORGANISM: Homo sapiens

<400> SEQUENCE: 138

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 139
<211> LENGTH: 109
<212> TYPE: PRT
<213> ORGANISM: Homo sapiens

```
<400> SEQUENCE: 139

Thr Val Leu Gly Gln Pro Lys Ala Ala Pro Ser Val Thr Leu Phe Pro
1               5                   10                  15

Pro Ser Ser Glu Glu Leu Gln Ala Asn Lys Ala Thr Leu Val Cys Leu
                20                  25                  30

Ile Ser Asp Phe Tyr Pro Gly Ala Val Thr Val Ala Trp Lys Gly Asp
            35                  40                  45

Ser Ser Pro Val Lys Ala Gly Val Glu Thr Thr Thr Pro Ser Lys Gln
        50                  55                  60

Ser Asn Asn Lys Tyr Ala Ala Ser Ser Tyr Leu Ser Leu Thr Pro Glu
65                  70                  75                  80

Gln Trp Lys Ser His Arg Ser Tyr Ser Cys Gln Val Thr His Glu Gly
                85                  90                  95

Ser Thr Val Glu Lys Thr Val Ala Pro Thr Glu Cys Ser
            100                 105
```